(12) United States Patent
Blench et al.

(10) Patent No.: US 7,208,494 B2
(45) Date of Patent: Apr. 24, 2007

(54) 5HT2C RECEPTOR AGONISTS

(75) Inventors: Toby Jonathan Blench, Wokingham (GB); Paul Hebeisen, Basel (CH); Hans Richter, Grenzach-Wyhlen (DE); Stephan Roever, Inzlingen (DE)

(73) Assignees: Hoffmann-La Roche Inc., Nutley, NJ (US); Vernalis Research Limited, Winnersh (GB)

( * ) Notice: Subject to any disclaimer, the term of this patent is extended or adjusted under 35 U.S.C. 154(b) by 171 days.

(21) Appl. No.: 10/876,954

(22) Filed: Jun. 25, 2004

(65) Prior Publication Data

US 2005/0026925 A1 Feb. 3, 2005

(30) Foreign Application Priority Data

Jun. 26, 2003 (GB) .................................. 0314967.1

(51) Int. Cl.
*A01N 43/58* (2006.01)
*A01N 43/60* (2006.01)
*A61K 31/50* (2006.01)
*A61K 31/495* (2006.01)
*C07D 471/00* (2006.01)

(52) U.S. Cl. ....................................... 514/250; 544/346
(58) Field of Classification Search ...................... None
See application file for complete search history.

(56) References Cited

U.S. PATENT DOCUMENTS

| | | | |
|---|---|---|---|
| 3,317,524 | A | 5/1967 | Freed et al. |
| 4,598,089 | A | 7/1986 | Hadvary et al. |
| 4,776,409 | A | 10/1988 | Manchak, Jr. |
| 4,844,807 | A | 7/1989 | Manchak, Jr. |
| 4,844,839 | A | 7/1989 | Manchak, Jr. |
| 4,931,463 | A | 6/1990 | Barbier et al. |
| 4,983,746 | A | 1/1991 | Barbier et al. |
| 5,175,186 | A | 12/1992 | Barbier et al. |
| 5,245,056 | A | 9/1993 | Karpf et al. |
| 5,246,960 | A | 9/1993 | Barbier et al. |
| 5,399,720 | A | 3/1995 | Karpf et al. |
| 5,432,177 | A | 7/1995 | Baker et al. |
| 6,004,996 | A | 12/1999 | Shah et al. |
| 6,365,598 | B1 | 4/2002 | Adams et al. |
| 6,380,238 | B1 | 4/2002 | Adams et al. |
| 6,433,175 | B1 | 8/2002 | Adams et al. |
| 6,552,062 | B1 | 4/2003 | Adams et al. |
| 6,610,685 | B2 | 8/2003 | Bentley et al. |
| 6,706,750 | B1 | 3/2004 | Bentley et al. |
| 2002/0035110 | A1 | 3/2002 | Bentley et al. |
| 2002/0160997 | A1 | 10/2002 | Bentley et al. |
| 2003/0216401 | A1 | 11/2003 | Bentley et al. |
| 2004/0039200 | A1 | 2/2004 | Adams et al. |
| 2004/0092525 | A1 | 5/2004 | Adams et al. |

FOREIGN PATENT DOCUMENTS

EP 185359 12/1985

| | | |
|---|---|---|
| EP | 189577 | 12/1985 |
| EP | 443449 | 2/1991 |
| EP | 524495 | 7/1992 |
| EP | 0572863 | 12/1993 |
| EP | 655440 | 5/1995 |
| EP | 0 657426 | 6/1995 |
| EP | 1 132389 | 12/2001 |
| WO | WO 98/30548 | 7/1998 |
| WO | WO 99/34786 | 7/1999 |
| WO | WO 00/09122 | 2/2000 |
| WO | WO 00/09123 | 2/2000 |
| WO | WO 00/12510 | 3/2000 |
| WO | WO 200012482 | 3/2000 |
| WO | WO 200017170 | 3/2000 |
| WO | WO 0035922 | 6/2000 |
| WO | WO 00/44753 | 8/2000 |
| WO | WO 200112602 | 2/2001 |
| WO | WO 03/064423 A1 | 8/2003 |

OTHER PUBLICATIONS

J. Am. Chem. Soc (1983), 105(22), 6719.
J. Org. Chem. (1976) 14 (17), 2846.
Keller & Wahli: Trends Endocrin. Metab. (1993) 4, 291-296.
MacDonald & Lane: Current Biology, vol. 5, pp. 618-621 (1995).
Parker, "Obesity: Trends and Treatments", Scrip Reports, PJB Publications Limited, (1996).
Kennett et al., Psychopharmacology, 96, pp. 93-100 (1988).
Kennett et al., Eur. J. Pharmacol., 141, pp. 429-435 (1987).
Kitchener et al., Psychopharmacology, 113, pp. 369-377 (1994).
Walsh et al., Psychopharmacology, 116, pp. 120-122 (1994).

(Continued)

Primary Examiner—Zachary C. Tucker
(74) Attorney, Agent, or Firm—George W. Johnston; Dennis P. Tramaloni; Samuel H. Megerditchian

(57) ABSTRACT

The present invention provides piperazine derivatives of formula (I)

(I)

as well as pharmaceutically acceptable salts and esters thereof, wherein $R^1$ to $R^5$ have the significance given in the description. They can be used for the treatment of obesity.

21 Claims, No Drawings

OTHER PUBLICATIONS

Sargeant et al., Psychopharmacology, 133, pp. 309-312 (1997).
Tecott et al., Nature, vol. 374, pp. 542-546 (1995).
Kennett et al., Neuropharmacology, vol. 36, pp. 609-620 (1997).
Hoyer et al., European J. Pharmacology, 118, pp. 13-23 (1985).
Schmuck et al., FEBS Letters, 342, pp. 85-90 (1994).
McKenna et al., J. Neuroscience, 9, pp. 3482-3490 (1989).
Cheng et al., Biochem. Pharmacol., 22(23) pp. 3099-3108 (1973).
Kondo et al., J. Org. Chem., 62, pp. 6507-6511 (1997).
Mutoh et al., J. Antibiot., 47(12), pp. 1369-1375 (1994).
Abstract CA 2132887, 1995.
Abstract CA 2153937, 1996.
Kiuchi, et. al., Pub Med Abstract (Nippon Rinsho 52(5): 1190-5), May 1994.
Damasio, Alzheimer's Disease and Related Dementias, Cecil Textbook of Medicine, 20th Ed., V. 2, p. 1992-6 (1996).
Layzer, Degenerative Diseases of the Nervous System, Cecil Textbook of Medicine, 20th Ed., V. 2, p. 2050-7 (1996).

5HT2C RECEPTOR AGONISTS

BACKGROUND OF THE INVENTION

It has been recognised that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI), which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmLess) side-effects such as diarrhea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

The compounds of formula (I) are useful in the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes). The diabetes may be diabetes secondary to pancreatic disease; or diabetes related to steroid use. The compounds of formula (I) are also useful in the treatment and/or prevention of the sequelae of hyperglycaemia; in the treatment and/or prevention of diabetic complications; and in the treatment of insulin dependence.

The invention is of particular use in the treatment or prevention of diabetes mellitus (including Type II or non-insulin dependent diabetes mellitus (NIDDM); Type I or insulin dependent diabetes mellitus (IDDM); and Type III or malnutrition-related diabetes), and particularly in the treatment or prevention of Type II diabetes.

The present invention encompasses the use of compounds according to formula I for the acute and/or chronic treatment and/or prevention of disorders involving elevated plasma blood glucose, particularly the acute and/or chronic treatment of disorders involving elevated plasma blood glucose, and especially acute treatment of disorders involving elevated plasma blood glucose.

Diabetes is a disease in which a patient's ability to control glucose levels in blood is impaired, because the ability to respond properly to the action of insulin has been partially lost. In type II diabetes, often referred to as non-insulin dependent diabetes mellitus (NIDDM), which afflicts 80–90% of all diabetic patients in developed countries, the Islets of Langerhans in the pancreas still produce insulin. However, the target organs, mainly muscle, liver and adipose tissue, exhibit a profound resistance to insulin stimulation, thus the body compensates by producing abnormally high levels of insulin. In the later stages of the disease, however, insulin secretion decreases due to pancreas exhaustion.

Current first line treatment for diabetes generally involves adoption of a diet low in fat and glucose and taking regular exercise. However, compliance can be moderate and as the disease progresses, treatment with hypoglycemic drugs, e.g. sulfonylureas or metformin, becomes necessary. A promising new class of drugs has recently been introduced that resensitize patients to their own insulin (insulin sensitizers), thereby reverting blood glucose and triglyceride levels to normal, and thus abolishing, or at least reducing, the requirement for exogenous insulin. Troglitazone (Resulin™) and rosiglitazone (Avandia™) belong to the thiazolidinediones (TZD) class of PPARγ-agonists and were the first representatives of the class approved for NIDDM treatment in several countries. These compounds, however, suffer from side effects including rare but severe liver toxicity (as seen with troglitazone), and increased body weight in humans. Therefore, new, better and more efficacious drugs for the treatment of conditions involving hyperglycemia, particularly NIDDM are urgently needed. Recent studies provided evidence that coagonism of PPARα and PPARγ would result in compounds with enhanced therapeutic potential, i.e. with an improved lipid profile effect on top of the normalization of glucose- and insulin-levels (Keller and Wahli: Trends Endocrin. Metab. 1993; 4: 291–296, Macdonald and Lane: Current Biology Vol.5 pp. 618–621 (1995)). The novel compounds of the present invention can be used as efficacious drugs for the treatment and prevention of diabetes, particularly of non-insulin dependent diabetes mellitus.

SUMMARY OF THE INVENTION

The present invention provides compounds of formula I and their pharmaceutically acceptable salts and esters

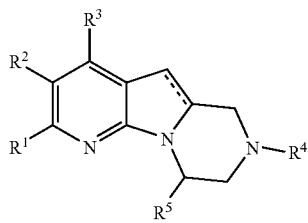

wherein
$R^1$ is hydrogen, alkyl, cycloalkyl, halogen, alkoxy, cycloalkoxy, alkoxyalkyl, cycloalkoxyalkyl, cycloalkylalkoxyalkyl, cycloalkylalkoxy, hydroxyalkyl, $R^8$—O—N=($R^6$)C—, alkylsulfanyl or alkyl substituted with halogen;
$R^2$ is alkyl, cycloalkyl, alkoxy, cycloalkoxy, cycloalkylalkoxy, halogen, hydroxy, hydroxyalkyl, alkoxyalkyl, cycloalkoxyalkyl, cycloalkylalkoxyalkyl, cycloalkylalkoxy, alkoxyalkoxy, cycloalkylalkoxyalkyl, hydroxyalkoxy, alkyl-$SO_2$— or aralkoxyalkyl;
$R^3$ is hydrogen, alkyl, cycloalkyl, hydroxyalkyl, alkoxyalkyl, cycloalkoxyalkyl or $R^7$—O—N=CH—;
$R^4$ is hydrogen or alkyl;
$R^5$ is alkyl;
$R^6$ is hydrogen or alkyl;
$R^7$ is hydrogen, alkyl or cycloalkyl; and
$R^8$ is hydrogen, alkyl or cycloalkyl.

The compounds of the present invention are useful in the treatment of obesity or type II diabetes.

DETAILED DESCRIPTION OF THE INVENTION

The present invention provides a compound of formula (I):

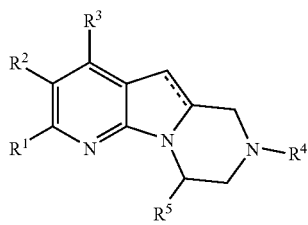

wherein
$R^1$ is hydrogen, alkyl, cycloalkyl, halogen, alkoxy, cycloalkoxy, alkoxyalkyl, cycloalkoxyalkyl, cycloalkylalkoxyalkyl, cycloalkylalkoxy, hydroxyalkyl, $R^8$—O—N=($R^6$)C—, alkylsulfanyl or alkyl substituted with halogen;
$R^2$ is alkyl, cycloalkyl, alkoxy, cycloalkoxy, cycloalkylalkoxy, halogen, hydroxy, hydroxyalkyl, alkoxyalkyl, cycloalkoxyalkyl, cycloalkylalkoxyalkyl, cycloalkylalkoxy, alkoxyalkoxy, cycloalkylalkoxyalkyl, hydroxyalkoxy, alkyl-$SO_2$— or aralkoxyalkyl;
$R^3$ is hydrogen, alkyl, cycloalkyl, hydroxyalkyl, alkoxyalkyl, cycloalkoxyalkyl or $R^7$—O—N=CH—;
$R^4$ is hydrogen or alkyl;
$R^5$ is alkyl;
$R^6$ is hydrogen or alkyl;
$R^7$ is hydrogen, alkyl or cycloalkyl;
$R^8$ is hydrogen, alkyl or cycloalkyl;
or a pharmaceutically acceptable salt or ester thereof.

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl and isopropyl. Particularly preferred are methyl and ethyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclopropyl and cyclopentyl and particularly cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

The term "cycloalkoxy", alone or in combination, signifies a group of the formula cycloalkyl-O— in which the term "cycloalkyl" has the previously given significance.

The term "hydroxyalkyl", alone or in combination, signifies an alkyl group as previously defined, wherein one or several hydrogen atoms, preferably one hydrogen atom has been replaced by a hydroxyl group. Examples are hydroxymethyl, hydroxyethyl and 2-hydroxyethyl.

The term "alkyl substituted with halogen", alone or in combination, signifies an alkyl group as previously defined, wherein one or several hydrogen atoms, preferably one to three hydrogen atoms have/has been replaced by halogen. Examples of haloalkyl groups are trifluoromethyl, trifluoroethyl, pentafluoroethyl and trichloromethyl. Preferred examples are monofluoromethyl, difluoromethyl and trifluoromethyl. Particularly preferred is fluoromethyl and difluoromethyl.

The term "carbonyl" refers to a group of the formula —C(O)—.

The term "aryl", alone or in combination, signifies a phenyl or naphthyl group which optionally carries one to three substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert-butoxyphenyl, 4-fluorophenyl, 2-chlorophenyl, 3-chlorophenyl, 4-chlorophenyl, 4-hydroxyphenyl, 1-naphthyl and 2-naphthyl. Preferred is phenyl.

The term "aralkyl", alone or in combination, signifies an alkyl or cycloalkyl group, preferably an alkyl group as previously defined in which one or several, preferably one hydrogen atom has been replaced by an aryl group as defined before. Preferred is benzyl.

The term "aralkoxy", alone or in combination, signifies a group of the formula aralkyl-O— in which the term "aralkyl" has the previously given significance.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methylethylamino, morpholin-1-yl, pyrrolidin-1-yl or piperidinyl etc., preferably amino, dimethylamino and diethylamino and particularly primary amino.

The term "halogen" signifies fluorine, chlorine, bromine or iodine and preferably fluorine, chlorine or bromine and particularly fluorine and chlorine.

The term "carboxy", alone or in combination, signifies a —COOH group.

The term "cyano", alone or in combination, signifies a —CN group.

The term "alkylsulfanyl", alone or in combination, signifies an alkyl-S— group, wherein alkyl is defined as before.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions.

The invention expressly includes pharmaceutically usable solvates of compounds according to formula I. The compounds of formula I can be solvated, e.g. hydrated. The solvation can be effected in the course of the manufacturing process or can take place, e.g. as a consequence of hygroscopic properties of an initially anhydrous compound of formula I (hydration). The term pharmaceutically acceptable salts also includes pharmaceutically usable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The invention expressly includes prodrugs of compounds according to formula I. The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

In the nomenclature used in the present application the carbon atoms of the basic ring system of the compounds according to formula I are numbered as follows:

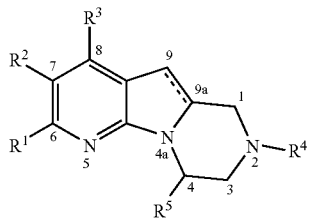
(I)

wherein $R^1$ is attached to the 6-position, $R^2$ is attached to the 7-position, $R^3$ is attached to the 8-position and $R^5$ is attached to the 4-position.

The dotted line in formula I (marked as *) represents a single or a double bond.

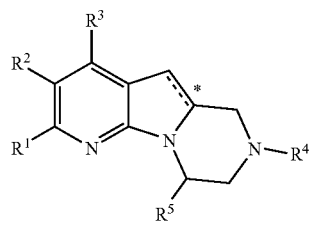
(I)

Accordingly, compounds of formula (I) are of one of the following formulae (Ia) and (Ib)

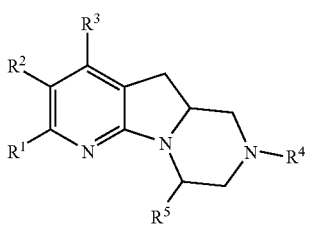
(Ia)

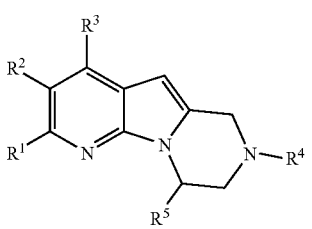
(Ib)

wherein $R^1$ to $R^5$ are defined as before.

Preferred compounds of formula I are those which are of formula Ib. Particularly preferred are compounds of formula I which are of formula Ia.

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom (C*)" means a carbon atom with four different substituents. According to the Cahn-Ingold-Prelog-Convention the asymmetric carbon atom can be of the "R" or "S" configuration.

Preferred are chiral compounds of formula (Ia), wherein the carbon atom number 9a has the R configuration.

Preferred are chiral compounds of formula (Ic),

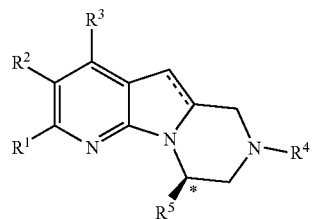
(Ic)

wherein $R^1$ to $R^5$ are defined as before. Formula (Ic) means that the asymmetric carbon atom C*

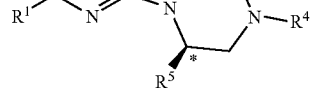
(Ic)

is of the R configuration and $R^1$ to $R^5$ are defined as before.

Further preferred compounds of formula (I) are those, wherein C* is of the R configuration and wherein $R^5$ means alkyl.

Preferred are compounds according to formula I and their pharmaceutically acceptable salts and esters. Particularly preferred are the compounds according to formula I and their pharmaceutically acceptable salts. Preferred salts are the hydrochloride salts.

Preferred is a compound according to formula I, wherein $R^1$ is hydrogen, alkyl, halogen, alkoxy, alkoxyalkyl, cycloalkylalkoxyalkyl, cycloalkylalkoxy, hydroxyalkyl, $R^8$—O—N=$(R^6)$C—, alkylsulfanyl or alkyl substituted with halogen. Particularly preferred compounds of the formula I are those, wherein $R^1$ is hydrogen, alkyl, cycloalkylalkoxyalkyl or hydroxyalkyl.

Another preferred embodiment of the present invention is a compound according to formula I, wherein $R^2$ is alkyl, alkoxy, halogen, hydroxy, alkoxyalkyl, cycloalkylalkyl, alkoxyalkoxy, cycloalkylalkoxyalkyl, hydroxyalkoxy, alkyl-$SO_2$— or aralkoxyalkyl. Particularly preferred is a compound of formula I, wherein $R^2$ is alkyl, alkoxy, halogen or alkoxyalkoxy.

A further preferred aspect of the present invention is a compound according to formula I, wherein $R^3$ is hydrogen, alkyl, hydroxyalkyl, alkoxyalkyl or $R^7$—O—N=CH—. Particularly preferred are those compounds of formula I, wherein $R^3$ is hydrogen.

Further preferred are those compounds of formula I, wherein the compound is of formula

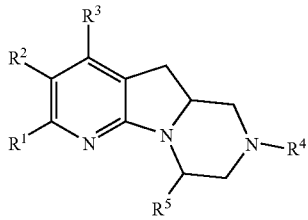

(Ia)

and, wherein $R^1$ to $R^5$ are defined as before.

A further preferred aspect of the present invention is a compound according to formula I, wherein $R^4$ is hydrogen.

Other preferred compounds of formula I are those, wherein the compound is of formula

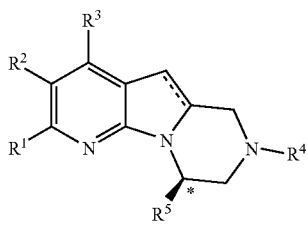

(Ic)

wherein the carbon atom C* to which $R^5$ is attached is of the R configuration and $R^1$ to $R^5$ are defined as before.

Also preferred are compounds of formula I, wherein $R^5$ is methyl.

Further preferred are compounds according to formula I, wherein $R^6$ is hydrogen or methyl.

Other preferred compounds of formula I are those, wherein $R^7$ is hydrogen or alkyl, particularly preferred hydrogen or methyl.

Additionally preferred are those compounds according to formula I, wherein $R^8$ is alkyl.

Particularly preferred are those, wherein $R^8$ is methyl.

Examples of preferred compounds of formula I are:
(R)-6-chloro-7-ethoxy-4-methyl-1,2,3,4-tetrahydro-2,4a,5-triaza-fluorene;
(4R,9aR)-6-chloro-7-ethoxy-4-methyl-1,2,3,4,9,9a-hexahydro-2,4a,5-triaza-fluorene;
(4R,9aR)-6-chloro-4,7-dimethyl-1,2,3,4,9,9a-hexahydro-2,4a,5-triaza-fluorene;
(4R,9aR)-6-bromo-7-ethoxy-4-methyl-1,2,3,4,9,9a-hexahydro-2,4a,5-triaza-fluorene;
(4R,9aR)-7-chloro-4,6-dimethyl-1,2,3,4,9,9a-hexahydro-2,4a,5-triaza-fluorene;
(4R,9aR)-7-bromo-4,6-dimethyl-1,2,3,4,9,9a-hexahydro-2,4a,5-triaza-fluorene;
(4R,9aR)-4,6-dimethyl-1,2,3,4,9,9a-hexahydro-2,4a,5-triaza-fluoren-7-ol;
(4R,9aR)-7-methoxy-4,6-dimethyl-1,2,3,4,9,9a-hexahydro-2,4a,5-triaza-fluorene;
(4R,9aR)-7-ethoxy-4,6-dimethyl-1,2,3,4,9,9a-hexahydro-2,4a,5-triaza-fluorene;
(4R,9aR)-7-isopropoxy-4,6-dimethyl-1,2,3,4,9,9a-hexahydro-2,4a,5-triaza-fluorene;
(4R,9aR)-7-cyclopropylmethoxy-4,6-dimethyl-1,2,3,4,9,9a-hexahydro-2,4a,5-triaza-fluorene;
(4R,9aR)-7-(2-methoxy-ethoxy)-4,6-dimethyl-1,2,3,4,9,9a-hexahydro-2,4a,5-triaza-fluorene;
(4R,9aR)-2-(4,6-dimethyl-1,2,3,4,9,9a-hexahydro-2,4a,5-triaza-fluoren-7-yloxy)-1-ethanol;
(4R,9aR)-4,6,7-trimethyl-1,2,3,4,9,9a-hexahydro-2,4a,5-triaza-fluorene;
(4R,9aR)-7-methoxymethyl-4,6-dimethyl-1,2,3,4,9,9a-hexahydro-2,4a,5-triaza-fluorene;
(4R,9aR)-7-cyclopropylmethoxymethyl-4,6-dimethyl-1,2,3,4,9,9a-hexahydro-2,4a,5-triaza-fluorene;
(4R,9aR)-7-chloro-6-ethyl-4-methyl-1,2,3,4,9,9a-hexahydro-2,4a,5-triaza-fluorene;
(4R,9aR)-7-bromo-6-ethyl-4-methyl-1,2,3,4,9,9a-hexahydro-2,4a,5-triaza-fluorene;
(4R,9aR)-6-ethyl-4,7-dimethyl-1,2,3,4,9,9a-hexahydro-2,4a,5-triaza-fluorene;
(4R,9aR)-6-ethyl-7-methoxymethyl-4-methyl-3,4,9,9a-tetrahydro-1H-2,4a,5-triaza-fluorene;
(4R,9aR)-7-ethoxymethyl-6-ethyl-4-methyl-1,2,3,4,9,9a-hexahydro-2,4a,5-triaza-fluorene;
(4R,9aR)-7-cyclopropylmethoxymethyl-6-ethyl-4-methyl-1,2,3,4,9,9a-hexahydro-2,4a,5-triaza-fluorene;
(4R,9aR)-7-chloro-6-difluoromethyl-4-methyl-1,2,3,4,9,9a-hexahydro-2,4a,5-triaza-fluorene;
(4R,9aR)-7-bromo-6-difluoromethyl-4-methyl-1,2,3,4,9,9a-hexahydro-2,4a,5-triaza-fluorene;
(4R,9aR)-6-difluoromethyl-4,7-dimethyl-1,2,3,4,9,9a-hexahydro-2,4a,5-triaza-fluorene;
(4R,9aR)-6-difluoromethyl-7-methoxymethyl-4-methyl-1,2,3,4,9,9a-hexahydro-2,4a,5-triaza-fluorene;
(4R,9aR)-6-difluoromethyl-7-ethoxymethyl-4-methyl-1,2,3,4,9,9a-hexahydro-2,4a,5-triaza-fluorene;
(4R,9aR)-7-cyclopropylmethoxymethyl-6-difluoromethyl-4-methyl-1,2,3,4,9,9a-hexahydro-2,4a,5-triaza-fluorene;
(4R,9aR)-7-chloro-6-methoxy-4-methyl-1,2,3,4,9,9a-hexahydro-2,4a,5-triaza-fluorene;
(4R,9aR)-7-bromo-6-methoxy-4-methyl-1,2,3,4,9,9a-hexahydro-2,4a,5-triaza-fluorene;
(4R,9aR)-6-methoxy-4,7-dimethyl-1,2,3,4,9,9a-hexahydro-2,4a,5-triaza-fluorene;
(4R,9aR)-7-chloro-6-ethoxy-4-methyl-1,2,3,4,9,9a-hexahydro-2,4a,5-triaza-fluorene;
(4R,9aR)-7-bromo-6-ethoxy-4-methyl-1,2,3,4,9,9a-hexahydro-2,4a,5-triaza-fluorene;
(4R,9aR)-6-ethoxy-4,7-dimethyl-1,2,3,4,9,9a-hexahydro-2,4a,5-triaza-fluorene;
(4R,9aR)-7-chloro-6-ethoxymethyl-4-methyl-1,2,3,4,9,9a-hexahydro-2,4a,5-triaza-fluorene;
(4R,9aR)-7-bromo-6-ethoxymethyl-4-methyl-1,2,3,4,9,9a-hexahydro-2,4a,5-triaza-fluorene;
(4R,9aR)-6-ethoxymethyl-4,7-dimethyl-1,2,3,4,9,9a-hexahydro-2,4a,5-triaza-fluorene;
(4R,9aR)-7-chloro-6-cyclopropylmethoxymethyl-4-methyl-1,2,3,4,9,9a-hexahydro-2,4a,5-triaza-fluorene;
(4R,9aR)-7-bromo-6-cyclopropylmethoxymethyl-4-methyl-1,2,3,4,9,9a-hexahydro-2,4a,5-triaza-fluorene;
(4R,9aR)-6-cyclopropylmethoxymethyl-4,7-dimethyl-1,2,3,4,9,9a-hexahydro-2,4a,5-triaza-fluorene;
(4R,9aR)-6-cyclopropylmethoxymethyl-4-methyl-1,2,3,4,9,9a-hexahydro-2,4a,5-triaza-fluoren-7-ol;

(4R,9aR)-6-cyclopropylmethoxymethyl-7-methoxy-4-methyl-1,2,3,4,9,9a-hexahydro-2,4a,5-triaza-fluorene;
(4R,9aR)-6-cyclopropylmethoxymethyl-7-ethoxy-4-methyl-1,2,3,4,9,9a-hexahydro-2,4a,5-triaza-fluorene;
(4R,9aR)-7-ethanesulfonyl-4,6-dimethyl-1,2,3,4,9,9a-hexahydro-2,4a,5-triaza-fluorene;
(4R,9aR)-6-cyclopropylmethoxymethyl-7-ethoxymethyl-4-methyl-1,2,3,4,9,9a-hexahydro-2,4a,5-triaza-fluorene;
(4R,9aR)-7-chloro-6-(1-(R)-methoxy-ethyl)-4-methyl-1,2,3,4,9,9a-hexahydro-2,4a,5-triaza-fluorene;
(4R,9aR)-7-bromo-6-(1-(R)-methoxy-ethyl)-4-methyl-1,2,3,4,9,9a-hexahydro-2,4a,5-triaza-fluorene;
(4R,9aR)-6-(1-(R)-methoxy-ethyl)-4,7-dimethyl-1,2,3,4,9,9a-hexahydro-2,4a,5-triaza-fluorene;
(4R,9aR)-6-(1-(R)-methoxy-ethyl)-7-methoxymethyl-4-methyl-1,2,3,4,9,9a-hexahydro-2,4a,5-triaza-fluorene;
(4R,9aR)-7-chloro-6-(1-(S)-methoxy-ethyl)-4-methyl-1,2,3,4,9,9a-hexahydro-2,4a,5-triaza-fluorene;
(4R,9aR)-7-bromo-6-(1-(S)-methoxy-ethyl)-4-methyl-1,2,3,4,9,9a-hexahydro-2,4a,5-triaza-fluorene;
(4R,9aR)-6-(1-(S)-methoxy-ethyl)-4,7-dimethyl-1,2,3,4,9,9a-hexahydro-2,4a,5-triaza-fluorene;
(4R,9aR)-6-(1-(S)-methoxy-ethyl)-7-methoxymethyl-4-methyl-1,2,3,4,9,9a-hexahydro-2,4a,5-triaza-fluorene;
(R)-7-fluoro-4-methyl-1,2,3,4-tetrahydro-2,4a,5-triaza-fluorene;
(4R,9aR)-7-fluoro-4-methyl-1,2,3,4,9,9a-hexahydro-2,4a,5-triaza-fluorene;
(4R,9aR)-(7-fluoro-4-methyl-1,2,3,4,9,9a-hexahydro-2,4a,5-triaza-fluoren-6-yl)-methanol;
(4R,9aR)-6-cyclopropylmethoxymethyl-7-fluoro-4-methyl-1,2,3,4,9,9a-hexahydro-2,4a,5-triaza-fluorene;
(4R,9aR)-7-fluoro-4-methyl-1,2,3,4,9,9a-hexahydro-2,4a,5-triaza-fluorene-6-carbaldehyde O-methyl-oxime;
1-(S)-[(4R,9aR)-7-fluoro-4-methyl-1,2,3,4,9,9a-hexahydro-2,4a,5-triaza-fluoren-6-yl]-ethanol;
(4R,9aR)-6-(1-(S)-cyclopropylmethoxy-ethyl)-7-fluoro-4-methyl-1,2,3,4,9,9a-hexahydro-2,4a,5-triaza-fluorene;
(E)-[4R,9aR]-1-(7-fluoro-4-methyl-1,2,3,4,9,9a-hexahydro-2,4a,5-triaza-fluoren-6-yl)-ethanone O-methyl-oxime
(4R,9aR)-7-bromo-6-fluoromethyl-4-methyl-1,2,3,4,9,9a-hexahydro-2,4a,5-triaza-fluorene;
(4R,9aR)-6-Chloro-7-fluoro-4-methyl-1,2,3,4,9,9a-hexahydro-2,4a,5-triaza-fluorene
(4R,9aR)-6-fluoromethyl-7-iodo-4-methyl-1,2,3,4,9,9a-hexahydro-2,4a,5-triaza-fluorene;
(4R,9aR)-7-ethoxymethyl-6-fluoromethyl-4-methyl-1,2,3,4,9,9a-hexahydro-2,4a,5-triaza-fluorene;
(4R,9aR)-6-fluoromethyl-7-4-methoxyphenyl-4-methyl-1,2,3,4,9,9a-hexahydro-2,4a,5-triaza-fluorene;
(4R,9aR)-7-bromo-6-ethylsulfanyl-4-methyl-1,2,3,4,9,9a-hexahydro-2,4a,5-triaza-fluorene;
(4R,9aR)-7-bromo-6-propanesulfanyl-4-methyl-1,2,3,4,9,9a-hexahydro-1H-2,4a,5-triaza-fluorene;
(4R,9aR)-1-(RS)-(7-iodo-4-methyl-1,2,3,4,9,9a-hexahydro-2,4a,5-triaza-fluoren-6-yl)-1-ethanol;
(4R,9aR)-7-ethoxy-4-methyl-1,2,3,4,9,9a-hexahydro-2,4a,5-triaza-fluorene;
(4R,9aR)-4,7-dimethyl-1,2,3,4,9,9a-hexahydro-2,4a,5-triaza-fluorene;
(4R,9aR)-7-ethyl-4-methyl-1,2,3,4,9,9a-hexahydro-2,4a,5-triaza-fluorene;
(4R,9aR)-7-bromo-4-methyl-1,2,3,4,9,9a-hexahydro-2,4a,5-triaza-fluorene;
(4R,9aR)-7-chloro-4-methyl-1,2,3,4,9,9a-hexahydro-2,4a,5-triaza-fluorene;
(4R,9aR)-7-iodo-4-methyl-1,2,3,4,9,9a-hexahydro-2,4a,5-triaza-fluorene;
(4R,9aR)-7-ethoxymethyl-4-methyl-1,2,3,4,9,9a-hexahydro-2,4a,5-triaza-fluorene;
(4R,9aR)-7-benzyloxymethyl-4-methyl-1,2,3,4,9,9a-hexahydro-2,4a,5-triaza-fluorene;
(4R,9aR)-7-methoxymethyl-4-methyl-1,2,3,4,9,9a-hexahydro-2,4a,5-triaza-fluorene;
(4R,9aR)-7-cyclopropylmethoxy-4-methyl-1,2,3,4,9,9a-hexahydro-2,4a,5-triaza-fluorene;
(4R,9aR)-7-fluoro-4,8-dimethyl-1,2,3,4,9,9a-hexahydro-2,4a,5-triaza-fluorene;
(4R,9aR)-(7-fluoro-4-methyl-1,2,3,4,9,9a-hexahydro-2,4a,5-triaza-fluoren-8-yl)-methanol;
(4R,9aR)-7-fluoro-8-methoxymethyl-4-methyl-1,2,3,4,9,9a-hexahydro-2,4a,5-triaza-fluorene;
(4R,9aR)-7-fluoro-4-methyl-1,2,3,4,9,9a-hexahydro-2,4a,5-triaza-fluorene-8-carbaldehyde oxime; and
(4R,9aR)-7-fluoro-4-methyl-1,2,3,4,9,9a-hexahydro-2,4a,5-triaza-fluorene-8-carbaldehyde O-methyl-oxime.

Examples of particularly preferred compounds of formula I are:
(4R,9aR)-7-ethoxy-4,6-dimethyl-1,2,3,4,9,9a-hexahydro-2,4a,5-triaza-fluorene;
(4R,9aR)-7-(2-methoxy-ethoxy)-4,6-dimethyl-1,2,3,4,9,9a-hexahydro-2,4a,5-triaza-fluorene;
(4R,9aR)-4,6,7-trimethyl-1,2,3,4,9,9a-hexahydro-2,4a,5-triaza-fluorene;
(4R,9aR)-7-fluoro-4-methyl-1,2,3,4,9,9a-hexahydro-2,4a,5-triaza-fluorene;
(4R,9aR)-6-cyclopropylmethoxymethyl-7-fluoro-4-methyl-1,2,3,4,9,9a-hexahydro-2,4a,5-triaza-fluorene;
1-(S)-[(4R,9aR)-7-fluoro-4-methyl-1,2,3,4,9,9a-hexahydro-2,4a,5-triaza-fluoren-6-yl]-ethanol and
(4R,9aR)-6-(1-(S)-cyclopropylmethoxy-ethyl)-7-fluoro-4-methyl-1,2,3,4,9,9a-hexahydro-2,4a,5-triaza-fluorene.

Processes for the manufacture of the compounds according to formula I are an object of the present invention. The substituents and indices used in the following schemes have the significance given above unless indicated to the contrary.

Hydroxy groups can be protected in the following reactions by methods known in the art such as for example tert-butyl-dimethylsilyl.

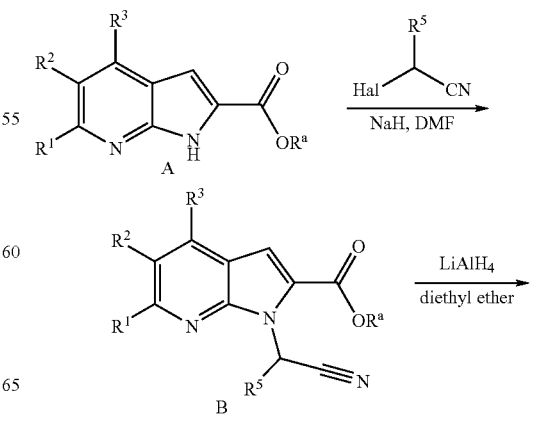

Scheme 1

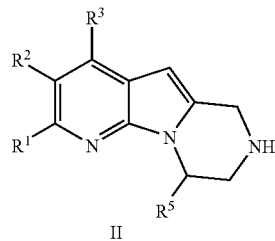

II 1,2,3,4-Tetrahydro[2,4a,5]triaza-fluorenes of formula II can be prepared according to scheme 1 by a process where the 7-aza-indole-2-carboxylate of formula A is first reacted with an alpha halo alkanenitrile (e.g. 2-bromo propionitrile) in a suitable solvent (e.g. N,N-dimethylformamide) with a suitable base (e.g. sodium hydride). Compounds of formula II correspond to compounds of formula I, wherein $R^4$ is hydrogen.

The intermediate B is reduced and cyclized to the tetrahydro[2,4a,5]triaza-fluorene II by reaction with a suitable reducing agent in a suitable solvent (e.g. LiAlH$_4$ in tetrahydrofuran or diethyl ether). $R^a$ in scheme 1 is an alkyl group, preferably a lower alkyl group, preferably methyl or ethyl.

Preparation of compounds according to formula A:

Compounds of formula A, wherein $R^1$ is hydrogen or halogen, particularly chlorine and $R^2$ is hydrogen, particularly chlorine and $R^3$ is hydrogen are described in WO 0044753.

Compounds of formula A, wherein $R^1$, $R^2$ and $R^3$ are defined as before with the proviso that $R^1$ and $R^2$ is are not hydrogen can be obtained by an analogous process as described in WO 0044753 by, e.g. oxidation of the pyridine nitrogen to the N-oxide under appropriate oxidizing conditions, such as meta-chloroperoxybenzoic acid in dichloromethane and treatment of the N-oxide with a nucleophilic system, such as neat acetic acid anhydride or benzoic acid bromide in the presence of a suitable base, like e.g. hexamethyldisilazane in a suitable solvent such as, e.g. tetrahydrofuran. The indole nitrogen can be optionally protected in this process, preferably with a Boc group.

Compound of formula A, wherein $R^1$, $R^2$ and $R^3$ are as defined before with the proviso that $R^1$, $R^2$ and $R^3$ are not halogen can also be obtained by analogous process as described in Synthesis 1996, 877 from N-protected (preferably Boc) 3-alkyl-2-aminopyridines, through double deprotonation with a base, such as n-butyllithium in a suitable solvent like, e.g. tetrahydrofuran and subsequent treatment of the intermediate with diethyloxalate and dehydration of the resulting adduct under acidic conditions, e.g. with hydrochloric acid in an appropriate alcohol, such as, e.g. ethanol.

Alpha halo alkanenitriles can be either purchased from commercial sources or synthesized from, e.g. reaction of acrylonitrile with bromoalkanes under UV irradiation in the presence of, e.g. triphenylphosphine and a suitable catalyst such as copper(I)chloride in an appropriate solvent like, e.g. tetrahydrofuran (analogous to the process described in J. Am. Chem. Soc. 1983, 105(22), 6719). Alpha halo alkanenitriles can also be prepared in a process, where an alkoxyacetonitrile derivative is irradiated in the presence of a suitable brominating agent like, e.g. N-bromosuccinimide in tetrahydrofuran (analogous to the process described in J. Org. Chem. 1976, 14 (17), 2846). In the case where $R^5$ is hydroxymethyl the free OH is protected.

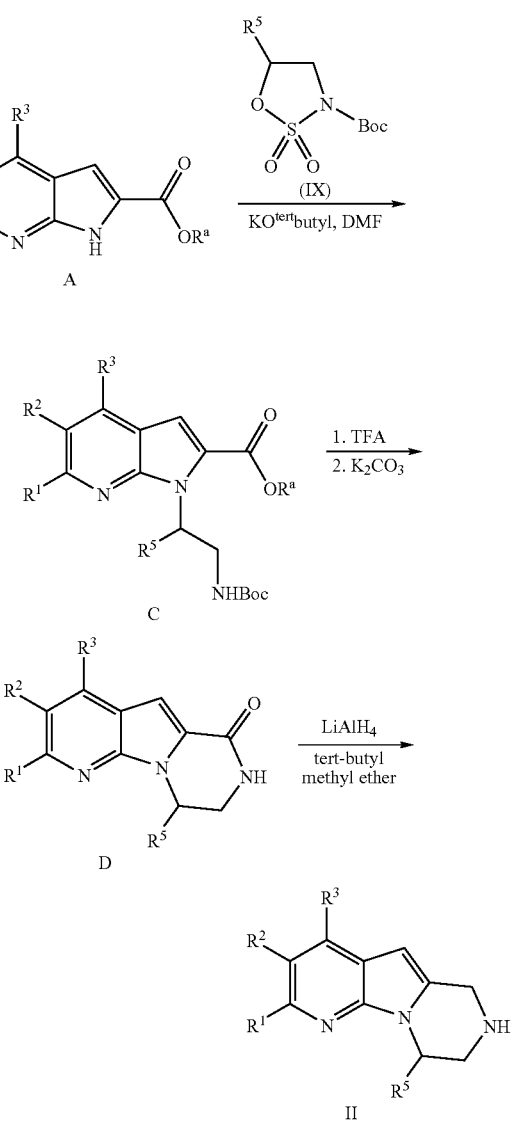

1,2,3,4-Tetrahydro[2,4a,5]triaza-fluorenes of formula II can also be prepared according to scheme 2 by a process where the 7-aza-indole-2-carboxylate of formula A is first reacted with the Boc-sulfamidate IX in a suitable solvent (e.g. N,N-dimethylformamide) with a suitable base (e.g. potassium tert-butylate or sodium hydride) followed by removal of the Boc protecting group (Boc means tert-butoxycarbonyl) with a suitable reagent e.g. trifluoroacetic acid (TFA) and ring closure in the presence of base (e.g. potassium carbonate). The stereochemistry of the carbon atom attached to $R^5$ in Boc-sulfamidate IX is inverted (>90% e.e.) in this reaction sequence. The intermediate amide D is reduced with a suitable reducing agent in a suitable solvent (e.g. LiAlH$_4$ in tert-butyl methyl ether or borane-dimethylsulfide complex in tetrahydrofuran). $R^a$ in scheme 2 is an alkyl group, preferably a lower alkyl group, preferably methyl or ethyl. Compounds II are defined as in scheme 1.

Chiral compounds according to formula II can e.g. be obtained as follows:

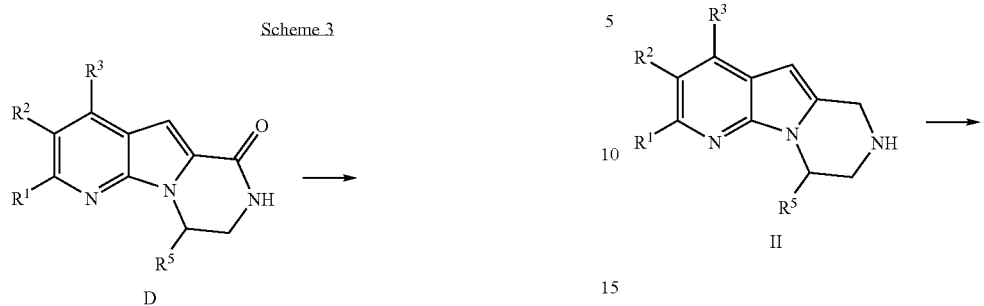

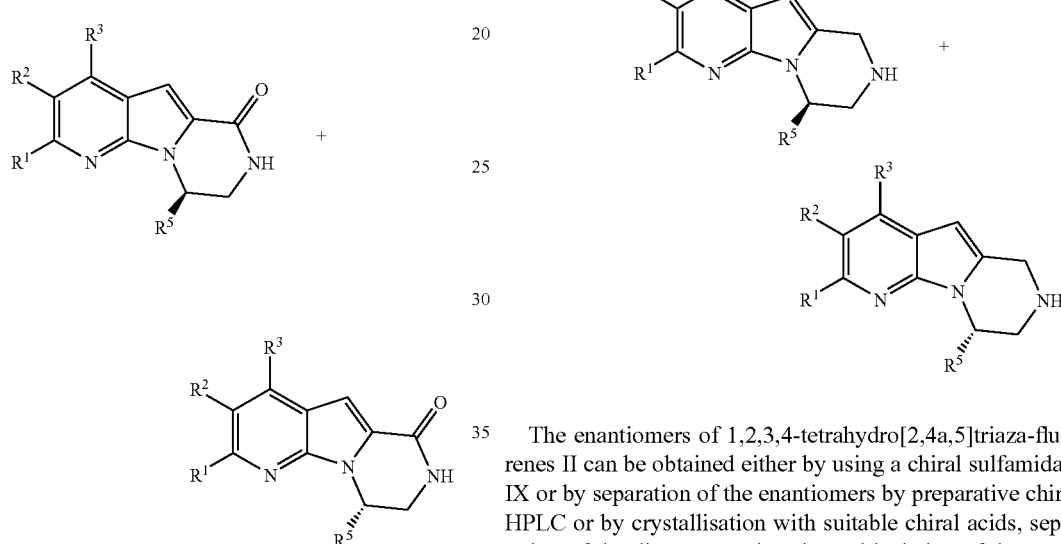

If racemic Boc-sulfamidate IX is used in this process, the enantiomers of intermediate D can be obtained by methods known in the art, e.g. by preparative chiral HPLC.

The enantiomers of 1,2,3,4-tetrahydro[2,4a,5]triaza-fluorenes II can be obtained either by using a chiral sulfamidate IX or by separation of the enantiomers by preparative chiral HPLC or by crystallisation with suitable chiral acids, separation of the diastereomeric salts and isolation of the enantiomers from these salts. An alternative access to the enantiomers of 1,2,3,4-tetrahydro[2,4a,5]triaza-fluorenes II involves the separation of the enantiomers of the precursor C, e.g. by preparative chiral HPLC.

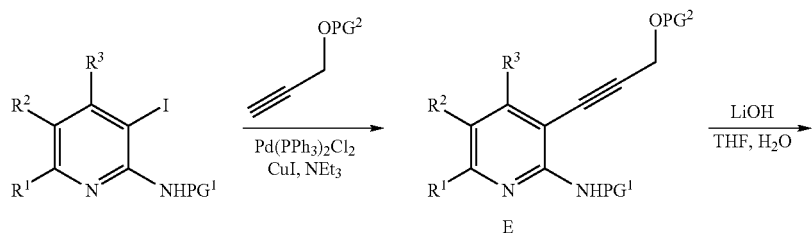

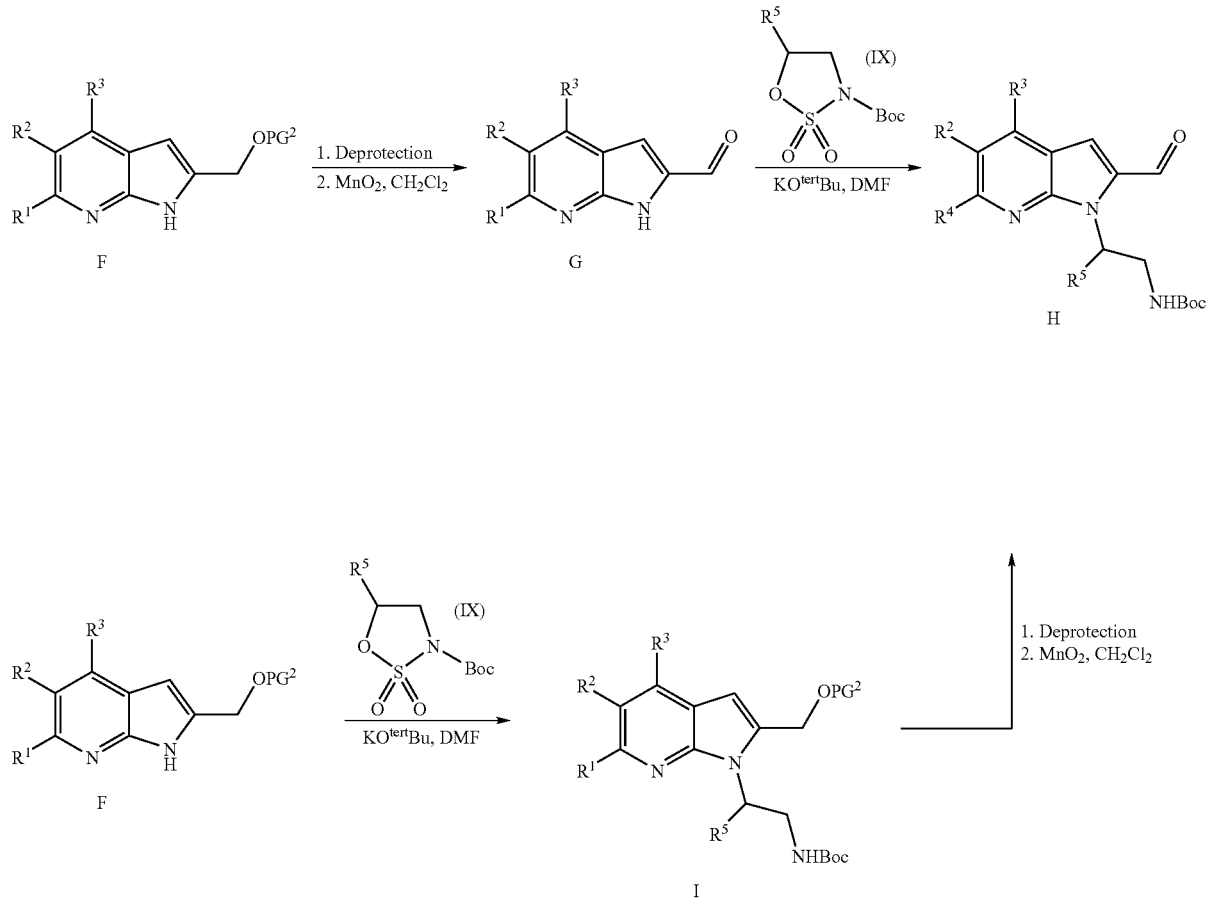

7-Aza-indole derivatives H can be prepared according to scheme 5, starting from optionally protected o-iodoanilines 2-amino-3-iodopyridines (PG$^1$ means a suitable protective group such as e.g. N-methoxycarbonyl) by cross-coupling reaction with suitably substituted and optionally protected carbinols (preferred protective groups PG$^2$ are silyl ethers, especially preferred is tert-butyl-dimethylsilyl). The reaction proceeds in the presence of a suitable catalyst (e.g. bis(-triphenylphosphine) palladium dichloride and copper(I)iodide as co-catalyst) in a suitable solvent (e.g. triethylamine). The intermediate E is treated with a base (e.g. LiOH in tetrahydrofuran/water) to yield the indole derivative F. Alternatively, if the amine in intermediate E is unprotected (PG$^1$ is hydrogen), intermediate F can be obtained by treatment of the intermediate E with trifluoroacetic acid anhydride followed by reaction with a suitable catalyst such as e.g. palladium(II)acetate and heating the reaction mixture in an appropriate solvent (e.g. triethylamine). After deprotection (e.g. with tetrabutylammonium fluoride) in a suitable solvent (e.g. tetrahydrofuran), the resulting alcohol is oxidized (e.g., with manganese dioxide in dichloromethane), to yield the indole derivative G. Alkylation of G with the Boc-sulfamidate X in a suitable solvent (e.g. N,N-dimethylformamide) in the presence of a suitable base (e.g. sodium hydride or potassium tert-butylate) leads to intermediate H. The stereochemistry of the carbon atom attached to R$^5$ in Boc-sulfamidate IX is inverted (>90% e.e.) in this reaction sequence. Alternatively, the intermediate F can be subjected to alkylation with the Boc-sulfamidate IX under similar conditions as mentioned above for the conversion of G to H, to furnish intermediate I which can be converted to intermediate H by deprotection and oxidation as mentioned in the conversion of F to G.

Alternatively, compounds of formula H can be prepared according to scheme 6:

Scheme 6

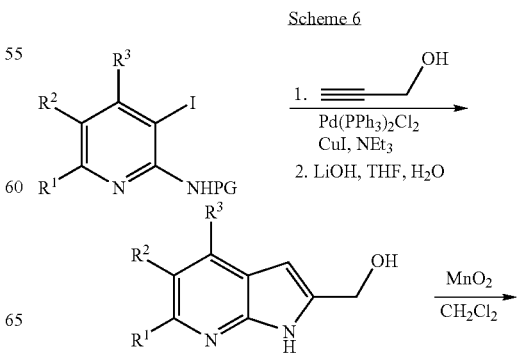

-continued

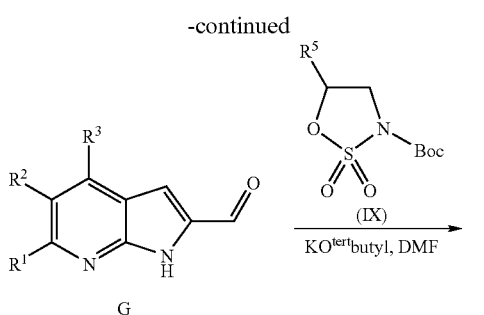
G

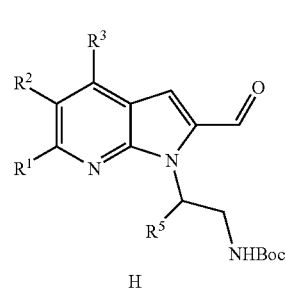
H

7-Aza-indole derivatives H can also be prepared according to scheme 6, starting from protected o-iodoanilines (a suitable protective group, PG, is, e.g. N-methoxycarbonyl) by cross-coupling reaction with propargyl alcohol derivatives in the presence of a suitable catalyst (e.g. bis-triphenylphosphine palladium dichloride and copper(I)iodide as co-catalyst) in a suitable solvent (e.g. triethylamine), followed by treatment with a base (e.g. LiOH in tetrahydrofuran/water). The alcohol intermediate is oxidized, e.g. with manganese dioxide in dichloromethane, to yield the indole derivative G. Alkylation of G with the Boc-sulfamidate IX in a suitable solvent (e.g. N,N-dimethylformamide) in the presence of a suitable base (e.g. potassium tert-butylate or sodium hydride) leads to intermediate H. The stereochemistry of the carbon atom attached to $R^5$ in Boc-sulfamidate IX is inverted (>90% e.e.) in this reaction sequence.

Scheme 7

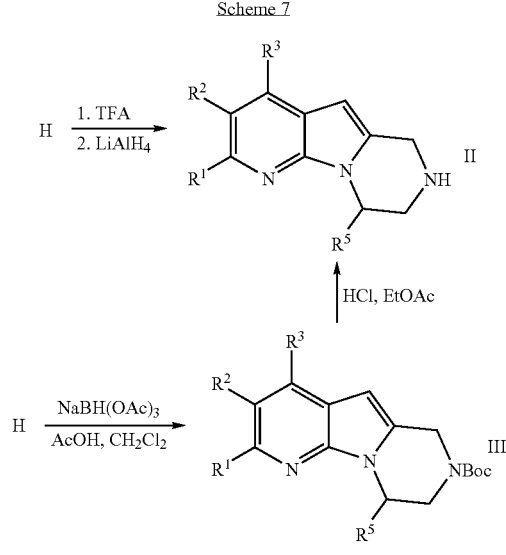

As described in scheme 7, the intermediates of formula H can be further processed to compounds of formula II by either removal of the Boc protecting group (e.g., with trifluoroacetic acid) to yield an imine intermediate which is not isolated but reduced directly with lithium aluminium hydride to yield II as a separable mixture of epimers, or by direct reductive amination (e.g. with sodium triacetoxyborohydride, molecular sieves and acetic acid in a suitable solvent, e.g. dichloromethane) to yield compound III, followed by removal of the protecting group (e.g. with hydrochloric acid in ethyl acetate).

Scheme 8

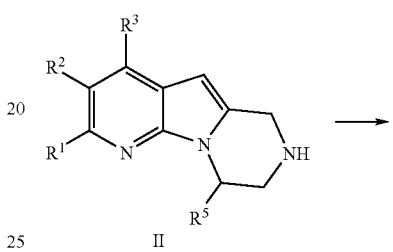
II

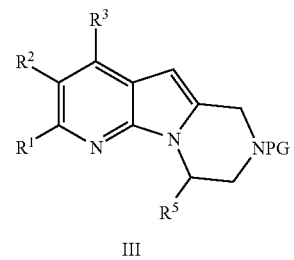
III

A variety of substituents $R^1$, $R^2$ and $R^3$, preferably those functional groups that do not tolerate the methods described for the 1,2,3,4-tetrahydro[2,4a,5]triaza-fluorenes synthesis can be introduced starting from 1,2,3,4-tetrahydro[2,4a,5] triaza-fluorene II according to scheme 8. To that end, the amine nitrogen of II may be protected, e.g., as the tert-butyl carbamate, to generate compounds of formula III.

Scheme 9

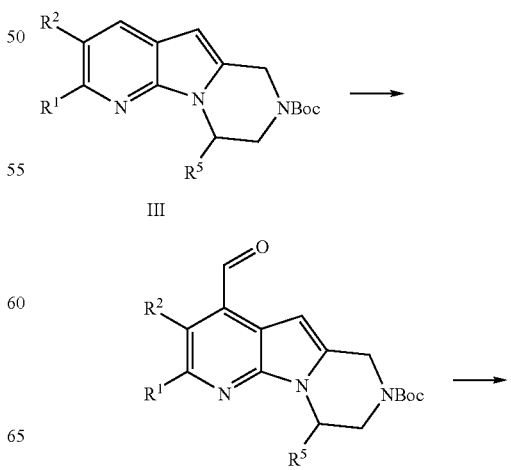

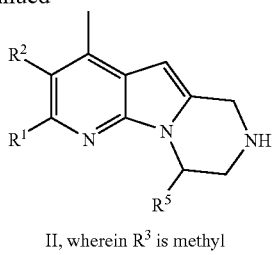

II, wherein R³ is methyl 1,2,3,4-Tetrahydro[2,4a,5]triaza-fluorenes of formula II in which R³ equals a methyl substituent can also be prepared as depicted in scheme 9 from intermediate III by a two step process where an aldehyde moiety is first introduced by, e.g. a Vilsmeier-Haack formylation reaction and subsequent reduction of the formyl intermediate under suitable conditions (e. g., triethylsilane and trifluoroacetic acid in dichloromethane). Under these conditions the protective group may also be cleaved-off, e.g. if it is a tert-butyl carbamate group.

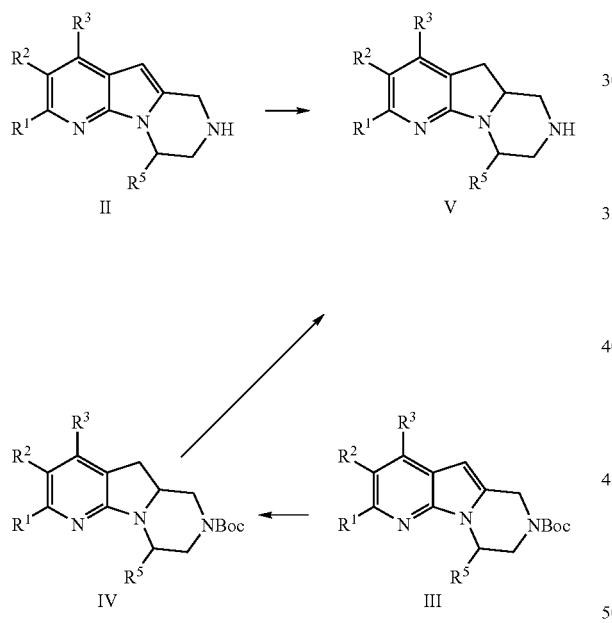

The hexahydro[2,4a,5]triaza-fluorene derivatives of formula V can be prepared as described in scheme 10 from compounds of formula II (analogous to WO 0044753) by reduction with suitable reducing agents in suitable solvents or solvent mixtures (e.g. sodium borohydride in tetrahydrofuran/TFA or NaCNBH₃ in acetic acid, respectively). Compounds of formula V may also be prepared from compounds of formula III (analogous to WO 0044753) by either simultaneous reduction and deprotection of the tert-butoxy carbonyl group with suitable reducing agents in suitable acidic solvents or solvent mixtures (e.g. tetrahydrofuran/TFA) or via removal of the protecting group from intermediates IV, which in turn can be obtained by reduction of intermediates III with a suitable reducing agent in an appropriate solvent (e.g. sodium cyanoborohydride in e.g. acetic acid).

Compounds of formula Ia can be prepared as shown in scheme 11:

Scheme 11

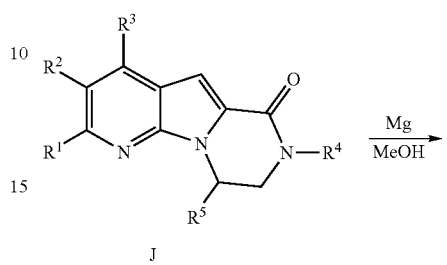

J

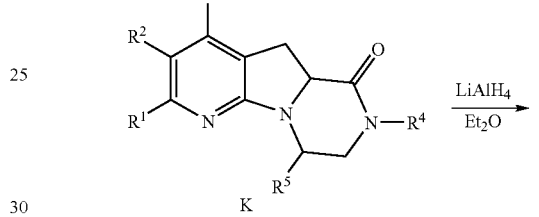

K

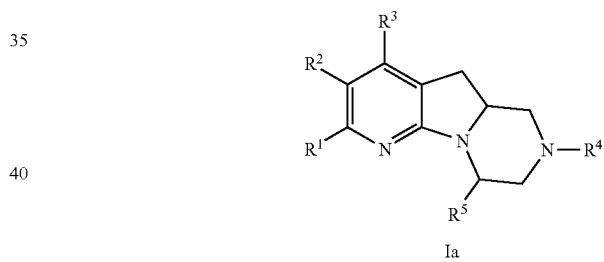

Ia

Hexahydro[2,4a,5]triaza-fluorene derivatives of formula Ia with the proviso that R¹, R² and R³ are not bromine can also be prepared as depicted in scheme 11 from intermediate J where the indole moiety is reduced with magnesium in methanol to produce indoline-amide K, which is then reduced under suitable conditions (e.g., LiAlH₄ in diethyl ether). Compound J can be obtained according to Scheme 2 (R⁴ is hydrogen). In case R⁴ is alkyl compound J can be obtained e.g. by reaction of compound D with alkyl-Br under basic conditions.

Scheme 12

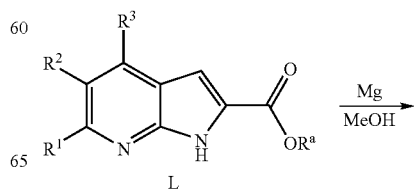

L

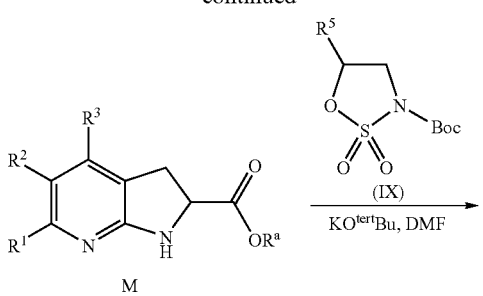

M

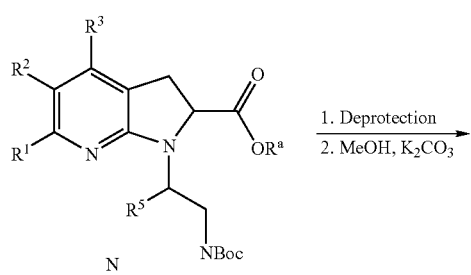

N

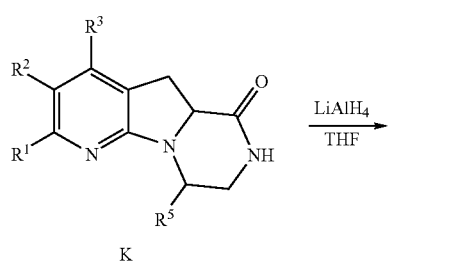

K

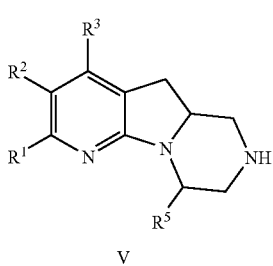

V

Compounds V with the proviso that $R^1$, $R^2$ and $R^3$ are not bromine can alternatively be prepared as depicted in scheme 12. Indole intermediates L are reduced with a suitable reducing agent (e.g. magnesium in methanol). The indoline derivative M is alkylated with an alkylating agent such as, e.g. the sulfamidate IX in the presence of a suitable base like, e.g. sodium hydride in a suitable solvent such as N,N-dimethylformamide. Intermediate K can be prepared by sequential treatment of intermediate N with an acid (e.g. trifluoroacetic acid in dichloromethane) followed by a base like, e.g. potassium carbonate in methanol. Reduction of intermediate K with a suitable reducing agent such as lithium aluminium hydride in a suitable solvent such as, e.g. tetrahydrofuran or diethyl ether yields derivatives V.

Scheme 13

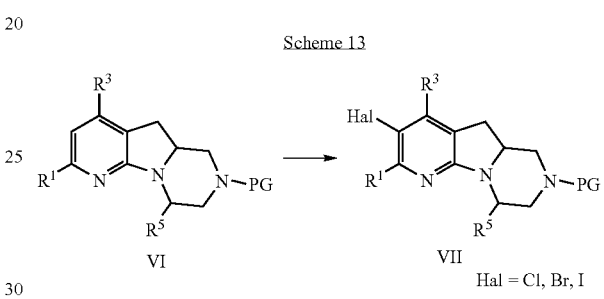

Intermediates of formula IV can be prepared according to scheme 13 from intermediates VII by methods known to those skilled in the art. Intermediates VII in turn can be obtained by halogenation of intermediates VI with a suitable halogenating agent (e.g. for Hal=Br with N-bromosuccinimide) in a suitable solvent such as, e.g. tetrahydrofuran.

Intermediates IV in which $R^1$ and $R^2$ are defined as above and $R^3$ equals hydrogen can also be obtained from intermediates VII in which $R^1$ and $R^2$ are defined as above and $R^3$ equals hydrogen in analogy to scheme 13 by using intermediates P-S and W which can be synthesized according to schemes 14 and 15 using the hexahydro[2,4a,5]triaza-fluorene derivative VIII as starting material.

Intermediate VIII can be obtained according to scheme 2 and following reduction according to scheme 10.

Scheme 14

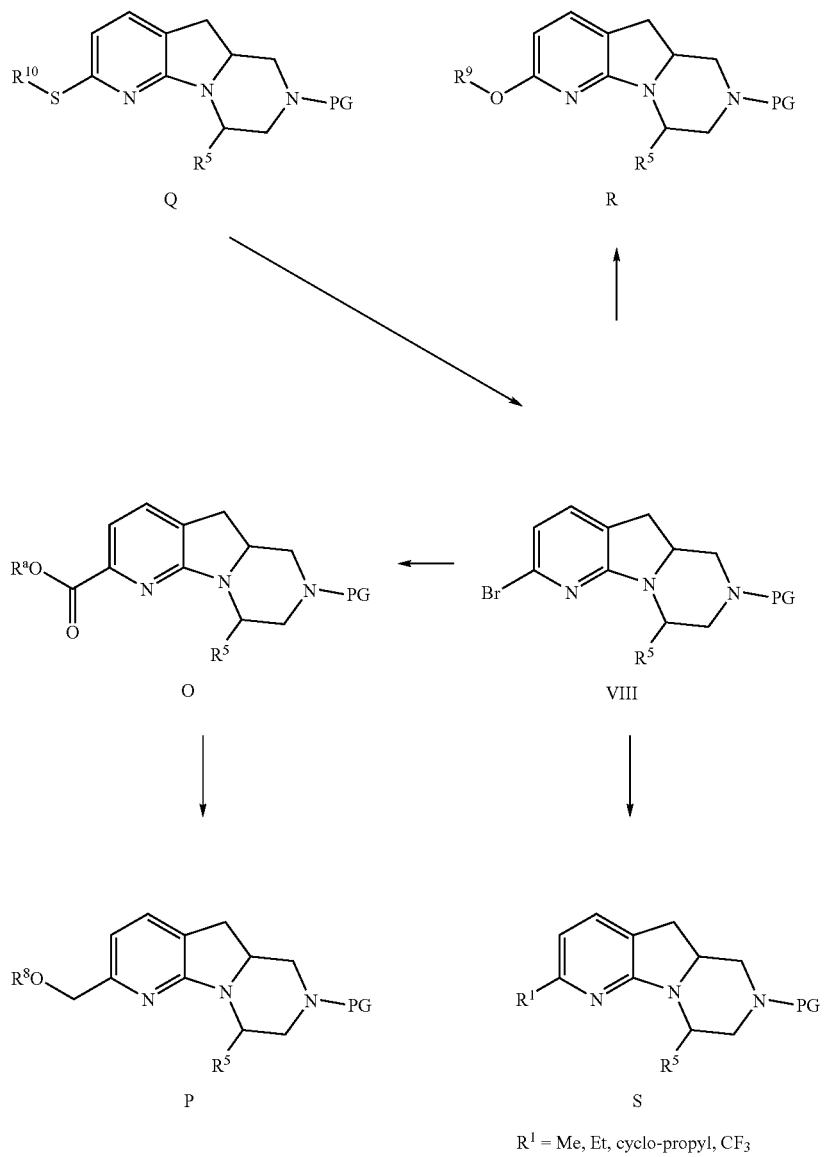

R¹ = Me, Et, cyclo-propyl, CF₃

PG means a protective group compatible with the chemical transformation, e.g. as described in T. W. Greene and P. G. M. Wuts, Protective groups in organic synthesis, 2nd edition, pp. 309; preferably Boc.

$R^a$ is defined as before and $R^8$, $R^9$ and $R^{10}$ is alkyl, aryl, cycloalkyl, alkoxyalkyl or aryloxyalkyl.

Compounds according to formula VIII can be obtained according to scheme 2 and following reduction according to scheme 10.

Several examples for the elaboration of compound VIII are highlighted in schemes 14 and 15.

Alkyl/Aryloxy-substituted derivatives P can be obtained from ester-substituted intermediates O (e.g. via bromine-lithium exchange, quenching the lithium intermediate with carbon dioxide and esterification of the acid) or via carbonylation reactions (e.g. under a carbon monoxide atmosphere with a suitable catalyst like, e.g. bis(triphenylphosphine)palladium(II) chloride in an appropriate alcohol like, e.g. methanol or ethanol in the presence of a base like, e.g. triethylamine). Intermediates O are reduced to benzylic alcohols (P, $R^8$=H), the latter again can be alkylated or arylated by methods known to those skilled in the art.

Alkyl, trifluoromethyl, or cyclopropyl derivatives S (for example, a methyl group can be introduced through cross-coupling reaction with trimethylboroxine in the presence of a catalyst like, e.g. tetrakis(triphenylphosphine)palladium(0) and an appropriate base like, e.g. sodium carbonate in a solvent mixture like, e.g. dimethoxyethane and water. A trifluoromethyl substituent can be introduced through reaction of intermediate VIII with, e.g. trifluoroacetate and copper(I)iodide in an appropriate solvent like, e.g. 1-methyl-2-pyrrolidone. A cyclopropyl substituent can be introduced for example through palladium-catalyzed (e.g. tetrakis (triphenylphosphine)palladium(0)) reaction of VIII with a pre-formed complex of 9-borabicyclo[3.3.1]nonane and pro-pargylbromide in the presence of an appropriate base like, e.g. sodium hydroxide in an appropriate solvent like, e.g. tetrahydrofuran.

Alkylsulfanyl derivatives Q. Procedures describing the metallation of aryl bromides and reaction with alkyl disulfides to form alkylsulfanyl derivatives are provided in *Heterocycles,* 1992, 34, 1169–1175.

Alkoxy derivatives R. Intermediate VIII is reacted with an suitable alcohol in a solvent like, e.g. toluene in the presence of an appropriate catalyst system such as, e.g. (S)-TOL-BINAP and Pd(dba)$_3$ and a base such as, e.g. sodium hydride.

reaction with an amide such as an N,N-dialkylamide e.g. dimethyl acetamide or an N-alkoxy-N-alkylamide such as N-methyl-N-methoxyacetamide. Alternatively, reaction of an organometallic or metal hydride reagent e.g. a Grignard reagent, organo-lithium reagent or di-isobutylaluminium hydride with the amide T (preferably $R^3$=methyl, $R^{14}$=methoxy) can also provide the ketone U. The alcohol V, where $R^{12}$ is defined as alkyl can be obtained from the ketone U by reaction with an organometallic reagent e.g. a Grignard reagent or organo-lithium reagent. The alcohol V, where $R^{12}$ is defined as hydrogen can be obtained from the ketone U by treatment with a reducing agent e.g. sodium borohydride. For alcohols of formula V where $R^{11} \neq R^{12}$, the enantiomers may be separated by methods known to those skilled in the art e.g. HPLC, optionally using a chiral column. Alternatively, homochiral alcohols of formula V

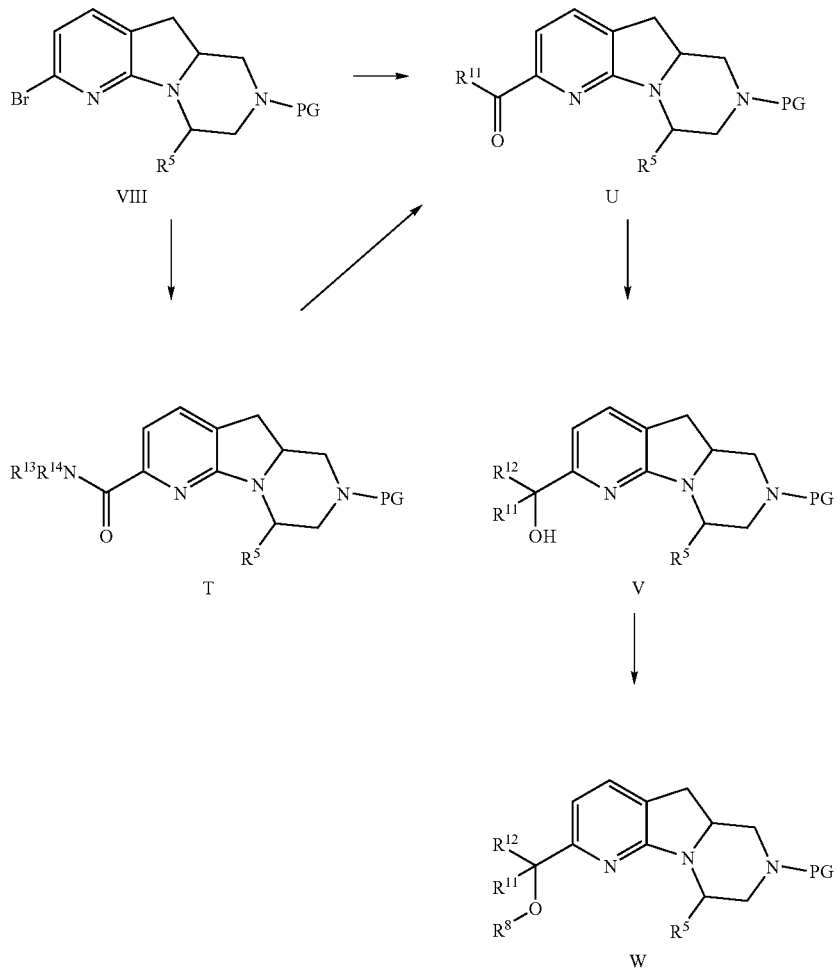

Scheme 15

Intermediates of formula W can be prepared according to scheme 15. Formation of the ketone U (aldehyde if $R^{11}$ equals hydrogen), where $R^{11}$ is defined as hydrogen, haloalkyl, alkoxyalkyl, thiazolyl or alkyl, preferably lower alkyl can be accomplished directly from the the bromide VIII by metallation with e.g. tertiary-butyllithium in a suitable solvent, e.g. tetrahydrofuran or diethyl ether, and where $R^{11} \neq R^{12}$ may be obtained directly from the ketone U according to known procedures e.g. *J. Am. Chem. Soc.,* 1987, 109(18), 5551–5553 and *ibid,* 1987, 109(25), 7925–7926.

Ethers of formula W where $R^8$ is defined as before may be obtained from the alcohol V according to methods known to those skilled in the art.

Scheme 16

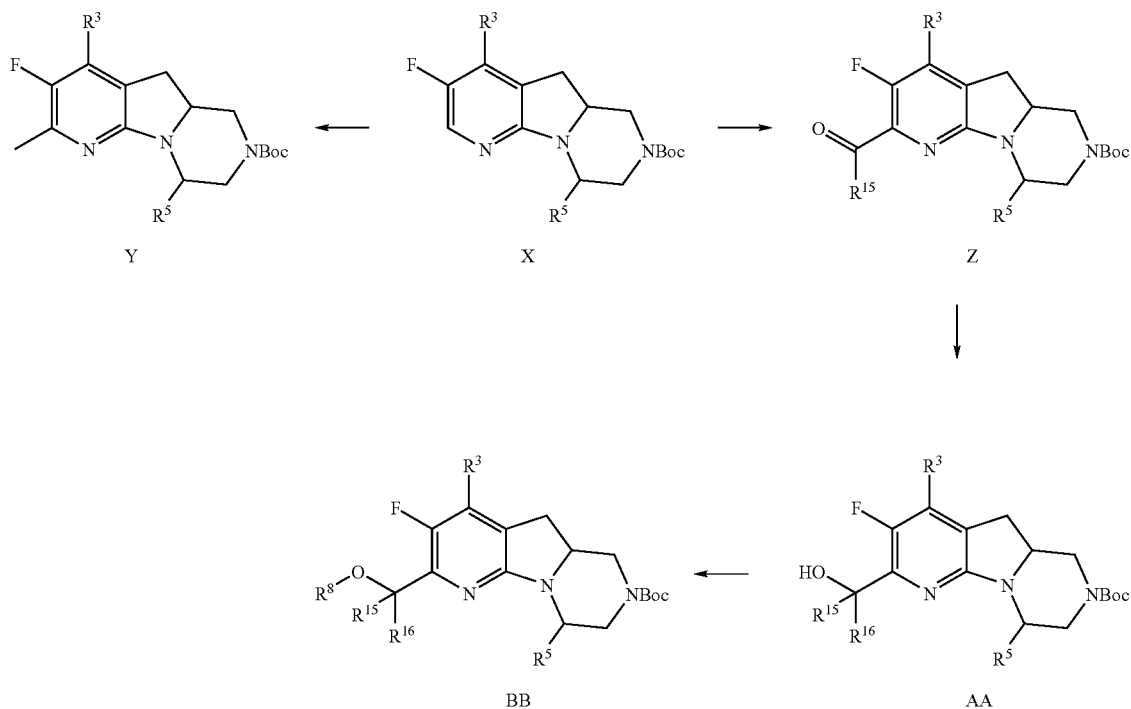

The intermediate X can be deprotonated by suitable bases (such as alkyl lithium in particular sec-butyl lithium) in a inert solvent such as toluene and reacted with electrophiles such as methyl iodide to furnish intermediate Y, or with dimethylformamide or dimethylacetamide to furnish intermediates Z ($R^{15}$ =H or $CH_3$). As mentioned in scheme 15, intermediates Z can by converted to alcohols AA and further converted to BB according to procedures described in scheme 15 above. For alcohols of formula AA where $R^{15} \neq R^{16}$, the enantiomers may be separated by methods known to those skilled in the art e.g. HPLC, optionally using a chiral column. Alternatively, homochiral alcohols of formula AA where $R^{15} \neq R^{16}$ may be obtained directly from the ketone Z according to known procedures e.g. *J. Am. Chem. Soc.*, 1987, 109(18), 5551–5553 and *ibid*, 1987, 109(25), 7925–7926.

-continued

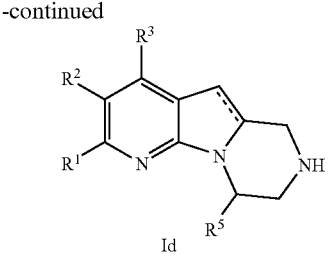

Id

Cleavage of the protective group in compounds according to formula Ic, wherein PG means a protecting group, preferably Boc, can be performed, e.g. with acid such as trifluoroacetic acid or hydrogen chloride in a suitable solvent such as ethyl acetate in order to obtain a compound of formula Id.

Scheme 17

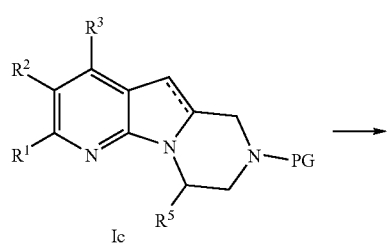

Ic

Scheme 18

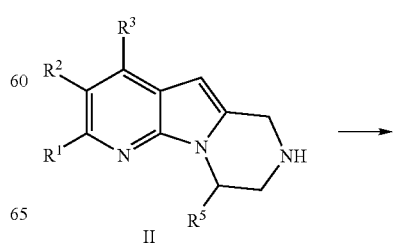

II

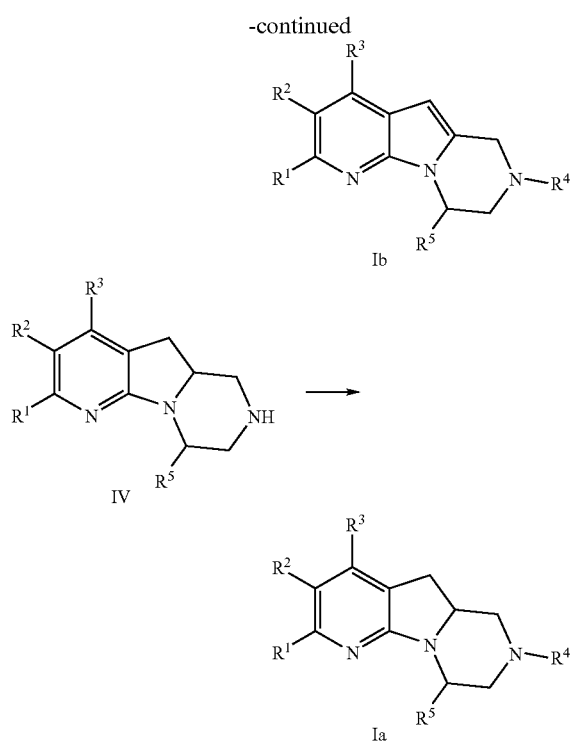

The tetra- and hexahydro[2,4a,5]triaza-fluorenes of formula Ib and Ia can be prepared from compounds of formula II and IV, respectively, by methods known in the art (e.g. March, Advanced Organic Chemistry, 4 th. edition, page 411ff, 768ff, 898ff, 900ff, 1212ff.), e.g. alkylation reactions (e.g. with $R^4$—Br under basic conditions), Mannich reactions or acylation followed by reduction etc.

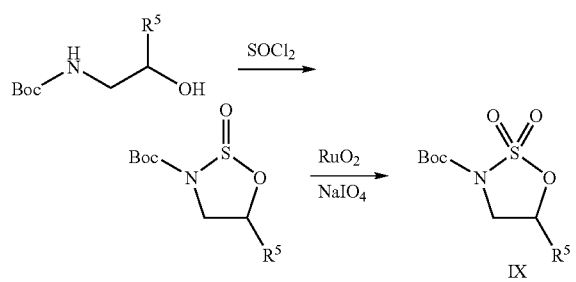

The Boc-sulfamidate IX can be prepared according to scheme 19 by treating Boc-protected ethanolamine derivatives with thionyl chloride in a suitable solvent e.g. tetrahydrofuran or ethyl acetate in the presence of a suitable base e.g. triethylamine or imidazole and oxidising the intermediate (e.g. with sodium metaperiodate and ruthenium(IV) oxide) in a suitable solvent (e.g. ethyl acetate). Where $R^5$ is not hydrogen, the stereochemistry of the carbon atom attached to $R^5$ remains unchanged (e.e. >97%) over this sequence.

It is a further object of the invention to provide compounds according to formula I for use as therapeutically active substances.

It is another object of the invention to provide compounds of formula I as described above for the production of medicaments for the prophylaxis and therapy of illnesses which are caused by disorders associated with the 5-HT$_2$ receptors, the 5-HT$_{2A}$, 5-HT$_{2B}$ and 5-HT$_{2C}$ subtypes, particularly the 5-HT$_{2C}$ subtype.

Likewise it is an object of the invention to provide pharmaceutical compositions comprising a compound of formula I and a therapeutically inert carrier.

It is a further object of the invention to provide a compound in accordance with formula I for use in the production of medicaments for the treatment and prophylaxis of eating disorders and obesity.

Also preferred is the use of a compound in accordance with formula I for the production of medicaments for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance.

Particularly preferred is the use of a compound in accordance with formula I for the production of medicaments for the treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance.

It is a further particularly preferred object of the invention to provide a compound in accordance with formula I for use in the production of medicaments for the treatment of Type II diabetes (non-insulin dependent diabetes mellitus (NIDDM)).

An object of the invention is the use of compounds in accordance with formula I for the production of medicaments for the treatment and prophylaxis of disorders of the central nervous system, cardiovascular disorders, gastrointestinal disorders, diabetes insipidus and sleep apnoea.

Particularly an object of the invention is the above use, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

A further preferred embodiment of the present invention is the above mentioned use of the compounds according to formula I, wherein the cardiovascular disorder is thrombosis.

Also preferred is the aforementioned use of the compounds according to formula I, wherein the gastrointestinal disorder is dysfunction of gastrointestinal motility.

A further object of the invention are compounds in accordance with formula I, when manufactured according to the processess described herein.

A further embodiment of the present invention is a method for the treatment and prophylaxis of disorders of the central nervous system, cardiovascular disorders, gastrointestinal disorders, diabetes insipidus and sleep apnoea, which method comprises administering an effective amount of a compound of formula I as described.

Preferred is this method, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

A further object of the present invention is the method for the treatment and prophylaxis of sexual dysfunction which method comprises administering an effective amount of a compound of formula I as described.

Preferred is a method for the treatment and prophylaxis of of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), diabetes insipidus, hyperglycemia, diabetic complications and insulin resistance, which method comprises administering an effective amount of a compound in accordance with formula I.

Particularly preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), hyperglycemia, diabetic complications and insulin resistance, which method comprises administering an effective amount of a compound in accordance with formula I.

It is a preferred object of the invention to provide a method for the treatment and prophylaxis of eating disorders and obesity, which method comprises administering an effective amount of a compound of formula I.

It is a preferred object of the invention to provide a method for the treatment and prophylaxis of Type II diabetes (non-insulin dependent diabetes mellitus (NIDDM), which method comprises administering an effective amount of a compound of formula I.

It is a further preferred object of the invention to provide a method of treatment of obesity in a human which comprises administration of a therapeutically effective amount of a compound according to formula I and a therapeutically effective amount of a lipase inhibitor, particularly, wherein the lipase inhibitor is orlistat. Also an object of the invention is the method as described above for the simultaneous, separate or sequential administration.

It is a further preferred object to provide a method of treatment of Type II diabetes (non-insulin dependent diabetes mellitus (NIDDM) in a human which comprises administration of a therapeutically effective amount of a compound according to formula I and a therapeutically effective amount of a lipase inhibitor, particularly wherein the lipase inhibitor is orlistat. Also an object of the invention is the method as described above for the simultaneous, separate or sequential administration of a compound according to formula I and a lipase inhibitor, particularly orlistat.

It is a further preferred object of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an object of the invention to provide a method as described above for the simultaneous, separate or sequential administration of a compound according to formula I and a lipase inhibitor, particularly orlistat.

It is a further particularly preferred object of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an object of the invention to provide a method as described above for the simultaneous, separate or sequential administration of a compound according to formula I and a lipase inhibitor, particularly orlistat.

A further object of the invention is the use of a compound of formula I in the manufacture of a medicament for the treatment and prevention of obesity in a patient who is also receiving treatment with a lipase inhibitor and particularly, wherein the lipase inhibitor is orlistat.

A further object of the invention is the use of a compound of formula I in the manufacture of a medicament for the treatment and prevention of obesity in a patient who is also receiving treatment with a compound selected from the following list: Nerve growth factor agonist (e.g. axokine), growth hormone agonist (e.g. AOD-9604), adrenergic uptake inhibitor (e.g. GW-320659), 5-HT reuptake inhibitor (e.g. Prozac), 5-HT/NA reuptake inhibitor (e.g. sibutramine), DA reuptake inhibitor (e.g. Buproprion), 5-HT, NA and Da reuptake blocker, steroidal plant extract (eg P57), NPY1 or 5 antagonist, MC4 agonist, CCKA agonist, MCH antagonist (e.g. SNAP 7941), H3 receptor antagonist, H1 agonist, CRF agonist, Galanin antagonist, uncoupling protein, orexin antagonist, GLP-1 agonist, IL-6 agonist, a-MSH agonist, AgRP antagonist, 5-HT1B agonist, POMC antagonist, NN2211 and Exendin-4 agonists.

A further object of the invention is the use of a compound of formula I in the manufacture of a medicament for the treatment and prevention of Type II diabetes (non-insulin dependent diabetes mellitus (NIDDM)) in a patient who is also receiving treatment with a lipase inhibitor and particularly, wherein the lipase inhibitor is orlistat.

A further preferred object of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance in a patient who is also receiving treatment with a lipase inhibitor particularly, wherein the lipase inhibitor is orlistat.

A further particularly preferred object of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance in a patient who is also receiving treatment with a lipase inhibitor particularly, wherein the lipase inhibitor is orlistat.

A further object of the present invention is the use of a compound according to formula I in the manufacture of a medicament for the treatment of sexual dysfunction.

It is also an object of the invention to provide a pharmaceutical composition comprising a compound of formula I, a therapeutically inert carrier and a therapeutically effective amount of a lipase inhibitor, particularly, wherein the lipase inhibitor is orlistat.

Other combinations which may be considered are Sibutramine comprising combinations.

It is also a preferred object of the invention to provide a method of treatment and/or prevention in mammals disorders where a reduction of the blood glucose concentration is beneficial comprising administering a therapeutically effective amount of a compound of formula I. Particularly preferred is this use or method wherein the disorders are disorders involving elevated plasma blood glucose.

The compounds of formula (I) may be used in the treatment (including prophylactic treatment) of disorders associated with 5-HT$_2$ receptor function. The compounds may act as receptor agonists or antagonists. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

A further preferred embodiment of the present invention is a process for the preparation of a compound of formula I, comprising one of the following reactions:

reaction of a compound according to formula Id in the presence of a reducing agent in order to obtain a compound according to formula I

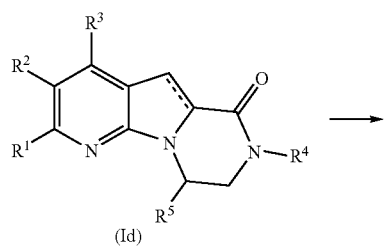

(Id)

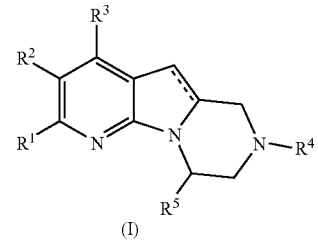

(I)

wherein $R^1$ to $R^5$ are defined as before and the dotted line in formulae Id and I represents a single or a double bond. A preferred reducing agent is e.g. LiAlH$_4$. Preferred solvents are ethers, particularly tetrahydrofuran and diethylether.

reaction of a compound according to formula B in the presence of a reducing agent in order to obtain a compound according to formula II

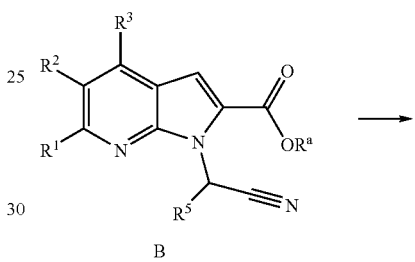

B

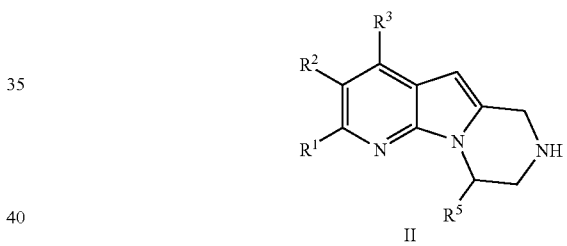

II wherein $R^1$ to $R^5$ are defined as in claim 1 and $R^a$ means alkyl, preferably methyl or ethyl. A preferred reducing agent is e.g. LiAlH$_4$. Preferred solvents are ethers, particularly tetrahydrofuran and diethyl ether.

Another preferred aspect of this invention are the following intermediates:

(4R, 9aR)-7-fluoro-4-methyl-3,4,9,9a-tetrahydro-1H-2,4a, 5-triaza-fluorene-2-carboxylic acid tert-butyl ester;

N-(5-Fluoro-pyridin-2-yl)-2,2-dimethyl-propionamide and

5-Benzoyloxy-6-bromo-pyrrolo [2,3-b] pyridine-1,2-dicarboxylic acid 1-tert-butyl ester 2-ethyl ester.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g. intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g. containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g. obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the $5\text{-}HT_{2C}$ receptor the $5\text{-}HT_{2C}$ receptors were radiolabeled with $[^3H]\text{-}5\text{-}HT$. The affinity of the compounds for $5\text{-}HT_{2C}$ receptors in a CHO cell line was determined according to the procedure of D. Hoyer, G. Engel and H. O. Kalkman, *European J. Pharmacol.*, 1985, 118, 13–23.

Method (b): For the binding to the $5\text{-}HT_{2B}$ receptor the $5\text{-}HT_{2B}$ receptors were radiolabeled with $[^3H]\text{-}5\text{-}HT$. The affinity of the compounds for human $5\text{-}HT_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the $5\text{-}HT_{2A}$ receptor the $5\text{-}HT_{2A}$ receptors were radiolabeled with $[^{125}I]\text{-}DOI$. The affinity of the compounds for $5\text{-}HT_{2A}$ receptors in a CHO cell line was determined according to the procedure of D. J. McKenna and S. J. Peroutka, *J. Neurosci.*, 1989, 9, 3482–90.

The thus determined activity of the compound of the Example is shown in Table 1.

TABLE 1

| Compound | Method (a) $K_i$ (2C) | Method (b) $K_i$ (2B) | Method (c) $K_i$ (2A) |
| --- | --- | --- | --- |
| Example 23 | 8 nM | 12 nM | 25 nM |
| Example 46 | 9 nM | 84 nM | 195 nM |
| Example 80 | 6 nM | 87 nM | 86 nM |

Preferred compounds of formula I as described above have Ki (2C) values below 10000 nM; especially preferred compounds have Ki (2C) values below 1000 nM, particularly preferred compounds have Ki (2C) values below 100 nM. Most preferred compounds have Ki (2C) values below 30 nM.

2. 2. Functional Activity

The functional activity of compounds of formula (I) was assayed using a Fluorimetric Imaging Plate reader (FLIPR). CHO cells expressing the human $5\text{-}HT_{2C}$ or human $5\text{-}HT_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 μL/well of assay buffer (Hanks balanced salt solution containing 20 mM Hepes and 2.5 mM probenecid). The drug (dissolved in 50 μL of the assay buffer) was added at a rate of 70 μL/sec to each well of the FLIPR 96 well plate during fluorescence measurements. The measurements were taken at 1 sec intervals and the maximum fluorescent signal was measured (approx 10–15 secs after drug addition) and compared with the response produced by 10 μM 5-HT (defined as 100%) to which it was expressed as a percentage response (relative efficacy). Dose response curves were constructed using Graphpad Prism (Graph Software Inc.).

TABLE 2

| Compound | h5-HT2C | | h5-HT2A | |
| --- | --- | --- | --- | --- |
| | $EC_{50}$ [nM] | Rel. Eff. [%] | $EC_{50}$ [nM] | Rel. Eff. [%] |
| Example 23 | 14 | 97 | 70 | 56 |
| Example 46 | 13 | 100 | 273 | 50 |
| Example 80 | 13 | 98 | 178 | 56 |

The compounds of formula (I) have activity at the h5-HT2c receptor in the range of 10,000 to 0.01 nM.

Preferred compounds of formula I as described above have activity at the h5-HT2c receptor below 10000 nM; especially preferred compounds below 1000 nM, particularly preferred compounds below 100 nM. Most preferred compounds have activity at the h5-HT2c receptor below 30 nM.

3. 3. Regulation of Feeding Behaviour

The in vivo activity of compounds of formula (1) was assessed for their ability to regulate feeding behaviour by recording food consumption in food deprived animals. Rats were trained to have access to food for 2 h per day and were food deprived for 22 h. When they were trained under this schedule, the amount of food taken every day during these 2 h food intake session was consistent day after day.

To test the ability of the $5\text{-}HT_{2C}$ receptor agonists to decrease food intake, 8 animals were used in a cross-over study. Rats were individually housed in plexiglass boxes with a grid on the floor and a paper was placed below the cage floor to collect any spillage. A food dispenser (becher) filled with a preweighed amount of food was presented to them for 2 h. At the end of the food intake session, rats returned to their home cage. Each rat was weighed before the start of the experiment and the amount of food consumed during this 2 h food intake session was recorded. Either various doses of test compound or Vehicle was administered orally 60 min before the 2 h food intake session. A positive control Sibutramine was included in the experiment.

An Anova analysis with repeated measures was used followed by a posthoc test Student Neumann-Keuls. *$P<0.05$ compared to Saline-treated rats.

The minimum effective dose (m.e.d.) is defined as the lowest dose which produces a statistically significant reduction in food intake. The minimum effective doses for selected particularly preferred compounds of formula I are 30 mg/kg p.o. and below.

EXAMPLES

Example 1

6-Chloro-7-ethoxy-4-methyl-1,2,3,4-tetrahydro-2,4a,5-triaza-fluorene

To a solution of 0.12 g (0.33 mmol) (R)-6-chloro-7-ethoxy-4-methyl-3,4-dihydro-1H-2,4a,5-triaza-fluorene-2-carboxylic acid tert-butyl ester in 3 mL dichloromethane 1.5 mL (2.23 g, 19.6 mmol) trifluoroacetic acid was added. After 1 h the volatile components were evaporated and the residue was purified by column chromatography on silica gel (0.030–0.063 mm) with dichloromethane:methanol:ammonia (19:1:0.1) as eluant to give the desired compound as a light yellow solid (89.5%).
ISP-MS: m/e=268.4 ([M+H$^+$])

Intermediates a) 5-Benzoyloxy-7-oxy-pyrrolo [2,3-b] pyridine-1,2-dicarboxylic acid 1-tert-butyl ester 2-ethyl ester This compound was prepared in analogy to example 3, intermediate b) from 5-benzoyloxy-pyrrolo[2,3-b]pyridine-1,2-dicarboxylic acid 1-tert-butyl ester 2-ethyl ester (Example 3, intermediate c) and m-chloroperbenzoic acid.
Colourless solid (25.7%). ISP-MS: m/e=427.5 ([M+H$^+$])

b) 5-Benzoyloxy-6-chloro-pyrrolo[2,3-b]pyridine-1,2-dicarboxylic acid 1-tert-butyl ester 2-ethyl ester This compound was prepared in analogy to example 3, intermediate h) from 5-benzoyloxy-7-oxy-pyrrolo[2,3-b]pyridine-1,2-dicarboxylic acid 1-tert-butyl ester 2-ethyl ester, ethyl chloroformate and hexamethyldisilazane.
Colourless oil (54.6%). ISP-MS: m/e=445.3 ([M+H$^+$])

c) 6-Chloro-5-hydroxy-pyrrolo[2,3-b]pyridine-1,2-dicarboxylic acid 1-tert-butyl ester 2-ethyl ester This compound was prepared in analogy to example 3, intermediate d) from 5-benzoyloxy-6-chloro-pyrrolo[2,3-b]pyridine-1,2-dicarboxylic acid 1-tert-butyl ester 2-ethyl ester and potassium carbonate.
Colourless solid (91.4%). ISP-MS: m/e=341.3 ([M+H$^+$])

d) 6-Chloro-5-ethoxy-pyrrolo[2,3-b]pyridine-1,2-dicarboxylic acid 1-tert-butyl ester 2-ethyl ester To a solution of 1.0 g (2.93 mmol) 6-chloro-5-hydroxy-pyrrolo[2,3-b]pyridine-1,2-dicarboxylic acid 1-tert-butyl ester 2-ethyl ester in 20 mL N,N-dimethylformamide was added 0.14 g (3.23 mmol) sodium hydride (60% dispersion in mineral oil). After 30 min., 0.44 mL (0.64 g, 5.87 mmol) ethyl bromide was added and the suspension stirred for 1 h. The reaction mixture was poured into 10% aqueous citric acid solution and extracted twice with ethyl acetate. The combined organic phases were washed with brine, dried over magnesium sulfate, filtered and evaporated. The residue was purified by column chromatography over silica gel (0.030–0.063 mm) with ethyl acetate:n-hexane (1:2) as eluant to give the product as a colourless crystalline solid (93.4%).
ISP-MS: m/e=369.3 ([M+H$^+$])

e) 6-Chloro-5-ethoxy-1H-pyrrolo[2,3-b]pyridine-2-carboxylic acid ethyl ester

A solution of 1.0 g (2.71 mmol) 6-chloro-5-ethoxy-pyrrolo[2,3-b]pyridine-1,2-dicarboxylic acid 1-tert-butyl ester 2-ethyl ester in 20 mL dichloromethane was cooled to 0° C., 10 mL (14.9 g, 0.13 mol) trifluoroacetic acid was added and then the cooling bath was removed. After 1 h the volatile components were removed and the residue was poured into 10% aqueous sodium bicarbonate solution and extracted twice with dichloromethane. The combined organic layers were washed with brine, dried over magnesium sulfate, filtered and evaporated. The resulting white solid (100%) was used without further purification.
ISP-MS: m/e=269.3 ([M+H$^+$])

f) (R)-1-(2-tert-Butoxycarbonylamino-1-methyl-ethyl)-6-chloro-5-ethoxy-1H-pyrrolo [2,3-b]pyridine-2-carboxylic acid ethyl ester This compound was prepared in analogy to example 3, intermediate j) from 6-chloro-5-ethoxy-1H-pyrrolo[2,3-b]pyridine-2-carboxylic acid ethyl ester, potassium tert-butoxide and (S)-5-methyl-2,2-dioxo-[1,2,3]oxathiazolidine-3-carboxylic acid tert-butyl ester.

Light yellow oil (100%). ISP-MS: m/e=426.4 ([M+H$^+$])

g) (R)-6-Chloro-7-ethoxy-4-methyl-3,4-dihydro-2H-2,4a,5-triaza-fluoren-1-one

This compound was prepared in analogy to example 3, intermediate k) from (R)-1-(2-tert-butoxycarbonylamino-1-methyl-ethyl)-6-chloro-5-ethoxy-1H-pyrrolo [2,3-b]pyridine-2-carboxylic acid ethyl ester.

White solid (66.1%). ISP-MS: m/e=280.2 ([M+H$^+$])

h) (R)-6-Chloro-7-ethoxy-4-methyl-3,4-dihydro-1H-2,4a,5-triaza-fluorene-2-carboxylic acid tert-butyl ester A suspension consisting of 0.51 g (1.82 mmol) (R)-6-chloro-7-ethoxy-4-methyl-3,4-dihydro-2H-2,4a,5-triaza-fluoren-1-one and 0.28 g (7.30 mmol) lithium aluminium hydride in 10 mL tert-butyl methyl ether was heated at reflux for 1 h. After cooling to room temperature the reaction mixture was poured into 10% aqueous sodium potassium tartrate solution and extracted twice with ethyl acetate. The organic fractions were washed with brine, dried over magnesium sulfate, filtered and evaporated. The so-obtained crude 6-chloro-7-ethoxy-4-methyl-1,2,3,4-tetrahydro-2,4a,5-triaza-fluorene was dissolved in 10 mL dichloromethane and 0.48 g (2.19 mmol) di-tert-butyl dicarbonate and 22.3 mg (0.18 mmol) 4-(dimethylamino)pyridine were added. After 1 h the solvent was evaporated and the residue was purified by column chromatography over silica gel (0.030–0.063 mm) with ethyl acetate:n-hexane (1:4) as eluant to give the product as a light yellow solid (63.9%).

ISP-MS: m/e=366.3 ([M+H$^+$])

Example 2

(4R,9aR)-6-Chloro-7-ethoxy-4-methyl-1,2,3,4,9,9a-hexahydro-2,4a,5-triaza-fluorene This compound was prepared in analogy to Example 1 from (4R,9aR)-6-chloro-7-ethoxy-4-methyl-3,4,9,9a-tetrahydro-1H-2,4a,5-triaza-fluorene-2-carboxylic acid tert-butyl ester and trifluoroacetic acid.

Light yellow oil (84.4%). ISP-MS: m/e=268.4 ([M+H$^+$])

Intermediate (4R,9aR)-6-Chloro-7-ethoxy-4-methyl-3,4,9,9a-tetrahydro-1H-2,4a,5-triaza-fluorene-2-carboxylic acid tert-butyl ester To a solution of 0.30 g (0.82 mmol) (R)-6-chloro-7-ethoxy-4-methyl-3,4-dihydro-1H-2,4a,5-triaza-fluorene-2-carboxylic acid tert-butyl ester in 6 mL acetic acid 0.26 g (4.10 mmol) sodium cyanoborohydride was added. After 1 h the reaction was poured into 10% aqueous sodium bicarbonate solution and extracted three times with ethyl acetate. The combined organic layers were washed with brine, dried over magnesium sulfate, filtered and evaporated. The residue was purified by column chromatography over silica gel with ethyl acetate:n-hexane (1:2) as eluant to yield the product as a light yellow oil (96.8%).

ISP-MS: m/e=368.3 ([M+H$^+$])

Example 3

(4R,9aR)-6-Chloro-4,7-dimethyl-1,2,3,4,9,9a-hexahydro-2,4a,5-triaza-fluorene

To a solution of 0.20 g (0.59 mmol) (4R,9aR)-6-chloro-4,7-dimethyl-3,4,9,9a-tetrahydro-1H-2,4a,5-triaza-fluorene-2-carboxylic acid tert-butyl ester in 2 mL dichloromethane was added 0.91 mL (1.35 g, 11.8 mmol) trifluoroacetic acid. After 30 min., all volatile components were removed at a rotary evaporator and the residue was purified by column chromatography on silica gel with dichloromethane:methanol:ammonia (19:1:0.1) as eluant to give the desired compound as a colourless oil (95.9%).

ISP-MS: m/e=238.2 ([M+H$^+$])

Intermediates a) Pyrrolo[2,3-b]pyridine-1,2-dicarboxylic acid 1-tert-butyl ester 2-ethyl ester To a solution of 80.9 g (0.43 mol) 1H-pyrrolo[2,3-b]pyridine-2-carboxylic acid ethyl ester in 1800 mL acetonitrile was added 111.4 g (0.51 mol) di-tert-butyl dicarbonate followed by 2.60 g (0.02 mol) 4-dimethylaminopyridine. After 1 h the solvent was evaporated at a rotary evaporator and the residue was purified by flash column chromatography over silica gel (0.032–0.063 mm) with n-hexane:ethyl acetate (9:1) as eluant to give the product as a yellow oil (96.6%).

ISP-MS: m/e=291.2 ([M+H$^+$])

b) 7-Oxy-pyrrolo[2,3-b]pyridine-1,2-dicarboxylic acid 1-tert-butyl ester 2-ethyl ester To a solution of 88.7 g (0.31 mol) pyrrolo[2,3-b]pyridine-1,2-dicarboxylic acid 1-tert-butyl ester 2-ethyl ester in 1600 mL dichloromethane was added 150.5 g (0.61 mol) 3-chloroperoxybenzoic acid. After 7 h another 150.5 g (0.61 mol) 3-chloroperoxybenzoic acid was added. After 24 h the reaction mixture was poured into 960 mL saturated aqueous potassium carbonate solution. Water and dichloromethane (1750 mL, 1:1 v/v) were added, after 5 min the aqueous phase was separated and extracted three times with 900 mL portions of dichloromethane. The combined organic phases were washed with 1000 mL water and 1000 mL brine, dried over magnesium sulfate and filtered. The solvent was removed at a rotary evaporator until a white suspension had formed. To this, 150 mL tert-butyl methyl ether was added and the suspension was filtered. The white solid was washed with 70 mL tert-butyl methyl ether and dried under high vacuum to give the desired product as a colourless solid (59.5%).

EI-MS: m/e=306.2 ([M])

c) 5-Benzoyloxy-pyrrolo[2,3-b]pyridine-1,2-dicarboxylic acid 1-tert-butyl ester 2-ethyl ester A solution of 50.0 g (0.16 mol) 7-oxy-pyrrolo[2,3-b]pyridine-1,2-dicarboxylic acid 1-tert-butyl ester 2-ethyl ester was treated simultaneously with solutions of 49.0 mL (75.5 g, 0.41 mol) benzoyl bromide in 400 mL toluene and 34.2 mL (26.3 g, 0.16 mol) hexamethyldisilazane in 400 mL toluene. After 2 h the yellow cloudy solution was poured into 1 l aqueous saturated sodium bicarbonate and extracted with 1 l ethyl acetate. The organic phase was washed twice with 1 l 10% aqueous sodium carbonate solution, brine and dried over magnesium sulfate. After evaporation of the solvent the remaining orange oil was purified by column chromatography over silica gel (0.030–0.063 mm) with a gradient of ethyl acetate and n-hexane (1:20–1:6). The product-containing fractions were dissolved in 500 mL dichloromethane and washed with 500 mL 10% aqueous sodium carbonate solution. The organic layer was dried over magnesium sulfate, filtered and evaporated to give the product as a colourless foam (9.7%).

ISP-MS: m/e=411.4 ([M+H$^+$])

d) 5-Hydroxy-pyrrolo[2,3-b]pyridine-1,2-dicarboxylic acid 1-tert-butyl ester 2-ethyl ester To a solution of 2.20 g (5.36 mmol) 5-benzoyloxy pyrrolo[2,3-b]pyridine-1,2-dicarboxylic acid 1-tert-butyl ester 2-ethyl ester in 20 mL methanol was added 0.81 g (5.90 mmol) potassium carbonate. After 1 h the reaction was poured into ethyl acetate and extracted with 10% aqueous citric acid solution. The phases were separated and the organic layer was washed with brine, dried over magnesium sulfate and evaporated. The residue was purified by column chromatography over silica gel (0.030–0.063 mm) with ethyl acetate:n-hexane (1:1) to give the product as a colourless oil (100%).

ISP-MS: m/e=307.3 ([M+H$^+$])

e) 5-Methyl-1H-pyrrolo[2,3-b]pyridine-2-carboxylic acid ethyl ester

A solution of 4.0 g (13.1 mmol) 5-hydroxy-pyrrolo[2,3-b]pyridine-1,2-dicarboxylic acid 1-tert-butyl ester 2-ethyl ester in 100 mL dichloromethane was cooled to 0° C. and 2.2 mL (1.6 g, 15.7 mmol) triethylamine and 2.6 mL (4.4 g, 15.7 mmol) trifluoromethanesulfonic acid were added. After 2 h at 0° C. the reaction was poured into 10% aqueous sodium bicarbonate solution and extracted with dichloromethane. The organic layer was washed with brine, dried over magnesium sulfate and evaporated. The residue was dissolved in 100 mL tetrahydrofuran and 0.75 g (0.65 mmol) tetrakis(triphenylphosphine)palladium (0) and 13.1 mL trimethylaluminium (2M solution in n-heptane) were added. The reaction mixture was heated to reflux for 2 h and after cooling to room temperature poured into ethyl acetate and water, filtered through speedex and extracted with ethyl acetate. The organic layer was washed with brine, dried over magnesium sulfate, filtered and evaporated. The residue was purified by column chromatography over silica gel (0.030–0.063 mm) with ethyl acetate:n-hexane (1:1) as eluant to give the product as a light yellow solid (64.5%).

ISP-MS: m/e=205.2 ([M+H$^+$])

f) 5-Methyl-pyrrolo[2,3-b]pyridine-1,2-dicarboxylic acid 1-tert-butyl ester 2-ethyl ester To a solution of 1.15 g (5.6 mmol) 5-methyl-1H-pyrrolo[2,3-b]pyridine-2-carboxylic acid ethyl ester in 20 mL dichloromethane were added 1.47 g (6.76 mmol) di-tert-butyl dicarbonate and 68.8 mg (0.56 mmol) 4-dimethylaminopyridine. After 2 h the solvent was evaporated and the residue purified by column chromatography over silica gel (0.030–0.063 mm) with ethyl acetate:n-hexane (1:4) as eluant to give the product as a colourless oil (86.4%).

ISP-MS: m/e=305.3 ([M+H$^+$])

g) 5-Methyl-7-oxy-pyrrolo[2,3-b]pyridine-1,2-dicarboxylic acid 1-tert-butyl ester 2-ethyl ester To a solution of 0.20 g (0.66 mmol) 5-methyl-pyrrolo[2,3-b]pyridine-1,2-dicarboxylic acid 1-tert-butyl ester 2-ethyl ester in 4 mL dichloromethane were added 324 mg (1.31 mmol; 70%) meta-chloroperbenzoic acid. After 5.5 h another 324 mg (1.31 mmol; 70%) meta-chloroperbenzoic acid were added and the reaction was stirred for 18 h. The reaction mixture was poured into saturated aqueous potassium carbonate solution and extracted with dichloromethane until no further product was detected in the aqueous phase. The combined organic phases were washed with brine, dried over magnesium sulfate, filtered and evaporated. The residue was purified by flash column chromatography over silica gel (0.030–0.063 mm) with a gradient of ethyl acetate:n-hexane (1:100□1:1) as eluant to give the product as a light yellow solid (35.3%).

ISP-MS: m/e=321.3 ([M+H$^+$])

h) 6-Chloro-5-methyl-pyrrolo[2,3-b]pyridine-1,2-dicarboxylic acid 1-tert-butyl ester 2-ethyl ester 0.20 g (0.62 mmol) 5-Methyl-7-oxy-pyrrolo[2,3-b]pyridine-1,2-dicarboxylic acid 1-tert-butyl ester 2-ethyl ester was dissolved in 12 mL tetrahydrofuran and 0.13 mL (0.10 g, 0.62 mmol) hexamethyldisilazane and 0.12 mL (0.15 g, 1.56 mmol) ethyl chloroformate were added. After 2 h the reaction was poured into saturated aqueous sodium bicarbonate solution and extracted twice with ethyl acetate. The combined organic phases were washed with brine, dried over magnesium sulfate, filtered and evaporated. The residue was purified by flash column chromatography over silica gel (0.030–0.063 mm) with ethyl acetate:n-hexane (1:7) as eluant to give the product as a light yellow solid (71.9%).

ISP-MS: m/e=339.1 ([M+H$^+$])

i) 6-Chloro-5-methyl-1H-pyrrolo[2,3-b]pyridine-2-carboxylic acid ethyl ester A solution of 0.53 g (1.56 mmol) 6-chloro-5-methyl-pyrrolo[2,3-b]pyridine-1,2-dicarboxylic acid 1-tert-butyl ester 2-ethyl ester in 8 mL dichloromethane was cooled to 0° C., 1.44 mL (2.14 g, 18.8 mmol) trifluoroacetic acid was added and the cooling bath removed. After 2 h the volatile components were removed and the residue was poured into saturated aqueous sodium bicarbonate solution and extracted twice with dichloromethane. The combined organic layers were washed with brine, dried over magnesium sulfate, filtered and evaporated. The resulting off-white solid (91.1%) was used without further purification.

ISP-MS: m/e=239.2 ([M+H$^+$])

j) (R)-1-(2-tert-Butoxycarbonylamino-1-methyl-ethyl)-6-chloro-5-methyl-1H-pyrrolo[2,3-b]pyridine-2-carboxylic acid ethyl ester A stirred solution of 0.34 g (1.42 mmol) 6-chloro-5-methyl-1H-pyrrolo[2,3-b]pyridine-2-carboxylic acid ethyl ester in 7 mL N,N-dimethylformamide was cooled to 0° C. Potassium tert-butoxide (0.17 g, 1.50 mmol) was added and after 30 min. 0.37 g (1.57 mmol) (S)-5-methyl-2,2-dioxo-[1,2,3]oxathiazolidine-3-carboxylic acid tert-butyl ester was added and the cooling bath was removed. After 3 h the reaction mixture was poured into 10% aqueous citric acid solution and extracted three times with ethyl acetate. The combined organic layers were washed with water and brine, dried over magnesium sulfate, filtered and evaporated. The residue was purified by column chromatography over silica gel (0.030–0.063 mm) with ethyl acetate:n-hexane (1:5) as eluant to give the product as a colourless solid (87.8%).

ISP-MS: m/e=396.3 ([M+H$^+$])

l) ®-6-Chloro-4,7-dimethyl-3,4-dihydro-2H-2,4a,5-triaza-fluoren-1-one

To an ice-cold solution of 0.50 g (1.25 mmol) ®-1-(2-tert-butoxycarbonylamino-1-methyl-ethyl)-6-chloro-5-methyl-1H-pyrrolo[2,3-b]pyridine-2-carboxylic acid ethyl ester in 6 mL dichloromethane was added 1.91 mL (2.85 g, 25.0 mmol) trifluoroacetic acid; the ice-bath was removed after complete addition. After 45 min., the volatile components were removed and the residue was dissolved in 3 mL methanol then treated cautiously with 0.70 g (5.0 mmol) potassium carbonate. After 2 h the reaction mixture was poured into water and ethyl acetate and the separated aqueous phase was extracted twice with ethyl acetate. The combined organic layers were washed with brine, dried over magnesium sulfate and evaporated. The residue was dissolved in dichloromethane and tert-butyl methyl ether, evaporated under vacuum until a suspension appeared, then cooled to 0° C. The ice-cold suspension was filtered and the filter cake was washed with tert-butyl methyl ether to give the product as a colourless solid (73.7%).

ISP-MS: m/e=250.1 ([M+H$^+$])

l) (R)-6-Chloro-4,7-dimethyl-1,2,3,4-tetrahydro-2,4a,5-triaza-fluorene

To a stirred suspension of 5 mL tert-butyl methyl ether and 0.14 g (3.68 mmol) lithium aluminium hydride was added 0.23 g (0.92 mmol) (R)-6-chloro-4,7-dimethyl-3,4-dihydro-2H-2,4a,5-triaza-fluoren-1-one. The suspension was stirred under reflux for 15 min and, after cooling to room temperature, was poured into saturated aqueous sodium potassium tartrate solution and extracted with ethyl acetate. After filtration over speedex the phases were separated and the aqueous phase was extracted twice with ethyl acetate. The combined organic layers were washed with brine, dried over magnesium sulfate and evaporated. The so-obtained product was used without further purification.

Light yellow solid (99.0%). ISP-MS: m/e=236.1 ([M+H$^+$])

m) (R)-6-Chloro-4,7-dimethyl-3,4-dihydro-1H-2,4a,5-triaza-fluorene-2-carboxylic acid tert-butyl ester To a solution of 0.21 g (0.89 mmol) (R)-6-chloro-4,7-dimethyl-1,2,3,4-tetrahydro-2,4a,5-triaza-fluorene in 2 mL dichloromethane were added 0.23 g (1.07 mmol) di-tert-butyl dicarbonate and 54.0 mg (0.04 mmol) 4-(dimethylamino)pyridine. After 30 min. the solvent was evaporated and the residue was purified by flash column chromatography over silica gel (0.030–0.063 mm) with ethyl acetate:n-hexane (1:5) as eluant to give the product as a light yellow foam (89.6%).

ISP-MS: m/e=336.2 ([M+H$^+$])

n) (4R,9aR)-6-Chloro-4,7-dimethyl-3,4,9,9a-tetrahydro-1H-2,4a,5-triaza-fluorene-2-carboxylic acid tert-butyl ester To a solution of 0.26 g (0.77 mmol) (R)-6-chloro-4,7-dimethyl-3,4-dihydro-1H-2,4a,5-triaza-fluorene-2-carboxylic acid tert-butyl ester in 5 mL acetic acid was added 0.24 g (3.87 mmol) sodium cyanoborohydride. After 2 h the volatile components were removed at a rotary evaporator and the residue was taken up in ethyl acetate and treated with 32% aqueous sodium hydroxide solution until a pH of 11 was obtained. The aqueous phase was extracted twice with ethyl acetate and the combined organic layers were washed with brine, dried over magnesium sulfate and evaporated. The residue was purified by column chromatography over silica gel (0.030–0.063 mm) with ethyl acetate:n-hexane (1:7) as eluant to give the product as a colourless oil (80.3%).

ISP-MS: m/e=338.2 ([M+H$^+$])

Example 4

(4R,9aR)-6-Bromo-7-ethoxy-4-methyl-1,2,3,4,9,9a-hexahydro-2,4a,5-triaza-fluorene; hydrochloride This compound was prepared in analogy to example 1 from (4R,9aR)-6-bromo-7-ethoxy-4-methyl-3,4,9,9a-tetrahydro-1H-2,4a,5-triaza-fluorene-2-carboxylic acid tert-butyl ester. The free base was converted into its hydrochloride salt by treatment of an ethyl acetate solution of the free base with hydrochloric acid (2.2M solution in ethyl acetate; 1.1 mole equivalents), filtration of the suspension and washing of the precipitate with ether:n-hexane (1:1).

Yellow solid (89.4%). ISP-MS: m/e=312.1 ([M+H$^+$])

Intermediates a) 5-Benzoyloxy-6-bromo-pyrrolo[2,3-b]pyridine-1,2-dicarboxylic acid 1-tert-butyl ester 2-ethyl ester To a solution of 0.30 g (0.70 mmol) 5-benzoyloxy-7-oxy-pyrrolo[2,3-b]pyridine-1,2-dicarboxylic acid 1-tert-butyl ester 2-ethyl ester (Example 2, intermediate b) in 8 mL tetrahydrofuran were added simultaneously 0.15 mL (0.11 g, 0.70 mmol) hexamethyldisilazane and 0.14 mL (0.21 g, 1.16 mmol) benzoyl bromide in 4 mL tetrahydrofuran . After 2 h the reaction was poured into saturated aqueous sodium bicarbonate solution and extracted three times with ethyl acetate. The combined organic layers were washed with brine, dried over magnesium sulfate, filtered and evaporated. The residue was purified by column chromatography over silica gel (0.030–0.063 mm) with ethyl acetate:n-hexane (1:1) as eluant to give the compound as a colourless oil (62.7%).

ISP-MS: m/e=489.1 ([M+H$^+$])

b) 6-Bromo-5-hydroxy-pyrrolo [2,3-b]pyridine-1,2-dicarboxylic acid 1-tert-butyl ester 2-ethyl ester This compound was prepared in analogy to Example 3, intermediate d) from 5-benzoyloxy-6-bromo-pyrrolo [2,3-b] pyridine-1,2-dicarboxylic acid 1-tert-butyl ester 2-ethyl ester and potassium carbonate.

Light yellow solid (96.5%). ISP-MS: m/e=387.2 ([M+H$^+$])

c) 6-Bromo-5-ethoxy-pyrrolo[2,3-b]pyridine-1,2-dicarboxylic acid 1-tert-butyl ester 2-ethyl ester This compound was prepared in analogy to Example 1, intermediate d) from 6-bromo-5-hydroxy-pyrrolo [2,3-b] pyridine-1,2-dicarboxylic acid 1-tert-butyl ester 2-ethyl ester, sodium hydride and ethyl bromide.

Colourless solid (77.0%) ISP-MS: m/e=415.2 ([M+H$^+$])

d) 6-Bromo-5-ethoxy-1H-pyrrolo[2,3-b]pyridine-2-carboxylic acid ethyl ester

This compound was prepared in analogy to Example 1, intermediate e) from 6-bromo-5-ethoxy-1H-pyrrolo[2,3-b]pyridine-2-carboxylic acid ethyl ester and trifluoroacetic acid.

Off-white solid (96.4%). ISP-MS: m/e=315.2 ([M+H$^+$])

e) (R)-6-Bromo-1-(2-tert-butoxycarbonylamino-1-methyl-ethyl)-5-ethoxy-1H-pyrrolo[2,3-b]pyridine-2-carboxylic acid ethyl ester This compound was prepared in analogy to example 3, intermediate j) from 6-bromo-5-ethoxy-1H-pyrrolo[2,3-b]pyridine-2-carboxylic acid ethyl ester, potassium tert-butoxide and (S)-5-methyl-2,2-dioxo-[1,2,3]oxathiazolidine-3-carboxylic acid tert-butyl ester.

Yellow foam (100%). ISP-MS: m/e=470.2 ([M+H$^+$])

f) (R)-6-Bromo-7-ethoxy-4-methyl-3,4-dihydro-2H-2,4a,5-triaza-fluoren-1-one

This compound was prepared in analogy to example 3, intermediate k) from (R)-6-bromo-1-(2-tert-butoxycarbonylamino-1-methyl-ethyl)-5-ethoxy-1H-pyrrolo [2,3-b]pyridine-2-carboxylic acid ethyl ester.

Colourless solid (92.0%). ISP-MS: m/e=324.2 ([M+H$^+$])

g) (R)-6-Bromo-7-ethoxy-4-methyl-3,4-dihydro-1H-2,4a,5-triaza-fluorene-2-carboxylic acid tert-butyl ester This compound was prepared in analogy to example 1, intermediate h) from (R)-6-bromo-7-ethoxy-4-methyl-3,4-dihydro-2H-2,4a,5-triaza-fluoren-1-one, lithium aluminum hydride and subsequent reaction of the amine with di-tert-butyl-dicarbonate and 4-(dimethylamino)pyridine.

Yellow solid (74.9%). ISP-MS: m/e=412.3 ([M+H$^+$])

h) (4R,9aR)-6-Bromo-7-ethoxy-4-methyl-3,4,9,9a-tetrahydro-1H-2,4a,5-triaza-fluorene-2-carboxylic acid tert-butyl ester This compound was prepared in analogy to example 2, intermediate, from (R)-6-bromo-7-ethoxy-4-methyl-3,4-dihydro-1H-2,4a,5-triaza-fluorene-2-carboxylic acid tert-butyl ester and sodium cyanoborohydride.

Pale yellow solid (98.4%) ISP-MS: m/e=414.3 ([M+H$^+$])

Example 5

(4R,9aR)-7-Chloro-4,6-dimethyl-1,2,3,4,9,9a-hexahydro-2,4a,5-triaza-fluorene This compound was prepared in analogy to example 1 from (4R,9aR)-7-chloro-4,6-dimethyl-3,4,9,9a-tetrahydro-1H-2,4a,5-triaza-fluorene-2-carboxylic acid tert-butyl ester.

Yellow solid (90%). ISP-MS: m/e=238.2 ([M+H$^+$])

Intermediates a) (4R,9aR)-7-Chloro-4,6-dimethyl-3,4,9,9a-tetrahydro-1H-2,4a,5-triaza-fluorene-2-carboxylic acid tert-butyl ester To a solution of 0.20 g (0.66 mmol) (R)-4,6-dimethyl-3,4-dihydro-1H-2,4a,5-triaza-fluorene-2-carboxylic acid tert-butyl ester in 2 mL tetrahydrofuran was added 92.1 μg (0.69 mmol) N-chlorosuccinimide. The reaction was stirred at 50 deg C. for 18 h, then the solvent was evaporated and the residue was purified by column chromatography on silica gel (0.032–0.063 mm) with ethyl acetate:dichloromethane (1:19) as eluant.

Light yellow solid (81.7%). ISP-MS: m/e=338.2 ([M+H$^+$])

b) (R)-4,6-Dimethyl-3,4-dihydro-1H-2,4a,5-triaza-fluorene-2-carboxylic acid tert-butyl ester To a solution of 19.5 g (0.053 mol) (4R,10aR)-6-bromo-4-methyl-3,4,9,9a-tetrahydro-1H-2,4a,5-triaza-fluorene-2-carboxylic acid tert-butyl ester in 800 mL 1,2-dimethoxyethane were added 12.2 g (0.01 mol) tetrakis(triphenylphosphine)palladium(0) and the suspension was stirred for 30 min. at room temperature. Then, 400 mL water, 16.8 g (0.16 mol) sodium carbonate and 13.3 g (0.10 mol) trimethylboroxine were added and the reaction mixture was stirred for 3 h under reflux. The suspension was poured into 10% aqueous sodium bicarbonate solution and ethyl acetate and the phases were separated. The organic layer was washed with brine, dried over magnesium sulfate, filtered and evaporated. The residue was purified by column chromatography on silica gel (0.032–0.063 mm) with n-hexane:ethyl acetate (4:1) as eluent to give the compound as a light yellow oil (52.6%).

ISP-MS: m/e=304.3 ([M+H$^+$])

c) (4R,9aR)-6-Bromo-4-methyl-3,4,9,9a-tetrahydro-1H-2,4a,5-triaza-fluorene-2-carboxylic acid tert-butyl ester This compound was prepared in analogy to example 2, intermediate, from (4R)-6-bromo-4-methyl-3,4-dihydro-1H-2,4a,5-triaza-fluorene-2-carboxylic acid tert-butyl ester and sodium cyanoborohydride.

Colourless solid (82.5.%). ISP-MS: m/e=370.3 ([M+H$^+$])

d) (R)-6-Bromo-4-methyl-3,4-dihydro-1H-2,4a,5-triaza-fluorene-2-carboxylic acid tert-butyl ester This compound was prepared in analogy to example 1, intermediate h) from (R)-6-bromo-4-methyl-1,2,3,4-tetrahydro-2,4a,5-triaza-fluorene and di tert-butyl dicarbonate.

Light yellow foam (97.3%). ISP-MS: m/e=366.1 ([M+H$^+$])

e) (R)-6-Bromo-4-methyl-3,4-dihydro-2H-2,4a,5-triaza-fluoren-1-one

This compound was prepared in analogy to example 3, intermediate k) from (R)-6-bromo-1-(2-tert-butoxycarbonylamino-1-methyl-ethyl)-1H-pyrrolo [2,3-b]pyridine-2-carboxylic acid ethyl ester.

Colourless solid (73.6%). ISP-MS: m/e=282.0 ([M+H$^+$])

f) (R)-6-Bromo-1-(2-tert-butoxycarbonylamino-1-methyl-ethyl)-1H-pyrrolo[2,3-b]pyridine-2-carboxylic acid ethyl ester This compound was prepared in analogy to example 3, intermediate j) from 6-bromo-1H-pyrrolo[2,3-b]pyridine-2-carboxylic acid ethyl ester and (S)-5-methyl-2,2-dioxo- [1,2,3]oxathiazolidine-3-carboxylic acid tert-butyl ester.

Yellow gum (93.2%). ISP-MS: m/e=426.3 ([M+H$^+$])

g) 6-Bromo-1H-pyrrolo[2,3-b]pyridine-2-carboxylic acid ethyl ester

A stirred solution of 18.4 g (0.05 mol) 6-bromo-pyrrolo [2,3-b]pyridine-1,2-dicarboxylic acid 1-tert-butyl ester 2-ethyl ester in 165 mL dichloromethane was cooled to 0 deg C. and then 38.0 mL trifluoroacetic acid was added over 5 min. The cooling bath was removed and after 2 h at room temperature the reaction mixture was poured into 500 mL saturated aqueous sodium bicarbonate solution. The organic layer was extracted three times with 150 mL portions of dichloromethane; the combined organic phases were washed with 200 mL brine, dried over magnesium sulfate and filtered. The solvent was evaporated and the residue was dried under high vacuum to give 12.0 g (95.5%) of the desired product as a colourless solid.

ISP-MS: m/e=269.2 ([M+H$^+$])

h) 6-Bromo-pyrrolo [2,3-b]pyridine-1,2-dicarboxylic acid 1-tert-butyl ester 2-ethyl ester To a stirred suspension of 30.0 g (0.098 mol) 7-oxy-pyrrolo[2,3-b]pyridine-1,2-dicarboxylic acid 1-tert-butyl ester 2-ethyl ester (example 3, intermediate b) in toluene were added simultaneously solutions of 20.5 mL (15.8 g, 0.098 mol) hexamethyldisilazane in 420 mL toluene and 29.4 mL (45.3 g, 0.24 mol) benzoyl bromide in 420 mL toluene over 1 h. After an additional hour the reaction mixture was poured into 400 mL 10% aqueous sodium carbonate solution and the phases were separated. The aqueous phase was extracted twice with 500 mL ethyl acetate; the combined organic layers were washed twice with 600 mL saturated sodium carbonate solution and brine. After filtration and removal of the solvent the residue was purified by column chromatography over silica gel (0.032–0.063 mm) with n-hexane:ethyl acetate (24:1 then 19:1) as eluent to give the product as a colourless solid (50.9%).

ISP-MS: m/e=371.1 ([M+H$^+$])

Example 6

(4R,9aR)-7-Bromo-4,6-dimethyl-1,2,3,4,9,9a-hexahydro-2,4a,5-triaza-fluorene This compound was prepared in analogy to example 1 from (4R,9aR)-7-bromo-4,6-dimethyl-3,4,9,9a-tetrahydro-1H-2,4a,5-triaza-fluorene-2-carboxylic acid tert-butyl ester.

Yellow solid (94.8%). ISP-MS: m/e=282.0 ([M+H$^+$])

Intermediate (4R,9aR)-7-Bromo-4,6-dimethyl-3,4,9,9a-tetrahydro-1H-2,4a,5-triaza-fluorene-2-carboxylic acid tert-butyl ester To a stirred solution of 0.20 g (0.66 mmol) (R)-4,6-dimethyl-3,4-dihydro-1H-2,4a,5-triaza-fluorene-2-carboxylic acid tert-butyl ester (example 5, intermediate b)) in 2 mL tetrahydrofuran 0.12 g (0.69 mmol) was added N-bromosuccinimide; the reaction was stirred for 1.5 h. The solvent was evaporated and the residue was purified by column chromatography on silica gel (0.032–0.063 mm) with ethyl acetate:dichloromethane (1:19) as eluant.

Colourless foam (79.4%). ISP-MS: m/e=382.2 ([M+H$^+$])

Example 7

(4R,9aR)-4,6-Dimethyl-1,2,3,4,9,9a-hexahydro-2,4a,5-triaza-fluoren-7-ol

This compound was prepared in analogy to example 1 from (4R,9aR)-7-hydroxy-4,6-dimethyl-3,4,9,9a-tetrahydro-1H-2,4a,5-triaza-fluorene-2-carboxylic acid tert-butyl ester.

Light brown foam (85.7%). ISP-MS: m/e=220.3 ([M+H$^+$])

Intermediate (4R,9aR)-7-Hydroxy-4,6-dimethyl-3,4,9,9a-tetrahydro-1H-2,4a,5-triaza-fluorene-2-carboxylic acid tert-butyl ester A stirred solution of 5.40 g (14.1 mmol) (4R,9aR)-7-bromo-4,6-dimethyl-3,4,9,9a-tetrahydro-1H-2,4a,5-triaza-fluorene-2-carboxylic acid tert-butyl ester in 350 mL diethyl ether was cooled to −100 deg C. and 6.30 mL (5.13 g, 27.7 mmol) triisopropyl borate was added. To this solution, 11.3 mL (16.9 mmol) tert-butyllithium (1.5 M in n-pentane) was added dropwise and the reaction was stirred at this temperature for another 15 min. The reaction was warmed to −75 deg C., stirred for another 15 min., warmed to 0 deg C., stirred again for 15 min. and then 6.85 mL acetic acid (50% in water) and 0.12 g 35% hydrogen peroxide solution were added successively. The cooling bath was removed and the reaction was stirred for 1 h at room temperature. The reaction mixture was extracted with 10% aqueous thiosulfate solution, the organic layer was washed with brine, dried over magnesium sulfate and filtered. The solvent was removed at a rotary evaporator and the residue was purified by column chromatography on silica gel (0.032–0.063 mm) with ethyl acetate:n-hexane (1:1) as eluant to give the compound as a light yellow solid (75.4%).

ISP-MS: m/e=320.4 ([M+H$^+$])

Example 8

(4R,9aR)-7-Methoxy-4,6-dimethyl-1,2,3,4,9,9a-hexahydro-2,4a,5-triaza-fluorene This compound was prepared in analogy to example 1 from (4R,9aR)-7-methoxy-4,6-dimethyl-3,4,9,9a-tetrahydro-1H-2,4a,5-triaza-fluorene-2-carboxylic acid tert-butyl ester.

Light yellow oil (68.8%). ISP-MS: m/e=234.2 ([M+H$^+$])

Intermediate

(4R,9aR)-7-Methoxy-4,6-dimethyl-3,4,9,9a-tetrahydro-1H-2,4a,5-triaza-fluorene-2-carboxylic acid tert-butyl ester To a stirred solution of 90.0 mg (0.28 mmol) (4R,9aR)-7-hydroxy-4,6-dimethyl-3,4,9,9a-tetrahydro-1H-2,4a,5-triaza-fluorene-2-carboxylic acid tert-butyl ester (example 7, intermediate) in 1.0 mL N,N-dimethylformamide was added 14.8 mg (0.34 mmol) sodium hydride (55–65% dispersion in oil) and the reaction was stirred for 30 min. Then, 35 µl (80.0 mg, 0.56 mmol) methyl iodide was added. After 2 h the reaction mixture was diluted with ethyl acetate, washed with 10% aqueous sodium bicarbonate solution and brine, dried over magnesium sulfate and filtered. The solvent was removed at a rotary evaporator and the residue was purified by column chromatography on silica gel (0.032–0.063 mm) with ethyl acetate:n-hexane (1:1) as eluant.

Light yellow oil (60.7%). ISP-MS: m/e=334.3 ([M+H$^+$])

Example 9

(4R,9aR)-7-Ethoxy-4,6-dimethyl-1,2,3,4,9,9a-hexahydro-2,4a,5-triaza-fluorene; hydrochloride This compound was prepared in analogy to example 4 from (4R,10aR)-7-ethoxy-4,6-dimethyl-3,4,9,9a-tetrahydro-1H-2,4a,5-triaza-fluorene-2-carboxylic acid tert-butyl ester.

Light yellow solid (66.8%). ISP-MS: m/e=248.3 ([M+H$^+$])

Intermediate

(4R,10aR)-7-Ethoxy-4,6-dimethyl-3,4,9,9a-tetrahydro-1H-2,4a,5-triaza-fluorene-2-carboxylic acid tert-butyl ester This compound was prepared in analogy to example 1 intermediate d), from (4R,9aR)-7-hydroxy-4,6-dimethyl-3,4,9,9a-tetrahydro-1H-2,4a,5-triaza-fluorene-2-carboxylic acid tert-butyl ester (example 7, intermediate), sodium hydride and ethyl bromide.

Yellow foam (67.5%). ISP-MS: m/e=348.5 ([M+H$^+$])

Example 10

(4R,9aR)-7-Isopropoxy-4,6-dimethyl-1,2,3,4,9,9a-hexahydro-2,4a,5-triaza-fluorene This compound was prepared in analogy to example 1 from (4R,9aR)-7-isopropoxy-4,6-dimethyl-3,4,9,9a-tetrahydro-1H-2,4a,5-triaza-fluorene-2-carboxylic acid tert-butyl ester.

Yellow oil (87.3%). ISP-MS: m/e=262.2 ([M+H$^+$])

Intermediate

(4R,9aR)-7-Isopropoxy-4,6-dimethyl-3,4,9,9a-tetrahydro-1H-2,4a,5-triaza-fluorene-2-carboxylic acid tert-butyl ester This compound was prepared in analogy to example 1 intermediate d), from (4R,9aR)-7-hydroxy-4,6-dimethyl-3,4,9,9a-tetrahydro-1H-2,4a,5-triaza-fluorene-2-carboxylic acid tert-butyl ester (example 7, intermediate), sodium hydride and 2-bromopropane.

Light yellow oil (85.7%). ISP-MS: m/e=362.3 ([M+H$^+$])

Example 11

(4R,9aR)-7-Cyclopropylmethoxy-4,6-dimethyl-1,2,3,4,9,9a-hexahydro-2,4a,5-triaza-fluorene This compound was prepared in analogy to example 1 from (4R,9aR)-7-cyclopropylmethoxy-4,6-dimethyl-3,4,9,9a-tetrahydro-1H-2,4a,5-triaza-fluorene-2-carboxylic acid tert-butyl ester.

Light yellow oil (86.7%). ISP-MS: m/e=274.3 ([M+H$^+$])

Intermediate

(4R,9aR)-7-Cyclopropylmethoxy-4,6-dimethyl-3,4,9,9a-tetrahydro-1H-2,4a,5-triaza-fluorene-2-carboxylic acid tert-butyl ester This compound was prepared in analogy to example 1 intermediate d), from (4R,9aR)-7-hydroxy-4,6-dimethyl-3,4,9,9a-tetrahydro-1H-2,4a,5-triaza-fluorene-2-carboxylic acid tert-butyl ester (example 7, intermediate), sodium hydride and (bromomethyl)cyclopropane.

Light yellow oil (81.1%). ISP-MS: m/e=374.4 ([M+H$^+$])

Example 12

(4R,9aR)-7-(2-Methoxy-ethoxy)-4,6-dimethyl-1,2,3,4,9,9a-hexahydro-2,4a,5-triaza-fluorene This compound was prepared in analogy to example 1 from (4R,9aR)-7-(2-methoxy-ethoxy)-4,6-dimethyl-3,4,9,9a-tetrahydro-1H-2,4a,5-triaza-fluorene-2-carboxylic acid tert-butyl ester.

Light yellow oil (80.2%). ISP-MS: m/e=278.2 ([M+H$^+$])

Intermediate

(4R,9aR)-7-(2-Methoxy-ethoxy)-4,6-dimethyl-3,4,9,9a-tetrahydro-1H-2,4a,5-triaza-fluorene-2-carboxylic acid tert-butyl ester This compound was prepared in analogy to example 1 intermediate d), from (4R,9aR)-7-hydroxy-4,6-dimethyl-3,4,9,9a-tetrahydro-1H-2,4a,5-triaza-fluorene-2-carboxylic acid tert-butyl ester (example 7, intermediate), sodium hydride and 2-bromoethyl methyl ether.

Light yellow oil (67.0%). ISP-MS: m/e=378.4 ([M+H$^+$])

Example 13

(4R-9aR)-2-(4,6-Dimethyl-1,2,3,4,9,9a-hexahydro-2,4a,5-triaza-fluoren-7-yloxy)-ethanol This compound was prepared in analogy to example 1 from (4R,9aR)-7-(2-hydroxy-ethoxy)-4,6-dimethyl-3,4,9,9a-tetrahydro-1H-2,4a,5-triaza-fluorene-2-carboxylic acid tert-butyl ester.

Light yellow oil (88.0%). ISP-MS: m/e=264.2 ([M+H$^+$])

Intermediates a) (4R,9aR)-7-(2-Hydroxy-ethoxy)-4,6-dimethyl-3,4,9,9a-tetrahydro-1H-2,4a,5-triaza-fluorene-2-carboxylic acid tert-butyl ester To a stirred solution of 0.20 g (0.45 mmol) (4R,10aR)-4,6-dimethyl-7-[2-(tetrahydro-pyran-2-yloxy)-ethoxy]-3,4,9,9a-tetrahydro-1H-2,4a,5-triaza-fluorene-2-carboxylic acid tert-butyl ester in 3.0 mL methanol 0.17 g (0.89 mmol), p-toluenesulphonic acid was added. After 30 min., the solvent was evaporated and the residue was purified by flash column chromatography on silica gel (0.032–0.063 mm) with dichloromethane:methanol:ammonia (19:1:0.1) as eluant.

Light yellow foam (83.1%). ISP-MS: m/e=364.2 ([M+H$^+$])

b) (4R,10aR)-4,6-Dimethyl-7-[2-(tetrahydro-pyran-2-yloxy)-ethoxy]-3,4,9,9a-tetrahydro-1H-2,4a,5-triaza-fluorene-2-carboxylic acid tert-butyl ester This compound was prepared in analogy to example 1 intermediate d), from (4R,9aR)-7-hydroxy-4,6-dimethyl-3,4,9,9a-tetrahydro-1H-2,4a,5-triaza-fluorene-2-carboxylic acid tert-butyl ester (example 7, intermediate), sodium hydride and 2-(2-bromoethoxy)tetrahydro-2H-pyran.

Light yellow oil (43.1%). ISP-MS: m/e=448.5 ([M+H$^+$])

Example 14

(4R,9aR)-4,6,7-Trimethyl-1,2,3,4,9,9a-hexahydro-2,4a,5-triaza-fluorene

This compound was prepared in analogy to example 1 from (4R,9aR)-4,6,7-trimethyl-3,4,9,9a-tetrahydro-1H-2,4a,5-triaza-fluorene-2-carboxylic acid tert-butyl ester.

Light yellow solid (66.5%). ISP-MS: m/e=218.2 ([M+H$^+$])

Intermediate (4R,9aR)-4,6,7-Trimethyl-3,4,9,9a-tetrahydro-1H-2,4a,5-triaza-fluorene-2-carboxylic acid tert-butyl ester To a solution of 0.30 g (0.78 mmol) (4R,9aR)-7-bromo-4,6-dimethyl-3,4,9,9a-tetrahydro-1H-2,4a,5-triaza-fluorene-2-carboxylic acid tert-butyl ester (example 6, intermediate) in 15 mL dimethoxyethane was added 9 mg tetrakis(triphenylphosphine)palladium. After 20 min. 0.25 g (2.35 mmol) sodium carbonate in 8 mL water and 132 μl (0.94 mmol) trimethylboroxine were added and the reaction was stirred at 100° C. for 3 h. The reaction was cooled to room temperature then poured into 1M aqueous sodium hydroxide solution and extracted twice with ethyl acetate. The combined organic layers were washed with brine, dried over magnesium sulfate, filtered and evaporated. The residue was purified by column chromatography on silica gel with ethyl acetate:n-hexane (1:2) as eluant to give the product as a light yellow oil (66.0%).

ISP-MS: m/e=318.4 ([M+H$^+$])

Example 15

(4R,9aR)-7-Methoxymethyl-4,6-dimethyl-1,2,3,4,9,9a-hexahydro-2,4a,5-triaza-fluorene This compound was prepared in analogy to example 1 from (4R,9aR)-7-methoxymethyl-4,6-dimethyl-3,4,9,9a-tetrahydro-1H-2,4a,5-triaza-fluorene-2-carboxylic acid tert-butyl ester.

Light brown oil (99.8%). ISP-MS: m/e=248.2 ([M+H$^+$])

Intermediates a) (4R,9aR)-7-Methoxymethyl-4,6-dimethyl-3,4,9,9a-tetrahydro-1H-2,4a,5-triaza-fluorene-2-carboxylic acid tert-butyl ester This compound was prepared in analogy to example 1, intermediate d) from (4R,9aR)-7-hydroxymethyl-4,6-dimethyl-3,4,9,9a-tetrahydro-1H-2,4a,5-triaza-fluorene-2-carboxylic acid tert-butyl ester, sodium hydride and methyl iodide.

Light brown oil (53.3%). ISP-MS: m/e=348.5 ([M+H$^+$])

b) (4R,9aR)-7-Hydroxymethyl-4,6-dimethyl-3,4,9,9a-tetrahydro-1H-2,4a,5-triaza-fluorene-2-carboxylic acid tert-butyl ester To a solution of 90.0 mg (0.27 mmol) (4R,9aR)-7-formyl-4,6-dimethyl-3,4,9,9a-tetrahydro-1H-2,4a,5-triaza-fluorene-2-carboxylic acid tert-butyl ester in 1 mL methanol was added 6.2 mg (0.16 mmol) sodium borohydride. After 2 h the reaction mixture was poured into saturated aqueous sodium bicarbonate solution and extracted twice with ethyl acetate. The combined organic layers were washed with brine, dried over magnesium sulfate and filtered. The solvent was removed at a rotary evaporator and the residue was dried under high vacuum to give the compound as a light brown foam which was used without further purification (99.4%).

ISP-MS: m/e=334.3 ([M+H$^+$])

c) (4R,9aR)-7-Formyl-4,6-dimethyl-3,4,9,9a-tetrahydro-1H-2,4a,5-triaza-fluorene-2-carboxylic acid tert-butyl ester A solution of 0.41 g (1.07 mmol) (4R,9aR)-7-bromo-4,6-dimethyl-3,4,9,9a-tetrahydro-1H-2,4a,5-triaza-fluorene-2-carboxylic acid tert-butyl ester (example 6, intermediate) in 28 mL diethyl ether was cooled to −100° C. and treated with 0.80 mL (1.18 mmol) tert-butyl lithium (1.5M solution in n-pentane). After 15 min. 0.12 mL N,N-dimethylformamide was added and the temperature was raised to −78° C. After 45 min. the solution was poured into 10% aqueous ammonium chloride solution and extracted three times with ethyl acetate. The combined organic layers were washed with brine, dried over magnesium sulfate and filtered. The solvent was removed at a rotary evaporator and the residue was purified by column chromatography on silica gel (0.040–0.063 mm) with ethyl acetate:n-hexane (1:2) as eluant to give the compound as a yellow foam (80.2%).
ISP-MS: m/e=332.2 ([M+H$^+$])

Example 16

(4R,9aR)-7-Cyclopropylmethoxymethyl-4,6-dimethyl-1,2,3,4,9,9a-hexahydro-2,4a,5-triaza-fluorene This compound was prepared in analogy to example 1 from (4R,9aR)-7-cyclopropylmethoxymethyl-4,6-dimethyl-3,4,9,9a-tetrahydro-1H-2,4a,5-triaza-fluorene-2-carboxylic acid tert-butyl ester.
Yellow oil (80.9%). ISP-MS: m/e=288.2 ([M+H$^+$])

Intermediate (4R,9aR)-7-Cyclopropylmethoxymethyl-4,6-dimethyl-3,4,9,9a-tetrahydro-1H-2,4a,5-triaza-fluorene-2-carboxylic acid tert-butyl ester This compound was prepared in analogy to example 1 intermediate d) from (4R,9aR)-7-hydroxymethyl-4,6-dimethyl-3,4,9,9a-tetrahydro-1H-2,4a,5-triaza-fluorene-2-carboxylic acid tert-butyl ester (example 15, intermediate b), sodium hydride and (bromomethyl)cyclopropane.
Light yellow oil (72.8%). ISP-MS: m/e=388.3 ([M+H$^+$])

Example 17

(4R,9aR)-7-Chloro-6-ethyl-4-methyl-1,2,3,4,9,9a-hexahydro-2,4a,5-triaza-fluorene This compound was prepared in analogy to example 1 from (4R,9aR)-7-chloro-6-ethyl-4-methyl-3,4,9,9a-tetrahydro-1H-2,4a,5-triaza-fluorene-2-carboxylic acid tert-butyl ester.
Yellow oil (87.3%). ISP-MS: m/e=252.1 ([M+H$^+$])

Intermediates a) (4R,9aR)-7-Chloro-6-ethyl-4-methyl-3,4,9,9a-tetrahydro-1H-2,4a,5-triaza-fluorene-2-carboxylic acid tert-butyl ester This compound was prepared in analogy to example 5, intermediate from (4R,10aR)-6-ethyl-4-methyl-3,4,9,9a-tetrahydro-1H-2,4a,5-triaza-fluorene-2-carboxylic acid tert-butyl ester and N-chlorosuccinimide.
Yellow solid (72.2%). ISP-MS: m/e=352.3 ([M+H$^+$])

b) (4R,10aR)-6-Ethyl-4-methyl-3,4,9,9a-tetrahydro-1H-2,4a,5-triaza-fluorene-2-carboxylic acid tert-butyl ester To a solution of 0.70 g (1.90 mmol) (4R,9aR)-6-bromo-4-methyl-3,4,9,9a-tetrahydro-1H-2,4a,5-triaza-fluorene-2-carboxylic acid tert-butyl ester (example 5, intermediate c) in 14 mL N,N-dimethylformamide was added 73.0 mg [1,1'-bis(diphenyphosphino)ferrocene]-dichlorpalladium(II) and after 15 min. 4.8 mL of a 1M triethylborane solution in tetrahydrofuran and 0.79 g (5.70 mmol) potassium carbonate were added. After 4 h another 2.4 mL of triethylborane solution was added and the reaction mixture stirred overnight at 65 deg C. The suspension was poured into water and extracted twice with ethyl acetate. The combined organic phases were washed with brine, dried over magnesium sulfate, filtered and evaporated. The crude product was purified through column chromatography on silica gel (0.032–0.063 mm) with tert-butyl methyl ether:n-hexane (1:4) as eluent to yield the product as a colourless oil (89.5%).
ISP-MS: m/e=318.4 ([M+H$^+$])

Example 18

(4R,9aR)-7-Bromo-6-ethyl-4-methyl-1,2,3,4,9,9a-hexahydro-2,4a,5-triaza-fluorene

This compound was prepared in analogy to example 1 from (4R,9aR)-7-bromo-6-ethyl-4-methyl-3,4,9,9a-tetrahydro-1H-2,4a,5-triaza-fluorene-2-carboxylic acid tert-butyl ester.
Colourless oil (92.0%). ISP-MS: m/e=296.2 ([M+H$^+$])

Intermediate (4R,9aR)-7-Bromo-6-ethyl-4-methyl-3,4,9,9a-tetrahydro-1H-2,4a,5-triaza-fluorene-2-carboxylic acid tert-butyl ester This compound was prepared in analogy to example 6, intermediate from (4R,10aR)-6-ethyl-4-methyl-3,4,9,9a-tetrahydro-1H-2,4a,5-triaza-fluorene-2-carboxylic acid tert-butyl ester (example 17, intermediate b) and N-bromosuccinimide.
Colourless solid (92.9%). ISP-MS: m/e=396.3 ([M+H$^+$])

Example 19

(4R,9aR)-6-Ethyl-4,7-dimethyl-1,2,3,4,9,9a-hexahydro-2,4a,5-triaza-fluorene

This compound was prepared in analogy to example 1 from (4R,9aR)-6-ethyl-4,7-dimethyl-3,4,9,9a-tetrahydro-1H-2,4a,5-triaza-fluorene-2-carboxylic acid tert-butyl ester.
Light brown solid (92.9%). ISP-MS: m/e=232.1 ([M+H$^+$])

Intermediate (4R,9aR)-6-Ethyl-4,7-dimethyl-3,4,9,9a-tetrahydro-1H-2,4a,5-triaza-fluorene-2-carboxylic acid tert-butyl ester This compound was prepared in analogy to example 14, intermediate from (4R,9aR)-7-bromo-6-ethyl-4-methyl-3,4,9,9a-tetrahydro-1H-2,4a,5-triaza-fluorene-2-carboxylic acid tert-butyl ester.
Colourless solid (92.2%). ISP-MS: m/e=332.3 ([M+H$^+$])

Example 20

(4R,9aR)-6-Ethyl-7-methoxymethyl-4-methyl-3,4,9,9a-tetrahydro-1H-2,4a,5-triaza-fluorene-2-carboxylic acid tert-butyl ester This compound was prepared in analogy to example 1 from (4R,9aR)-6-ethyl-7-methoxymethyl-4-methyl-3,4,9,9a-tetrahydro-1H-2,4a,5-triaza-fluorene-2-carboxylic acid tert-butyl ester.
Light brown solid (76.7%). ISP-MS: m/e=262.2 ([M+H$^+$])

Intermediates a) (4R,9aR)-6-Ethyl-7-methoxymethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-ethyl-7-hydroxymethyl-4-methyl-3,4,9,9a-tetrahydro-1H-2,4a,5-triaza-fluorene-2-carboxylic acid tert-butyl ester, sodium hydride and methyl iodide.

Yellow oil (45.0%). ISP-MS: m/e=362.3 ([M+H$^+$])

b) (4R,9aR)-6-Ethyl-7-hydroxymethyl-4-methyl-3,4,9,9a-tetrahydro-1H-2,4a,5-triaza-fluorene-2-carboxylic acid tert-butyl ester This compound was prepared in analogy to example 15 intermediate b), from (4R,9aR)-6-ethyl-7-formyl-4-methyl-3,4,9,9a-tetrahydro-1H-2,4a,5-triaza-fluorene-2-carboxylic acid tert-butyl ester and sodium borohydride.

Brown solid (96.6%). ISP-MS: m/e=348.4 ([M+H$^+$])

c) (4R,9aR)-6-Ethyl-7-formyl-4-methyl-3,4,9,9a-tetrahydro-1H-2,4a,5-triaza-fluorene-2-carboxylic acid tert-butyl ester This compound was prepared in analogy to example 15, intermediate c) from (4R,9aR)-7-bromo-6-ethyl-4-methyl-3,4,9,9a-tetrahydro-1H-2,4a,5-triaza-fluorene-2-carboxylic acid tert-butyl ester.

Yellow solid (59.4%). ISP-MS: m/e=346.4 ([M+H$^+$])

Example 21

(4R,9aR)-7-Ethoxymethyl-6-ethyl-4-methyl-1,2,3,4,9,9a-hexahydro-2,4a,5-triaza-fluorene This compound was prepared in analogy to example 1 from (4R,9aR)-7-ethoxymethyl-6-ethyl-4-methyl-3,4,9,9a-tetrahydro-1H-2,4a,5-triaza-fluorene-2-carboxylic acid tert-butyl ester.

Colourless oil (88.0%). ISP-MS: m/e=276.3 ([M+H$^+$])

Intermediate (4R,9aR)-7-Ethoxymethyl-6-ethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-ethyl-7-hydroxymethyl-4-methyl-3,4,9,9a-tetrahydro-1H-2,4a,5-triaza-fluorene-2-carboxylic acid tert-butyl ester (example 20, intermediate b), sodium hydride and ethyl bromide.

Colourless solid (39.0%). ISP-MS: m/e=376.5 ([M+H$^+$])

Example 22

(4R,9aR)-7-Cyclopropylmethoxymethyl-6-ethyl-4-methyl-1,2,3,4,9,9a-hexahydro-2,4a,5-triaza-fluorene This compound was prepared in analogy to example 1 from (4R,9aR)-7-cyclopropylmethoxymethyl-6-ethyl-4-methyl-3,4,9,9a-tetrahydro-1H-2,4a,5-triaza-fluorene-2-carboxylic acid tert-butyl ester.

Yellow oil (83.9%). ISP-MS: m/e=302.3 ([M+H$^+$])

Intermediate (4R,9aR)-7-Cyclopropylmethoxymethyl-6-ethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-ethyl-7-hydroxymethyl-4-methyl-3,4,9,9a-tetrahydro-1H-2,4a,5-triaza-fluorene-2-carboxylic acid tert-butyl ester, sodium hydride and (bromomethyl)cyclopropane.

Yellow oil (28.2%). ISP-MS: m/e=402.5 ([M+H$^+$])

Example 23

(4R,9aR)-7-Chloro-6-difluoromethyl-4-methyl-1,2,3,4,9,9a-hexahydro-2,4a,5-triaza-fluorene This compound was prepared in analogy to example 1 from (4R,9aR)-7-chloro-6-difluoromethyl-4-methyl-3,4,9,9a-tetrahydro-1H-2,4a,5-triaza-fluorene-2-carboxylic acid tert-butyl ester.

Colourless oil (84.1%). ISP-MS: m/e=274.2 ([M+H$^+$])

Intermediates a) (4R,9aR)-7-Chloro-6-difluoromethyl-4-methyl-3,4,9,9a-tetrahydro-1H-2,4a,5-triaza-fluorene-2-carboxylic acid tert-butyl ester This compound was prepared in analogy to example 5, intermediate from (4R,9aR)-6-difluoromethyl-4-methyl-3,4,9,9a-tetrahydro-1H-2,4a,5-triaza-fluorene-2-carboxylic acid tert-butyl ester and N-chlorosuccinimide.

Light yellow solid (86.0%). ISP-MS: m/e=374.3 ([M+H$^+$])

b) (4R,9aR)-6-Difluoromethyl-4-methyl-3,4,9,9a-tetrahydro-1H-2,4a,5-triaza-fluorene-2-carboxylic acid tert-butyl ester To a solution of 83.0 µl (0.10 g, 0.63 mmol) diethylaminosulphur trifluoride in 3 mL dichloromethane 0.20 g (0.63 mmol) was added a solution of (4R,9aR)-6-formyl-4-methyl-3,4,9,9a-tetrahydro-1H-2,4a,5-triaza-fluorene-2-carboxylic acid tert-butyl ester dissolved in 3 mL dichloromethane; the reaction was stirred at room temperature for 5.5 h then heated to reflux. After 1 h at reflux temperature the reaction was cooled to room temperature, poured into water and extracted three times with ethyl acetate. The combined organic layers were washed with water and brine, dried over magnesium sulfate, filtered and evaporated. The residue was purified by flash column chromatography on silica gel (0.032–0.063 mm) with ethyl acetate:n-hexane (1:2) as eluant to give the desired compound as a light brown oil (28.1%).

ISP-MS: m/e=340.3 ([M+H$^+$])

c) (4R,9aR)-6-Formyl-4-methyl-3,4,9,9a-tetrahydro-1H-2,4a,5-triaza-fluorene-2-carboxylic acid tert-butyl ester A solution of 2.0 g (5.43 mmol) (4R,9aR)-6-bromo-4-methyl-3,4,9,9a-tetrahydro-1H-2,4a,5-triaza-fluorene-2-carboxylic acid tert-butyl ester (example 5, intermediate c) in 15 mL tetrahydrofuran was cooled to −75 deg C. and treated with 4.40 mL (0.65 mmol) tert-butyllithium (1.5 M solution in n-pentane). After 30 min., 0.60 mL (0.63 g, 8.15 mmol) N,N-dimethylformamide was added dropwise. After 2.5 h the reaction mixture was poured on 10% aqueous citric acid solution and extracted three times with ethyl acetate. The combined organic layers were washed with brine, dried over magnesium sulfate, filtered and evaporated. The remaining residue was purified by flash column chromatography on silica gel (0.032–0.063 mm) with ethyl acetate:n-hexane (1:3) as eluant to give the desired compound as a yellow oil (40.1%).

ISP-MS: m/e=319.5 ([M+H$^+$])

Example 24

(4R,9aR)-7-Bromo-6-difluoromethyl-4-methyl-1,2,3,4,9,9a-hexahydro-2,4a,5-triaza-fluorene This compound was prepared in analogy to example 1 from (4R,9aR)-7-bromo-6-difluoromethyl-4-methyl-3,4,9,9a-tetrahydro-1H-2,4a,5-triaza-fluorene-2-carboxylic acid tert-butyl ester.

Light brown oil (91.7%). ISP-MS: m/e=320.2 ([M+H$^+$])

Intermediate (4R,9aR)-7-Bromo-6-difluoromethyl-4-methyl-3,4,9,9a-tetrahydro-1H-2,4a,5-triaza-fluorene-2-carboxylic acid tert-butyl ester This compound was prepared in analogy to example 6, intermediate from (4R,9aR)-6-difluoromethyl-4-methyl-3,4,9,9a-tetrahydro-1H-2,4a,5-triaza-fluorene-2-carboxylic acid tert-butyl ester (example 23, intermediate b) and N-bromosuccinimide.

Light brown foam (92.2%). ISP-MS: m/e=420.3 ([M+H$^+$])

Example 25

(4R,9aR)-6-Difluoromethyl-4,7-dimethyl-1,2,3,4,9,9a-hexahydro-2,4a,5-triaza-fluorene This compound was prepared in analogy to example 1 from (4R,9aR)-6-difluoromethyl-4,7-dimethyl-3,4,9,9a-tetrahydro-1H-2,4a,5-triaza-fluorene-2-carboxylic acid tert-butyl ester.

Light yellow solid (94.4%). ISP-MS: m/e=254.1 ([M+H$^+$])

Intermediate (4R,9aR)-6-Difluoromethyl-4,7-dimethyl-3,4,9,9a-tetrahydro-1H-2,4a,5-triaza-fluorene-2-carboxylic acid tert-butyl ester This compound was prepared in analogy to example 14, intermediate from (4R,9aR)-7-bromo-6-difluoromethyl-4-methyl-3,4,9,9a-tetrahydro-1H-2,4a,5-triaza-fluorene-2-carboxylic acid tert-butyl ester (example 24, intermediate).

Colourless oil (63.9%). ISP-MS: m/e=354.4 ([M+H$^+$])

Example 26

(4R,9aR)-6-Difluoromethyl-7-methoxymethyl-4-methyl-1,2,3,4,9,9a-hexahydro-2,4a,5-triaza-fluorene This compound was prepared in analogy to example 1 from (4R,9aR)-6-difluoromethyl-7-methoxymethyl-4-methyl-3,4,9,9a-tetrahydro-1H-2,4a,5-triaza-fluorene-2-carboxylic acid tert-butyl ester.

Colourless oil (84.2%). ISP-MS: m/e=284.1 ([M+H$^+$])

Intermediates a) (4R,9aR)-6-Difluoromethyl-7-methoxymethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-difluoromethyl-7-hydroxymethyl-4-methyl-3,4,9,9a-tetrahydro-1H-2,4a,5-triaza-fluorene-2-carboxylic acid tert-butyl ester, sodium hydride and methyl iodide.

Colourless oil (31.0%). ISP-MS: m/e=384.3 ([M+H$^+$])

b) (4R,9aR)-6-Difluoromethyl-7-hydroxymethyl-4-methyl-3,4,9,9a-tetrahydro-1H-2,4a,5-triaza-fluorene-2-carboxylic acid tert-butyl ester This compound was prepared in analogy to example 15, intermediate b) from (4R,9aR)-6-difluoromethyl-7-formyl-4-methyl-3,4,9,9a-tetrahydro-1H-2,4a,5-triaza-fluorene-2-carboxylic acid tert-butyl ester and sodium borohydride.

Yellow solid (98.8%). ISP-MS: m/e=370.3 ([M+H$^+$])

c) (4R,9aR)-6-Difluoromethyl-7-formyl-4-methyl-3,4,9,9a-tetrahydro-1H-2,4a,5-triaza-fluorene-2-carboxylic acid tert-butyl ester This compound was prepared in analogy to example 15, intermediate c) from (4R,9aR)-7-bromo-6-difluoromethyl-4-methyl-3,4,9,9a-tetrahydro-1H-2,4a,5-triaza-fluorene-2-carboxylic acid tert-butyl ester (example 24, intermediate b).

Yellow solid (69.4%). ISP-MS: m/e=368.2 ([M+H$^+$])

Example 27

(4R,9aR)-6-Difluoromethyl-7-ethoxymethyl-4-methyl-1,2,3,4,9,9a-hexahydro-2,4a,5-triaza-fluorene This compound was prepared in analogy to example 1 from (4R,9aR)-6-difluoromethyl-7-ethoxymethyl-4-methyl-3,4,9,9a-tetrahydro-1H-2,4a,5-triaza-fluorene-2-carboxylic acid tert-butyl ester.

Colourless oil (89.1%). ISP-MS: m/e=298.3 ([M+H$^+$])

Intermediate (4R,9aR)-6-Difluoromethyl-7-ethoxymethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-difluoromethyl-7-hydroxymethyl-4-methyl-3,4,9,9a-tetrahydro-1H-2,4a,5-triaza-fluorene-2-carboxylic acid tert-butyl ester (example 26, intermediate b), sodium hydride and ethyl bromide.

Colourless oil (31.9%). ISP-MS: m/e=398.4 ([M+H$^+$])

Example 28

(4R,9aR)-7-Cyclopropylmethoxymethyl-6-difluoromethyl-4-methyl-1,2,3,4,9,9a-hexahydro-2,4a,5-triaza-fluorene This compound was prepared in analogy to example 1 from (4R,9aR)-7-cyclopropylmethoxymethyl-6-difluoromethyl-4-methyl-3,4,9,9a-tetrahydro-1H-2,4a,5-triaza-fluorene-2-carboxylic acid tert-butyl ester.

Yellow oil (90.5%). ISP-MS: m/e=324.3 ([M+H$^+$])

Intermediate (4R,9aR)-7-Cyclopropylmethoxymethyl-6-difluoromethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-difluoromethyl-7-hydroxymethyl-4-methyl-3,4,9,9a-tetrahydro-1H-2,4a,5-triaza-fluorene-2-carboxylic acid tert-butyl ester (example 26, intermediate b), sodium hydride and (bromomethyl) cyclopropane.

Light yellow oil (47.6%). ISP-MS: m/e=424.5 ([M+H$^+$])

Example 29

(4R,9aR)-7-Chloro-6-methoxy-4-methyl-1,2,3,4,9,9a-hexahydro-2,4a,5-triaza-fluorene This compound was prepared in analogy to example 1 from (4R,9aR)-7-chloro-6-methoxy-4-methyl-3,4,9,9a-tetrahydro-1H-2,4a,5-triaza-fluorene-2-carboxylic acid tert-butyl ester.

Yellow oil (98.5%). ISP-MS: m/e=254.1 ([M+H$^+$])

Intermediates a) (4R,9aR)-7-Chloro-6-methoxy-4-methyl-3,4,9,9a-tetrahydro-1H-2,4a,5-triaza-fluorene-2-carboxylic acid tert-butyl ester This compound was prepared in analogy to example 5, intermediate from (4R,9aR)-6-methoxy-4-methyl-3,4,9,9a-tetrahydro-1H-2,4a,5-triaza-fluorene-2-carboxylic acid tert-butyl ester and N-chlorosuccinimide.

Colourless foam (48.1%). ISP-MS: m/e=353.1 ([M])

b) (4R,9aR)-6-Methoxy-4-methyl-3,4,9,9a-tetrahydro-1H-2,4a,5-triaza-fluorene-2-carboxylic acid tert-butyl ester To a solution of 0.25 g (0.82 mmol) (4R,9aR)-6-hydroxy-4-methyl-3,4,9,9a-tetrahydro-1H-2,4a,5-triaza-fluorene-2-carboxylic acid tert-butyl ester in 2 mL N,N-dimethylformamide, 40 mg (0.90 mmol) sodium hydride (55–65% dispersion in oil) was added. After 30 min., 0.10 mL (0.23 g, 1.64 mmol) methyl iodide was added. After 1 h the reaction mixture was poured into water and extracted three times with ethyl acetate. The combined organic layers were washed twice with water, then brine and were dried over magnesium sulfate. After filtration and evaporation of the solvent the product was purified by column chromatography on silica gel (0.032–0.063 mm) with ethyl acetate:n-hexane (1:5) as eluant.

Colourless oil (80.3%). ISP-MS: m/e=320.4 ([M+H$^+$])

c) (4R,9aR)-6-Hydroxy-4-methyl-3,4,9,9a-tetrahydro-1H-2,4a,5-triaza-fluorene-2-carboxylic acid tert-butyl ester To a solution of 3.90 g (9.86 mmol) (4R,9aR)-6-benzyloxy-4-methyl-3,4,9,9a-tetrahydro-1H-2,4a,5-triaza-fluorene-2-carboxylic acid tert-butyl ester in 30 mL methanol: ethyl acetate (1:1 v/v) 0.20 g 10% palladium on charcoal was added; the reaction was stirred under hydrogen at atmospheric pressure for 2 h. After filtration over dicalite speed plus the filtrate was evaporated and the residue was purified by column chromatography on silica gel (0.032–0.063 mm) with ethyl acetate:n-hexane (1:1) as eluant to give the desired compound as a colourless foam (82.0%).

ISP-MS: m/e=306.4 ([M+H$^+$])

d) (4R,9aR)-6-Benzyloxy-4-methyl-3,4,9,9a-tetrahydro-1H-2,4a,5-triaza-fluorene-2-carboxylic acid tert-butyl ester To a solution of 3.0 g (8.15 mmol) (4R,9aR)-6-bromo-4-methyl-3,4,9,9a-tetrahydro-1H-2,4a,5-triaza-fluorene-2-carboxylic acid tert-butyl ester (example 5, intermediate c)) in 30 mL toluene were added 0.20 g (0.29 mmol) (S)-(−)-2,2'-bis(di-p-tolylphosphino)-1,1'-binaphthyl and 0.12 g (0.12 mmol) di-palladium-tris(dibenzylideneacetone)chloroform complex. After 30 min., 1.0 mL (1.06 g, 9.80 mmol) benzyl alcohol and 0.70 g (16.0 mmol) sodium hydride (55–65% dispersion in oil) were added and the reaction mixture was stirred for 3.5 h at 70 deg C. After cooling down to room temperature, the reaction mixture was poured into 10% aqueous sodium carbonate solution and extracted three times with ethyl acetate. The combined organic phases were washed with brine, dried over magnesium sulfate and filtered. After evaporation of the volatile components, the remaining residue was purified by column chromatography on silica gel (0.032–0.063 mm) with ethyl acetate:n-hexane (1:4) as eluant.

Yellow oil (62.0%). ISP-MS: m/e=396.4 ([M+H$^+$])

Example 30

(4R,9aR)-7-Bromo-6-methoxy-4-methyl-1,2,3,4,9,9a-hexahydro-2,4a,5-triaza-fluorene This compound was prepared in analogy to example 1 from (4R,9aR)-7-bromo-6-methoxy-4-methyl-3,4,9,9a-tetrahydro-1H-2,4a,5-triaza-fluorene-2-carboxylic acid tert-butyl ester.

Light brown oil (77.7%). ISP-MS: m/e=298.1 ([M+H$^+$])

Intermediate (4R,9aR)-7-Bromo-6-methoxy-4-methyl-3,4,9,9a-tetrahydro-1H-2,4a,5-triaza-fluorene-2-carboxylic acid tert-butyl ester This compound was prepared in analogy to example 6, intermediate from (4R,9aR)-6-methoxy-4-methyl-3,4,9,9a- tetrahydro-1H-2,4a,5-triaza-fluorene-2-carboxylic acid tert-butyl ester (example 29, intermediate b) and N-bromosuccinimide.

Colourless foam (95.2%). ISP-MS: m/e=400.3 ([M+H⁺])

Example 31

(4R,9aR)-6-Methoxy-4,7-dimethyl-1,2,3,4,9,9a-hexahydro-2,4a,5-triaza-fluorene

This compound was prepared in analogy to example 1 from (4R,9aR)-6-methoxy-4,7-dimethyl-3,4,9,9a-tetrahydro-1H-2,4a,5-triaza-fluorene-2-carboxylic acid tert-butyl ester.

Light yellow oil (71.5%). ISP-MS: m/e=234.2 ([M+H⁺])

Intermediate (4R,9aR)-6-Methoxy-4,7-dimethyl-3,4,9,9a-tetrahydro-1H-2,4a,5-triaza-fluorene-2-carboxylic acid tert-butyl ester This compound was prepared in analogy to example 14, intermediate from (4R,9aR)-7-bromo-6-methoxy-4-methyl-3,4,9,9a-tetrahydro-1H-2,4a,5-triaza-fluorene-2-carboxylic acid tert-butyl ester (example 30, intermediate).

Colourless oil (34.1%). ISP-MS: m/e=334.3 ([M+H⁺])

Example 32

(4R,9aR)-7-Chloro-6-ethoxy-4-methyl-1,2,3,4,9,9a-hexahydro-2,4a,5-triaza-fluorene This compound was prepared in analogy to example 1 from (4R,9aR)-7-chloro-6-ethoxy-4-methyl-3,4,9,9a-tetrahydro-1H-2,4a,5-triaza-fluorene-2-carboxylic acid tert-butyl ester.

Yellow oil (99.8%). ISP-MS: m/e=268.3 ([M+H⁺])

Intermediates a) (4R,9aR)-7-Chloro-6-ethoxy-4-methyl-3,4,9,9a-tetrahydro-1H-2,4a,5-triaza-fluorene-2-carboxylic acid tert-butyl ester This compound was prepared in analogy to example 5, intermediate) (4R,9aR)-6-ethoxy-4-methyl-3,4,9,9a-tetrahydro-1H-2,4a,5-triaza-fluorene-2-carboxylic acid tert-butyl ester and N-chlorosuccinimide.

Yellow oil (51.7%). ISP-MS: m/e=368.2 ([M+H⁺])

b) (4R,9aR)-6-Ethoxy-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-hydroxy-4-methyl-3,4,9,9a-tetrahydro-1H-2,4a,5-triaza-fluorene-2-carboxylic acid tert-butyl ester (example 29, intermediate c), sodium hydride and ethyl bromide.

Colourless oil (64.6%). ISP-MS: m/e=334.3 ([M+H⁺])

Example 33

(4R,9aR)-7-Bromo-6-ethoxy-4-methyl-1,2,3,4,9,9a-hexahydro-2,4a,5-triaza-fluorene This compound was prepared in analogy to example 1 from (4R,9aR)-7-bromo-6-ethoxy-4-methyl-3,4,9,9a-tetrahydro-1H-2,4a,5-triaza-fluorene-2-carboxylic acid tert-butyl ester.

Light brown oil (33.0%). ISP-MS: m/e=312.1 ([M+H⁺])

Intermediate (4R,9aR)-7-Bromo-6-ethoxy-4-methyl-3,4,9,9a-tetrahydro-1H-2,4a,5-triaza-fluorene-2-carboxylic acid tert-butyl ester This compound was prepared in analogy to example 6, intermediate from (4R,9aR)-6-ethoxy-4-methyl-3,4,9,9a-tetrahydro-1H-2,4a,5-triaza-fluorene-2-carboxylic acid tert-butyl ester (example 32, intermediate b) and N-bromosuccinimide.

Colourless oil (78.6%). ISP-MS: m/e=414.2 ([M+H⁺])

Example 34

(4R,9aR)-6-Ethoxy-4,7-dimethyl-1,2,3,4,9,9a-hexahydro-2,4a,5-triaza-fluorene

This compound was prepared in analogy to example 1 from (4R,9aR)-6-ethoxy-4,7-dimethyl-3,4,9,9a-tetrahydro-1H-2,4a,5-triaza-fluorene-2-carboxylic acid tert-butyl ester.

Light brown oil (81.3%). ISP-MS: m/e=248.2 ([M+H⁺])

Intermediate (4R,9aR)-6-Ethoxy-4,7-dimethyl-3,4,9,9a-tetrahydro-1H-2,4a,5-triaza-fluorene-2-carboxylic acid tert-butyl ester This compound was prepared in analogy to example 14, intermediate from (4R,9aR)-7-bromo-6-ethoxy-4-methyl-3,4,9,9a-tetrahydro-1H-2,4a,5-triaza-fluorene-2-carboxylic acid tert-butyl ester.

Light brown oil (31.0%). ISP-MS: m/e=348.4 ([M+H⁺])

Example 35

(4R,9aR)-7-Chloro-6-ethoxymethyl-4-methyl-1,2,3,4,9,9a-hexahydro-2,4a,5-triaza-fluorene This compound was prepared in analogy to example 1 from (4R,9aR)-7-chloro-6-ethoxymethyl-4-methyl-3,4,9,9a-tetrahydro-1H-2,4a,5-triaza-fluorene-2-carboxylic acid tert-butyl ester.

Light yellow oil (89.2%). ISP-MS: m/e=282.1 ([M+H⁺])

Intermediates a) (4R,9aR)-7-Chloro-6-ethoxymethyl-4-methyl-3,4,9,9a-tetrahydro-1H-2,4a,5-triaza-fluorene-2-carboxylic acid tert-butyl ester This compound was prepared in analogy to example 5, intermediate from (4R,9aR)-6-ethoxymethyl-4-methyl-3,4,9,9a-tetrahydro-1H-2,4a,5-triaza-fluorene-2-carboxylic acid tert-butyl ester and N-chlorosuccinimide.

Light yellow oil (70.6%). ISP-MS: m/e=382.3 ([M+H⁺])

b) (4R,9aR)-6-Ethoxymethyl-4-methyl-3,4,9,9a-tetrahydro-1H-2,4a,5-triaza-fluorene-2-carboxylic acid tert-butyl ester This compound was prepared in analogy to example 1 intermediate d), from (4R,10aR)-6-hydroxymethyl-4-methyl-3,4,9,9a-tetrahydro-1H-2,4a,5-triaza-fluorene-2-carboxylic acid tert-butyl ester, sodium hydride and ethyl bromide.

Light yellow oil (69.6%). ISP-MS: m/e=348.5 ([M+H$^+$])

c) (4R,10aR)-6-Hydroxymethyl-4-methyl-3,4,9,9a-tetrahydro-1H-2,4a,5-triaza-fluorene-2-carboxylic acid tert-butyl ester A solution of 4.2 g (12.1 mmol) (4R,10aR)-4-methyl-3,4,9,9a-tetrahydro-1H-2,4a,5-triaza-fluorene-2,6-dicarboxylic acid 2-tert-butyl ester 6-methyl ester in 100 mL tetrahydrofuran was cooled to 0 deg C. and treated dropwise with 48.4 mL diisobutylaluminium hydride (48.4 mmol; 1M solution in tetrahydrofuran). The cooling bath was removed and after 1 h at room temperature the reaction was quenched with a 10% aqueous potassium sodium tartrate solution then ethyl acetate was added. The two-phase system was filtered through a bed of dicalite speed plus; the filtrate was extracted with ethyl acetate and the organic phase was dried over magnesium sulphate. After filtration and evaporation the residue was purified by chromatography on silica gel (0.032–0.062 mm) with ethyl acetate as eluant to give the desired product as a light yellow foam (67.3%).

ISP-MS: m/e=320.4 ([M+H$^+$])

d) (4R,10aR)-4-Methyl-3,4,9,9a-tetrahydro-1H-2,4a,5-triaza-fluorene-2,6-dicarboxylic acid 2-tert-butyl ester 6-methyl ester To a solution of 6.0 g (16.3 mmol) (4R,10aR)-6-bromo-4-methyl-3,4,9,9a-tetrahydro-1H-2,4a,5-triaza-fluorene-2-carboxylic acid tert-butyl ester (example 5, intermediate c) in 60 mL methanol were added 0.57 g (0.50 mmol) tetrakis(triphenylphosphinyl)palladium and 3.4 mL (2.5 g, 24.4 mmol) triethylamine and the reaction mixture was stirred at 80° C. for 24 h under a carbon monoxide atmosphere of 40 bar. The suspension was cooled to room temperature, poured into a mixture of water, ethyl acetate and brine and was extracted with further portions of ethyl acetate. The combined organic layers were dried over magnesium sulfate and filtered. The residue was purified by chromatography on silica gel (0.032–0.063 mm) to give the product as a light yellow foam (74.4%).

ISP-MS: m/e=348.5 ([M+H$^+$])

Example 36

(4R,9aR)-7-Bromo-6-ethoxymethyl-4-methyl-1,2,3,4,9,9a-hexahydro-2,4a,5-triaza-fluorene This compound was prepared in analogy to example 1 from (4R,9aR)-7-bromo-6-ethoxymethyl-4-methyl-3,4,9,9a-tetrahydro-1H-2,4a,5-triaza-fluorene-2-carboxylic acid tert-butyl ester.

Light yellow oil (79.3%). ISP-MS: m/e=326.3 ([M+H$^+$])

Intermediate (4R,9aR)-7-Bromo-6-ethoxymethyl-4-methyl-3,4,9,9a-tetrahydro-1H-2,4a,5-triaza-fluorene-2-carboxylic acid tert-butyl ester This compound was prepared in analogy to example 6, intermediate from (4R,9aR)-6-ethoxymethyl-4-methyl-3,4,9,9a-tetrahydro-1H-2,4a,5-triaza-fluorene-2-carboxylic acid tert-butyl ester and N-bromosuccinimide.

Light yellow oil (68.7%). ISP-MS: m/e=428.5 ([M+H$^+$])

Example 37

(4R,9aR)-6-Ethoxymethyl-4,7-dimethyl-1,2,3,4,9,9a-hexahydro-2,4a,5-triaza-fluorene This compound was prepared in analogy to example 1 from (4R,9aR)-6-ethoxymethyl-4,7-dimethyl-3,4,9,9a-tetrahydro-1H-2,4a,5-triaza-fluorene-2-carboxylic acid tert-butyl ester.

Light yellow oil (83.0%). ISP-MS: m/e=262.2 ([M+H$^+$])

Intermediate (4R,9aR)-6-Ethoxymethyl-4,7-dimethyl-3,4,9,9a-tetrahydro-1H-2,4a,5-triaza-fluorene-2-carboxylic acid tert-butyl ester Light yellow oil (76.4%). ISP-MS: m/e=362.3 ([M+H$^+$])

Example 38

(4R,9aR)-7-Chloro-6-cyclopropylmethoxymethyl-4-methyl-1,2,3,4,9,9a-hexahydro-2,4a,5-triaza-fluorene This compound was prepared in analogy to example 1 from (4R,9aR)-7-chloro-6-cyclopropylmethoxymethyl-4-methyl-3,4,9,9a-tetrahydro-1H-2,4a,5-triaza-fluorene-2-carboxylic acid tert-butyl ester.

Light yellow oil (87.5%). ISP-MS: m/e=308.2 ([M+H$^+$])

Intermediate (4R,9aR)-7-Chloro-6-cyclopropylmethoxymethyl-4-methyl-3,4,9,9a-tetrahydro-1H-2,4a,5-triaza-fluorene-2-carboxylic acid tert-butyl ester This compound was prepared in analogy to example 5, intermediate from (4R,10aR)-6-cyclopropylmethoxymethyl-4-methyl-3,4,9,9a-tetrahydro-1H-2,4a,5-triaza-fluorene-2-carboxylic acid tert-butyl ester (synthesized in analogy to example 1, intermediate d) from (4R,10aR)-6-hydroxymethyl-4-methyl-3,4,9,9a-tetrahydro-1H-2,4a,5-triaza-fluorene-2-carboxylic acid tert-butyl ester (example 35, intermediate c), sodium hydride and (bromomethyl)cyclopropane) and N-chlorosuccinimide.

Light yellow oil (49.9%). ISP-MS: m/e=408.4 ([M+H$^+$])

Example 39

(4R,9aR)-7-Bromo-6-cyclopropylmethoxymethyl-4-methyl-1,2,3,4,9,9a-hexahydro-2,4a,5-triaza-fluorene This compound was prepared in analogy to example 1 from (4R,9aR)-7-bromo-6-cyclopropylmethoxymethyl-4-methyl-3,4,9,9a-tetrahydro-1H-2,4a,5-triaza-fluorene-2-carboxylic acid tert-butyl ester.

Light yellow oil (89.2%). ISP-MS: m/e=352.2 ([M+H$^+$])

Intermediate (4R,9aR)-7-Bromo-6-cyclopropylmethoxymethyl-4-methyl-3,4,9,9a-tetrahydro-1H-2,4a,5-triaza-fluorene-2-carboxylic acid tert-butyl ester This compound was prepared in analogy to example 6, intermediate from (4R,10aR)-6-cyclopropylmethoxymethyl-4-methyl-3,4,9,9a-tetrahydro-1H-2,4a,5-triaza-fluorene-2-carboxylic acid tert-butyl ester and N-bromosuccinimide.

Light yellow oil (74.6%). ISP-MS: m/e=454.4 ([M+H$^+$])

Example 40

(4R,9aR)-6-Cyclopropylmethoxymethyl-4,7-dimethyl-1,2,3,4,9,9a-hexahydro-2,4a,5-triaza-fluorene This compound was prepared in analogy to example 1 from (4R,9aR)-6-cyclopropylmethoxymethyl-4,7-dimethyl-3,4,9,9a-tetrahydro-1H-2,4a,5-triaza-fluorene-2-carboxylic acid tert-butyl ester.

Light yellow solid (91.4%). ISP-MS: m/e=288.2 ([M+H$^+$])

Intermediate (4R,9aR)-6-Cyclopropylmethoxymethyl-4,7-dimethyl-3,4,9,9a-tetrahydro-1H-2,4a,5-triaza-fluorene-2-carboxylic acid tert-butyl ester This compound was prepared in analogy to example 14, intermediate from (4R,9aR)-7-bromo-6-cyclopropylmethoxymethyl-4-methyl-3,4,9,9a-tetrahydro-1H-2,4a,5-triaza-fluorene-2-carboxylic acid tert-butyl ester (example 39, intermediate).

Light yellow oil (71.5%). ISP-MS: m/e=388.4 ([M+H$^+$])

Example 41

(4R,9aR)-6-Cyclopropylmethoxymethyl-4-methyl-1,2,3,4,9,9a-hexahydro-2,4a,5-triaza-fluoren-7-ol This compound was prepared in analogy to example 1 from (4R-9aR)-6-cyclopropylmethoxymethyl-7-hydroxy-4-methyl-3,4,9,9a-tetrahydro-1H-2,4a,5-triaza-fluorene-2-carboxylic acid tert-butyl ester.

Light yellow oil (58.3%). ISP-MS: m/e=290.2 ([M+H$^+$])

Intermediate (4R-9aR)-6-Cyclopropylmethoxymethyl-7-hydroxy-4-methyl-3,4,9,9a-tetrahydro-1H-2,4a,5-triaza-fluorene-2-carboxylic acid tert-butyl ester This compound was prepared in analogy to example 7, intermediate from (4R,9aR)-7-bromo-6-cyclopropylmethoxymethyl-4-methyl-3,4,9,9a-tetrahydro-1H-2,4a,5-triaza-fluorene-2-carboxylic acid tert-butyl ester (example 39, intermediate).

Light yellow solid (20.9%). ISP-MS: m/e=390.3 ([M+H$^+$])

Example 42

(4R,9aR)-6-Cyclopropylmethoxymethyl-7-methoxy-4-methyl-1,2,3,4,9,9a-hexahydro-2,4a,5-triaza-fluorene This compound was prepared in analogy to example 1 from (4R,9aR)-6-cyclopropylmethoxymethyl-7-methoxy-4-methyl-3,4,9,9a-tetrahydro-1H-2,4a,5-triaza-fluorene-2-carboxylic acid tert-butyl ester.

Light yellow oil (80.1%). ISP-MS: m/e=304.2 ([M+H$^+$])

Intermediate (4R,9aR)-6-Cyclopropylmethoxymethyl-7-methoxy-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-cyclopropylmethoxymethyl-7-hydroxy-4-methyl-3,4,9,9a-tetrahydro-1H-2,4a,5-triaza-fluorene-2-carboxylic acid tert-butyl ester (example 41, intermediate), methyl iodide and sodium hydride.

Light yellow oil (53.6%). ISP-MS: m/e=404.5 ([M+H$^+$])

Example 43

(4R,9aR)-6-Cyclopropylmethoxymethyl-7-ethoxy-4-methyl-1,2,3,4,9,9a-hexahydro-2,4a,5-triaza-fluorene This compound was prepared in analogy to example 1 from (4R,9aR)-6-cyclopropylmethoxymethyl-7-ethoxy-4-methyl-3,4,9,9a-tetrahydro-1H-2,4a,5-triaza-fluorene-2-carboxylic acid tert-butyl ester.

Light yellow oil (84.7%). ISP-MS: m/e=318.3 ([M+H$^+$])

Intermediate (4R,9aR)-6-Cyclopropylmethoxymethyl-7-ethoxy-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-6-cyclopropylmethoxymethyl-7-hydroxy-4-methyl-3,4,9,9a-tetrahydro-1H-2,4a,5-triaza-fluorene-2-carboxylic acid tert-butyl ester (example 41, intermediate), ethyl bromide and sodium hydride.

Light yellow oil (53.4%). ISP-MS: m/e=418.4 ([M+H$^+$])

Example 44

(4R,9aR)-7-Ethanesulfonyl-4,6-dimethyl-1,2,3,4,9,9a-hexahydro-2,4a,5-triaza-fluorene This compound was prepared in analogy to example 1 from (4R,9aR)-7-ethanesulfonyl-4,6-dimethyl-3,4,9,9a-tetrahydro-1H-2,4a,5-triaza-fluorene-2-carboxylic acid tert-butyl ester.

Colourless oil (56.2%). ISP-MS: m/e=296.2 ([M+H$^+$])

Intermediates a) (4R,9aR)-7-Ethanesulfonyl-4,6-dimethyl-3,4,9,
9a-tetrahydro-1H-2,4a,5-triaza-fluorene-2-carboxylic
acid tert-butyl ester A solution of 0.27 g (0.74 mmol) (4R,9aR)-7-ethylsulfanyl-4,6-dimethyl-3,4,9,9a-tetrahydro-1H-2,4a,5-triaza-fluorene-2-carboxylic acid tert-butyl ester in 5 mL methanol was treated with a solution of 1.77 g (1.11 mmol) potassium permanganate in 2.5 mL water. After 2 h dichloromethane and water were added and the suspension was filtered through dicalite speedex. The phases were separated and the aqueous layer was extracted twice with dichloromethane. The combined organic layers were washed with brine, dried over magnesium sulfate, filtered and evaporated. The residue was purified by column chromatography over silica gel (0.030–0.063 mm) with ethyl acetate:n-hexane (1:1) as eluant to give the product as a colourless oil (17.4%).
ISP-MS: m/e=396.3 ([M+H$^+$])

b) (4R,9aR)-7-Ethylsulfanyl-4,6-dimethyl-3,4,9,9a-
tetrahydro-1H-2,4a,5-triaza-fluorene-2-carboxylic
acid tert-butyl ester A solution of 0.50 g (1.31 mmol) (4R,9aR)-7-bromo-4,6-dimethyl-3,4,9,9a-tetrahydro-1H-2,4a,5-triaza-fluorene-2-carboxylic acid tert-butyl ester (example 6, intermediate) in 30 mL diethyl ether was cooled to −100° C. and 1.05 mL tert-butyl-lithium (1.57 mmol; 1.5M solution in n-pentane) was added dropwise. After 15 min. diethyl disulfide was added and the reaction was stirred at −78° C. for 1 h. The reaction mixture was quenched with 10% aqueous citric acid solution and extracted three times with ethyl acetate. The combined organic layers were washed with brine, dried over magnesium sulfate, filtered and evaporated. The residue was purified by column chromatography over silica gel (0.030–0.063 mm) with ethyl acetate:n-hexane (1:4) as eluant to give the product as a light yellow solid (57.2%).
ISP-MS: m/e=364.3 ([M+H$^+$])

Example 45

(4R,9aR)-6-Cyclopropylmethoxymethyl-7-ethoxymethyl-4-methyl-1,2,3,4,9,9a-hexahydro-2,4a,5-triaza-fluorene This compound was prepared in analogy to example 1 from (4R,9aR)-6-cyclopropylmethoxymethyl-7-methoxymethyl-4-methyl-3,4,9,9a-tetrahydro-1H-2,4a,5-triaza-fluorene-2-carboxylic acid tert-butyl ester.
Light yellow oil (78.1%). ISP-MS: m/e=332.3 ([M+H$^+$])

Intermediates a) (4R,9aR)-6-Cyclopropylmethoxymethyl-4-methyl-3,4,9,9a-tetrahydro-1H-2,4a,5-triaza-fluorene-2,
7-dicarboxylic acid 2-tert-butyl ester 7-methyl ester A mixture of 1.5 g (3.31 mmol) (4R,9aR)-7-bromo-6-cyclopropylmethoxymethyl-4-methyl-3,4,9,9a-tetrahydro-1H-2,4a,5-triaza-fluorene-2-carboxylic acid tert-butyl ester, 0.11 g (0.50 mmol) palladium(II) acetate, 0.68 g (1.66 mmol) 1,3-bis(diphenylphosphino)propane and 1.4 mL (1.0 g, 10.0 mmol) triethylamine in 15 mL MeOH was stirred for 48 h at 100° C. under a carbon monoxide atmosphere (50 bar). The reaction mixture was cooled to room temperature, filtered and partitioned between ethyl acetate and water. The organic phase was washed with brine, dried over magnesium sulphate, filtered and evaporated. The residue was purified by column chromatography over silica gel (0.030–0.063 mm) with ethyl acetate:n-hexane (1:3) as eluant to give the compound as a yellow oil (87%).
ISP-MS: m/e=432.4 ([M+H$^+$])

b) (4R,9aR)-6-Cyclopropylmethoxymethyl-7-hydroxymethyl-4-methyl-3,4,9,9a-tetrahydro-1H-2,4a,
5-triaza-fluorene-2-carboxylic acid tert-butyl ester This compound was prepared in analogy to example 35, intermediate c) from (4R,9aR)-6-cyclopropylmethoxymethyl-4-methyl-3,4,9,9a-tetrahydro-1H-2,4a,5-triaza-fluorene-2,7-dicarboxylic acid 2-tert-butyl ester 7-methyl ester and diisobutylaluminium hydride.
Light yellow oil (43.1%). ISP-MS: m/e=404.5 ([M+H$^+$])

c) (4R,9aR)-6-Cyclopropylmethoxymethyl-7-
ethoxymethyl-4-methyl-3,4,9,9a-tetrahydro-1H-2,4a,
5-triaza-fluorene-2-carboxylic acid tert-butyl ester This compound was prepared in analogy to example 1, intermediate d) from (4R,9aR)-6-cyclopropylmethoxymethyl-7-hydroxymethyl-4-methyl-3,4,9,9a-tetrahydro-1H-2,4a,5-triaza-fluorene-2-carboxylic acid tert-butyl ester, sodium hydride and ethyl bromide.
Light yellow oil (39.3%). ISP-MS: m/e=432.5 ([M+H$^+$])

Example 46

(4R,9aR)-7-Chloro-6-(1-(R)-methoxy-ethyl)-4-methyl-1,2,3,4,9,9a-hexahydro-2,4a,5-triaza-fluorene This compound was prepared in analogy to example 2 from (4R,9aR)-7-chloro-6-(1-(R)-methoxy-ethyl)-4-methyl-3,4,9,9a-tetrahydro-1H-2,4a,5-triaza-fluorene-2-carboxylic acid tert-butyl ester.
Light yellow solid (89.3%). ISP-MS: m/e=282.1 ([M+H$^+$])

Intermediates a) (4R,9aR)-7-Chloro-6-(1-(R)-methoxy-ethyl)-4-
methyl-3,4,9,9a-tetrahydro-1H-2,4a,5-triaza-fluorene-2-carboxylic acid tert-butyl ester This compound was prepared in analogy to example 5, intermediate from (4R,9aR)-6-(1-(R)-methoxy-ethyl)-4-methyl-3,4,9,9a-tetrahydro-1H-2,4a,5-triaza-fluorene-2-carboxylic acid tert-butyl ester and N-chlorosuccinimide.
Light yellow solid (49.6%). ISP-MS: m/e=382.3 ([M+H$^+$])

b) (4R,9aR)-6-(1-(R)-Methoxy-ethyl)-4-methyl-3,4,
9,9a-tetrahydro-1H-2,4a,5-triaza-fluorene-2-carboxylic acid tert-butyl ester To a solution of 0.75 g (2.25 mmol) (4R,9aR)-6-(1-(R)-hydroxy-ethyl)-4-methyl-3,4,9,9a-tetrahydro-1H-2,4a,5-triaza-fluorene-2-carboxylic acid tert-butyl ester in 5 mL N,N-dimethylformamide 0.12 g (2.70 mmol) sodium hydride (55–65% dispersion in oil) was added. After 30 min., 0.28 mL (0.64 g, 4.50 mmol) methyl iodide was added and the reaction mixture was stirred at 50 deg C. for 2 h. After cooling down to room temperature, the reaction mixture was poured into 10% aqueous ammonium chloride solution and extracted three times with ethyl acetate. The combined organic layers were washed with brine, dried over magnesium sulfate, filtered and evaporated. The residue was purified by column chromatography on silica gel (0.032–0.063 mm) with ethyl acetate:n-heptane (1:2) as eluant.

Yellow oil (89.6%). ISP-MS: m/e=348.4 (M+H$^+$)

c) (4R,9aR)-6-(1-(R)-Hydroxy-ethyl)-4-methyl-3,4,9,9a-tetrahydro-1H-2,4a,5-triaza-fluorene-2-carboxylic acid tert-butyl ester To a solution of 0.68 g (2.91 mmol) (4R,9aR)-6-(1-(R)-hydroxy-ethyl)-4-methyl-3,4,9,9a-tetrahydro-1H-2,4a,5-triaza-fluorene-2-carboxylic acid tert-butyl ester in 5 mL dichloromethane, 0.70 g (0.32 mmol) di-tert-butyldicarbonate and 17.8 mg (0.15 mmol) 4-(dimethylamino)pyridine were added. After 1 h the solvent was evaporated and the residue was purified by column chromatography on silica gel (0.032–0.063 mm) with ethyl acetate:n-heptane (1:2) as eluant.

Colourless foam (77.7%). ISP-MS: m/e=334.3 (M+H$^+$)

d) (4R,9aR)-6-(1-(R)-Hydroxy-ethyl)-4-methyl-3,4,9,9a-tetrahydro-1H-2,4a,5-triaza-fluorene-2-carboxylic acid tert-butyl ester A solution of 3.09 g (9.27 mmol) (4R,9aR)-6-(1-(RS)-hydroxy-ethyl)-4-methyl-3,4,9,9a-tetrahydro-1H-2,4a,5-triaza-fluorene-2-carboxylic acid tert-butyl ester in 33 mL dichloromethane was cooled to 0 deg C. and treated with 8.8 mL (12.7 g, 0.11 mol) trifluoroacetic acid. The cooling bath was removed and the volatile components were removed at a rotary evaporator. The remaining residue was purified by column chromatography on silica gel (0.032–0.063 mm) with dichloromethane:methanol:ammonia (19:1:0.1). The remaining oil was partitioned between dichloromethane and saturated aqueous sodium bicarbonate solution and extracted with dichloromethane until all product was removed from the aqueous phase. The combined organic layers were washed with brine, dried over magnesium sulfate, filtered and evaporated. The remaining light brown oil was purified by column chromatography on a Chiralpak-AD column with 7% ethanol/n-heptane yielding the desired compound as a light brown solid (36.5%).

ISP-MS: m/e=234.2 (M+H$^+$)

e) (4R,9aR)-6-(1-(RS)-Hydroxy-ethyl)-4-methyl-3,4,9,9a-tetrahydro-1H-2,4a,5-triaza-fluorene-2-carboxylic acid tert-butyl ester A solution of 6.0 g (16.3 mmol) (4R,9aR)-6-bromo-4-methyl-3,4,9,9a-tetrahydro-1H-2,4a,5-triaza-fluorene-2-carboxylic acid tert-butyl ester (example 5, intermediate c)) in 250 mL diethyl ether was cooled down to −100 deg C. and treated with 11.9 mL (17.9 mmol) tert-butyllithium (1.5 M in n-pentane). After 15 min., 1.0 mL (0.79 g, 17.9 mmol) acetaldehyde was added and the reaction was stirred for 40 min. at the same temperature. After warming to −75 deg C. the reaction mixture was poured into 10% aqueous ammonium chloride solution and extracted three times with ethyl acetate. The combined organic layers were washed with brine, dried over magnesium sulfate, filtered and evaporated. The residue was purified by column chromatography on silica gel (0.032–0.063 mm) with ethyl acetate:n-hexane (2:3) as eluant to give a first batch of compound. The remaining product-containing fractions were pooled and purified by column chromatography again to yield a second batch of compound (56.9% total).

Light brown oil. ISP-MS: m/e=334.3 (M+H$^+$)

Example 47

(4R,9aR)-7-Bromo-6-(1-(R)-methoxy-ethyl)-4-methyl-1,2,3,4,9,9a-hexahydro-2,4a,5-triaza-fluorene This compound was prepared in analogy to example 1 from (4R,9aR)-7-bromo-6-(1-(R)-methoxy-ethyl)-4-methyl-3,4,9,9a-tetrahydro-1H-2,4a,5-triaza-fluorene-2-carboxylic acid tert-butyl ester.

Light yellow solid (86.6%). ISP-MS: m/e=326.3 ([M+H$^+$])

Intermediate (4R,9aR)-7-Bromo-6-(1-(R)-methoxy-ethyl)-4-methyl-3,4,9,9a-tetrahydro-1H-2,4a,5-triaza-fluorene-2-carboxylic acid tert-butyl ester This compound was prepared in analogy to example 6, intermediate from (4R,9aR)-6-(1-(R)-methoxy-ethyl)-4-methyl-3,4,9,9a-tetrahydro-1H-2,4a,5-triaza-fluorene-2-carboxylic acid tert-butyl ester (example 46, intermediate b) and N-bromosuccinimide.

Yellow oil (98.3%). ISP-MS: m/e=428.4 ([M+H$^+$])

Example 48

(4R,9aR)-6-(1-(R)-Methoxy-ethyl)-4,7-dimethyl-1,2,3,4,9,9a-hexahydro-2,4a,5-triaza-fluorene This compound was prepared in analogy to example 1 from (4R,9aR)-6-(1-(R)-methoxy-ethyl)-4,7-dimethyl-3,4,9,9a-tetrahydro-1H-2,4a,5-triaza-fluorene-2-carboxylic acid tert-butyl ester.

Colourless solid (94.5%). ISP-MS: m/e=262.1 ([M+H$^+$])

Intermediate (4R,9aR)-6-(1-(R)-Methoxy-ethyl)-4,7-dimethyl-3,4,9,9a-tetrahydro-1H-2,4a,5-triaza-fluorene-2-carboxylic acid tert-butyl ester This compound was prepared in analogy to example 14, intermediate c) from (4R,9aR)-7-bromo-6-(1-(R)-methoxy-ethyl)-4-methyl-3,4,9,9a-tetrahydro-1H-2,4a,5-triaza-fluorene-2-carboxylic acid tert-butyl ester (example 47, intermediate).

Yellow solid (75.5%). ISP-MS: m/e=362.3 ([M+H$^+$])

Example 49

(4R,9aR)-6-(1-(R)-Methoxy-ethyl)-7-methoxymethyl-4-methyl-1,2,3,4,9,9a-hexahydro-2,4a,5-triaza-fluorene This compound was prepared in analogy to example 1 from (4R,9aR)-6-(1-(R)-methoxy-ethyl)-7-methoxymethyl-4-methyl-3,4,9,9a-tetrahydro-1H-2,4a,5-triaza-fluorene-2-carboxylic acid tert-butyl ester.

Colourless solid (82.1%). ISP-MS: m/e=292.4 ([M+H$^+$])

Intermediates a) (4R,9aR)-6-(1-(R)-Methoxy-ethyl)-7-methoxymethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-7-hydroxymethyl-6-(1-(R)-methoxy-ethyl)-4-methyl-3,4,9,9a-tetrahydro-1H-2,4a,5-triaza-fluorene-2-carboxylic acid tert-butyl ester, sodium hydride and methyl iodide.

Yellow oil (63.3%). ISP-MS: m/e=392.3 ([M+H$^+$])

b) (4R,9aR)-7-Hydroxymethyl-6-(1-(R)-methoxy-ethyl)-4-methyl-3,4,9,9a-tetrahydro-1H-2,4a,5-triaza-fluorene-2-carboxylic acid tert-butyl ester This compound was prepared in analogy to example 15, intermediate b) from (4R,9aR)-7-formyl-6-(1-(R)-methoxy-ethyl)-4-methyl-3,4,9,9a-tetrahydro-1H-2,4a,5-triaza-fluorene-2-carboxylic acid tert-butyl ester and sodium borohydride.

Light yellow solid (92.8%). ISP-MS: m/e=378.4 ([M+H$^+$])

c) (4R,9aR)-7-Formyl-6-(1-(R)-methoxy-ethyl)-4-methyl-3,4,9,9a-tetrahydro-1H-2,4a,5-triaza-fluorene-2-carboxylic acid tert-butyl ester This compound was prepared in analogy to example 15, intermediate c) from (4R,9aR)-7-bromo-6-(1-(R)-methoxy-ethyl)-4-methyl-3,4,9,9a-tetrahydro-1H-2,4a,5-triaza-fluorene-2-carboxylic acid tert-butyl ester.

Yellow foam (67.7%). ISP-MS: m/e=376.4 ([M+H$^+$])

Example 50

(4R,9aR)-7-Chloro-6-(1-(S)-methoxy-ethyl)-4-methyl-1,2,3,4,9,9a-hexahydro-2,4a,5-triaza-fluorene This compound was prepared in analogy to example 1 from (4R,9aR)-7-chloro-6-(1-(S)—methoxy-ethyl)-4-methyl-3,4,9,9a-tetrahydro-1H-2,4a,5-triaza-fluorene-2-carboxylic acid tert-butyl ester.

Light brown solid (83.4%). ISP-MS: m/e=282.1 ([M+H$^+$])

Intermediate (4R,9aR)-7-Chloro-6-(1-(S)-methoxy-ethyl)-4-methyl-3,4,9,9a-tetrahydro-1H-2,4a,5-triaza-fluorene-2-carboxylic acid tert-butyl ester This compound was prepared in analogy to example 5, intermediate from (4R,9aR)-6-(1-(S)-methoxy-ethyl)-4-methyl-3,4,9,9a-tetrahydro-1H-2,4a,5-triaza-fluorene-2-carboxylic acid tert-butyl ester (prepared in analogy to example 46 intermediates a) to e); the (4R,9aR)-6-(1-(S)-hydroxy-ethyl)-4-methyl-3,4,9,9a-tetrahydro-1H-2,4a,5-triaza-fluorene-2-carboxylic acid tert-butyl ester diastereomer is obtained during the chiral chromatography described under intermediate d) and N-chlorosuccinimide.

Yellow solid (76.1%). ISP-MS: m/e=382.3 ([M+H$^+$])

Example 51

(4R,9aR)-7-Bromo-6-(1-(S)-methoxy-ethyl)-4-methyl-1,2,3,4,9,9a-hexahydro-2,4a,5-triaza-fluorene This compound was prepared in analogy to example 1 from (4R,9aR)-7-bromo-6-(1-(S)-methoxy-ethyl)-4-methyl-3,4,9,9a-tetrahydro-1H-2,4a,5-triaza-fluorene-2-carboxylic acid tert-butyl ester.

Colourless solid (89.8%). ISP-MS: m/e=326.2 ([M+H$^+$])

Intermediate (4R,9aR)-7-Bromo-6-(1-(S)-methoxy-ethyl)-4-methyl-3,4,9,9a-tetrahydro-1H-2,4a,5-triaza-fluorene-2-carboxylic acid tert-butyl ester This compound was prepared in analogy to example 6 from (4R,9aR)-6-(1-(S)-methoxy-ethyl)-4-methyl-3,4,9,9a-tetrahydro-1H-2,4a,5-triaza-fluorene-2-carboxylic acid tert-butyl ester (example 40, intermediate b) and N-bromosuccinimide.

Light brown oil (82.2%). ISP-MS: m/e=428.5 ([M+H$^+$])

Example 52

(4R,9aR)-6-(1-(S)-Methoxy-ethyl)-4,7-dimethyl-1,2,3,4,9,9a-hexahydro-2,4a,5-triaza-fluorene This compound was prepared in analogy to example 1 from (4R,9aR)-6-(1-(S)-methoxy-ethyl)-4,7-dimethyl-3,4,9,9a-tetrahydro-1H-2,4a,5-triaza-fluorene-2-carboxylic acid tert-butyl ester.

Colourless solid (88.5%). ISP-MS: m/e=262.1 ([M+H$^+$])

Intermediate (4R,9aR)-6-(1-(S)-Methoxy-ethyl)-4,7-dimethyl-3,4,9,9a-tetrahydro-1H-2,4a,5-triaza-fluorene-2-carboxylic acid tert-butyl ester This compound was prepared in analogy to example 14, intermediate from (4R,9aR)-7-bromo-6-(1-(S)-methoxy-ethyl)-4-methyl-3,4,9,9a-tetrahydro-1H-2,4a,5-triaza-fluorene-2-carboxylic acid tert-butyl ester.

Yellow oil (76.7%). ISP-MS: m/e=362.2 ([M+H$^+$])

Example 53

(4R,9aR)-6-(1-(S)-Methoxy-ethyl)-7-methoxymethyl-4-methyl-1,2,3,4,9,9a-hexahydro-2,4a,5-triaza-fluorene This compound was prepared in analogy to example 1 from (4R,9aR)-6-(1-(S)-methoxy-ethyl)-7-methoxymethyl-4-methyl-3,4,9,9a-tetrahydro-1H-2,4a,5-triaza-fluorene-2-carboxylic acid tert-butyl ester Light brown solid (84.0%). ISP-MS: m/e=292.3 ([M+H$^+$])

Intermediates a) (4R,9aR)-6-(1-(S)-Methoxy-ethyl)-7-methoxymethyl-4-methyl-3,4,9,9a-tetrahydro-1H-2,4a,5-triaza-fluorene-2-carboxylic acid tert-butyl ester This compound was prepared in analogy to example 1, intermediate d) from (4R,9aR)-7-hydroxymethyl-6-(1-(S)- methoxy-ethyl)-4-methyl-3,4,9,9a-tetrahydro-1H-2,4a,5-triaza-fluorene-2-carboxylic acid tert-butyl ester, sodium hydride and methyl iodide.

Light brown solid (85.7%). ISP-MS: m/e=392.3 ([M+H$^+$])

b) (4R,9aR)-7-Hydroxymethyl-6-(1-(S)-methoxy-ethyl)-4-methyl-3,4,9,9a-tetrahydro-1H-2,4a,5-triaza-fluorene-2-carboxylic acid tert-butyl ester This compound was prepared in analogy to example 15, intermediate b) from (4R,9aR)-7-formyl-6-(1-(S)-methoxy-ethyl)-4-methyl-3,4,9,9a-tetrahydro-1H-2,4a,5-triaza-fluorene-2-carboxylic acid tert-butyl ester and sodium borohydride.

Light yellow solid (95.9%). ISP-MS: m/e=378.4 ([M+H$^+$])

c) (4R,9aR)-7-Formyl-6-(1-(S)-methoxy-ethyl)-4-methyl-3,4,9,9a-tetrahydro-1H-2,4a,5-triaza-fluorene-2-carboxylic acid tert-butyl ester This compound was prepared in analogy to example 15, intermediate c) from (4R,9aR)-7-bromo-6-(1-(S)-methoxy-ethyl)-4-methyl-3,4,9,9a-tetrahydro-1H-2,4a,5-triaza-fluorene-2-carboxylic acid tert-butyl ester (example 51, intermediate).

Yellow foam (67.2%). ISP-MS: m/e=376.4 ([M+H$^+$])

Example 54

(R)-7-Fluoro-4-methyl-1,2,3,4-tetrahydro-2,4a,5-triaza-fluorene hydrochloride A mixture of 0.152 g R-[2-(5-fluoro-2-hydroxymethyl-pyrrolo[2,3-b]pyridin-1-yl)-propyl]-carbamic acid tert-butyl ester and 2 mL of a 2.3 M solution of hydrochloric acid in ethyl acetate was stirred at room temperature for 5 h. The precipitate was collected by filtration, washed with ethyl acetate and dried to yield 0.12 g (R)-7-fluoro-4-methyl-1,2,3,4-tetrahydro-2,4a,5-triaza-fluorene hydrochloride (100% th) m.p.: 235–237° C.

Example 55

(4R,9aR)-7-Fluoro-4-methyl-1,2,3,4,9,9a-hexahydro-2,4a,5-triaza-fluorene

A solution of 0.138 g (4R,9aR)-7-fluoro-4-methyl-3,4,9,9a-tetrahydro-1H-2,4a,5-triaza-fluorene-2-carboxylic acid tert-butyl ester in 1.5 mL trifluoroacetic acid was kept at room temperature for 1 h. The solvent was evaporated and the residue was purified by chromatography on silica gel with dichloromethane:methanol:sat. ammonia (9:1:0.1) to yield 0.070 g (4R,9aR)-7-fluoro-4-methyl-1,2,3,4,9,9a-hexahydro-2,4a,5-triaza-fluorene as slightly yellow oil.

ISP-MS: m/e=208.4 ([M+H$^+$])

Example 56

(4R,9aR)-(7-Fluoro-4-methyl-1,2,3,4,9,9a-hexahydro-2,4a,5-triaza-fluoren-6-yl)-methanol A solution of 0.020 g (4R,9aR)-7-fluoro-6-hydroxymethyl-4-methyl-3,4,9,9a-tetrahydro-1H-2,4a,5-triaza-fluorene-2-carboxylic acid tert-butyl ester in 2N hydrochloric acid in dioxane was kept at room temperature for 18 h. The solvent was evaporated and the residue was purified by chromatography on silica gel with dichloromethane:methanol:satd. ammonia (9:1:0.1) to yield 0.011 g (4R,9aR)-(7-fluoro-4-methyl-1,2,3,4,9,9a-hexahydro-2,4a,5-triaza-fluoren-6-yl)-methanol as brownish crystals.

ISP-MS: m/e=238.3 ([M+H$^+$])

Example 57

(4R,9aR)-6-Cyclopropylmethoxymethyl-7-fluoro-4-methyl-1,2,3,4,9,9a-hexahydro-2,4a,5-triaza-fluorene To a solution of (4R,9aR)-7-fluoro-6-hydroxymethyl-4-methyl-3,4,9,9a-tetrahydro-1H-2,4a,5-triaza-fluorene-2-carboxylic acid tert-butyl ester in 3.3 mL dimethylformamide was added portionwise 0.100 g sodium hydride (55% in oil) and 0.27 g cyclopropyl bromide and the mixture was stirred at room temperature for 8 h. The reaction mixture was partitioned between water and ethyl acetate and the concentrated organic phase was purified by chromatography on silica gel with heptane:ethyl acetate=1:1 to yield 0.144 g of a slightly yellow oil which was taken up in 1.5 mL trifluoroacetic acid and kept at room temperature for 1 h. The solvent was evaporated and the residue was purified by chromatography on silica gel with dichloromethane:methanol:satd. ammonia (9:1:0.1) to yield 0.095 g (4R,9aR)-6-cyclopropylmethoxymethyl-7-fluoro-4-methyl-1,2,3,4,9,9a-hexahydro-2,4a,5-triaza-fluorene as a yellow orange oil.

ISP-MS: m/e=292.4 ([M+H$^+$])

Example 58

(4R,9aR)-7-Fluoro-4-methyl-1,2,3,4,9,9a-hexahydro-2,4a,5-triaza-fluorene-6-carbaldehyde O-methyl-oxime To a solution of 0.047 g (4R,9aR)-7-fluoro-6-formyl-4-methyl-3,4,9,9a-tetrahydro-1H-2,4a,5-triaza-fluorene-2-carboxylic acid tert-butyl ester in 1 mL ethanol was added 0.014 g O-methylhydroxylamine hydrochloride and the mixture was stirred at ambient for 18 temperature for 18 h. The reaction mixture was partitioned between water and ethyl acetate. The organic phase was washed with 10% citric acid, 10% sodium bicarbonate and brine, then concentrated and purified by chromatography on silica gel with heptane:ethyl acetate=2:1. The product was treated with 1 mL trifluoroacetic acid at room temperature for 30 min. The solvent was evaporated and the residue was purified by chromatography on silica gel with dichloromethane:methanol:satd. ammonia (9:1:0.1) to yield 0.027 g (4R,9aR)-7-fluoro-4-methyl-1,2,3,4,9,9a-hexahydro-2,4a,5-triaza-fluorene-6-carbaldehyde O-methyl-oxime as a light yellow solid.

ISP-MS: m/e=265.3 ([M+H$^+$])

Example 59

1-(S)-[(4R,9aR)-7-fluoro-4-methyl-1,2,3,4,9,9a-hexahydro-2,4a,5-triaza-fluoren-6-yl]-ethanol A solution of 0.010 g (4R,9aR)-7-fluoro-6-[1-(R)-hydroxy-ethyl]-4-methyl-3,4,9,9a-tetrahydro-1H-2,4a,5-triaza-fluorene-2-carboxylic acid tert-butyl ester in 1 mL dioxane and 0.1 mL 2M hydrochloric acid was kept at room temperature for 30 min. The solvent was evaporated and the residue was purified by chromatography on silica gel with dichloromethane:methanol:ammonia (100:10:1) to yield 0.005 g 1-(S)-[(4R,9aR)-7-fluoro-4-methyl-1,2,3,4,9,9a-hexahydro-2,4a,5-triaza-fluoren-6-yl]-ethanol as a colorless gum.

ISP-MS: m/e=252.3 ([M+H$^+$])

Example 60

(4R,9aR)-6-[1-(S)-Cyclopropylmethoxy-ethyl]-7-fluoro-4-methyl-1,2,3,4,9,9a-hexahydro-2,4a,5-triaza-fluorene The compound was obtained in an analogous way as in example 57 starting from (4R,9aR)-7-fluoro-6-[1-(S)-hydroxy-ethyl]-4-methyl-3,4,9,9a-tetrahydro-1H-2,4a,5-triaza-fluorene-2-carboxylic acid tert-butyl ester as a slightly orange oil.

ISP-MS: m/e=306.3 ([M+H$^+$])

Example 61

(E)-[4R,9aR]-1-(7-fluoro-4-methyl-1,2,3,4,9,9a-hexahydro-2,4a,5-triaza-fluoren-6-yl)-ethanone O-methyl-oxime The compound was obtained in an analogous way as in example 58 starting from [4R,9R]-6-acetyl-7-fluoro-4-methyl-3,4,9,9a-tetrahydro-1H-2,4a,5-triaza-fluorene-2-carboxylic acid tert-butyl ester as a beige crystalline powder; m.p.: 128–130° C.

Intermediates (Examples 54–61)

a) N-(5-Fluoro-pyridin-2-yl)-2,2-dimethyl-propionamide

To a solution of 33.6 mL triethylamine and 22.5 2-amino-5-fluoropyridine (0.201 mol) in 200 mL dichloromethane was added dropwise a solution of 28 mL pivaloyl chloride (0.201 mol) in 50 mL dichloromethane at such a rate that the temperature did not exceed 15° C. (ice bath cooling). The mixture was then stirred overnight with thawing to room temperature. The resulting brown-black suspension was added 5 g charcoal and the mixture was stirred at room temperature for 30 min and filtered through dicalite. The orange-yellow mother liquor was purified by filtration over a layer of silica gel (400 g) with heptane:ethyl acetate=4:1. The slightly yellow product fractions were evaporated and the oily residue was distilled in a kugelrohr apparatus at 100° C. and 0.5 mbar. The compound crystallized on standing at room temperature.

Yield: 33.400 g N-(5-fluoro-pyridin-2-yl)-2,2-dimethyl-propionamide as colorless crystals (84.8%); m.p.: 33.4–35.2° C.

b) N-(5-Fluoro-3-iodo-pyridin-2-yl)-2,2-dimethyl-propionamide

To a solution of 33 g of freshly distilled N-(5-fluoro-pyridin-2-yl)-2,2-dimethyl-propionamide (0.168 mol) in 500 mL tert-butylmethylether at −78° C. was added dropwise 323 mL of a ca. 1.3 M solution of sec BuLi (0.42 mol) in cyclohexane at a rate that the temperature did not exceed −60° C. (liquid nitrogen cooling; ca 5 min). The mixture was stirred at −78° C. for 30 min. To the resulting light yellow suspension was added dropwise a solution of 107 g iodine (0.420 mol) in 150 mL tetrahydrofuran at a rate that the temperature did not exceed −65° C. (liquid nitrogen cooling; ca 5 min). The mixture was then stirred at −78° C. for 2 h. To the resulting suspension was added a 10% sodium thiosulfate solution in water (800 mL) and the phases were separated. The organic phase was washed with a 10% solution of sodium thiosulfate in water, 10% citric acid solution in water, 10% sodium bicarbonate solution in water and brine, dried over magnesium sulfate and concentrated under aspirator vacuum whereby crystallisation occurred. The solid was collect by filtration and washed with cyclohexane and air-dried to constant weight.

Yield: 43.50 g (80%) N-(5-fluoro-3-iodo-pyridin-2-yl)-2,2-dimethyl-propionamide as white crystals; m.p.: 141–142.8° C.

c) 5-Fluoro-3-iodo-pyridin-2-ylamine

A mixture of 43.00 g (0.133 mol) N-(5-fluoro-3-iodo-pyridin-2-yl)-2,2-dimethyl-propionamide in 400 mL 2N sulfuric acid was heated to reflux for 1.5 h. The reaction mixture was cooled to room temperature and extracted with dichloromethane. The aqueous phase was mixed with dichloromethane and the pH was adjusted to 12 by addition of 25% aqueous sodium hydroxide. The phases were separated and the organic phase was washed with half-concentrated brine, dried with magnesium sulfate and evaporated to dryness.

Yield: 31.3 g 5-fluoro-3-iodo-pyridin-2-ylamine as white crystals (98% th); m.p.: 75.7–77.5° C.

d) 2-[Dimethyl-(1,1,2-trimethyl-propyl)-silanyloxymethyl]-5-fluoro-1H-pyrrolo [2,3-b]pyridine To a solution of 0.29 g 5-fluoro-3-iodo-pyridin-2-ylamine (0.0012 mol) in 5 mL dichloromethane at 0° C. was added dropwise 0.30 mL trifluoroacetic acid anhydride ((0.00145 mol). The mixture was stirred at room temperature for 30 min. The reaction mixture was partitioned between dichloromethane and pH 7.00 buffer (Merck titrisol); the organic phase was washed with 10% aqueous sodium bicarbonate and brine, dried over magnesium sulfate and evaporated to dryness to yield the trifluoroacetate as a white crystalline solid (275 mg). A mixture of 0.004 g copper iodide (0.00002 mol) and 0.007 g bis(triphenylphosphine)palladium dichloride (0.00001 mol) in 5 mL triethylamine was heated to reflux under argon for 30 min. The resulting yellow solution was cooled to room temperature and the crystalline trifluoroacetate and 0.264 g dimethyl-prop-2-ynyloxy-(1,1,2-trimethyl-propyl)-silane (0.0013 mol) was added at once and heating under reflux was continued for 4 h. The dark reaction mixture was partitioned between 10% aqueous citric acid and ethyl acetate and the organic phase was purified by chromatography on silica gel with heptane:ethyl acetate=3:1 then crystallisation from methanol to yield 0.176g. 2-[dimethyl-(1,1,2-trimethyl-propyl)-silanyoxymethyl]-5-fluoro-1H-pyrrolo [2,3-b]pyridine as white crystals; m.p.: 56.6–58.4° C.

e) (R)-(2-{2-[Dimethyl-(1,1,2-trimethyl-propyl)-silanyloxymethyl]-5-fluoro-pyrrolo [2,3-b]pyridin-1-yl}-propyl)-carbamic acid tert-butyl ester To a solution of 0.31 g 2-[dimethyl-(1,1,2-trimethyl-propyl)-silanyloxymethyl]-5-fluoro-1H-pyrrolo[2,3-b]pyridine (0.001 mol) in 5 mL dimethylformamide was added 0.048 sodium hydride 55% in oil (0.0011 mol) and the mixture was stirred at room temperature for 15 min. To the slightly yellow solution was added 0.286g (S)-5-methyl-2, 2-dioxo-2[1,2,3]oxathiazolidine-3-carboxylic acid tert-butyl ester (0.0012 mol) and the mixture was stirred at room temperature for 18 h. The mixture was diluted with ethyl acetate and 10% aqueous citric acid. The phases were separated and the organic phase was washed with sodium bicarbonate and brine, dried over magnesium sulfate, concentrated and purified by chromatography on silica gel with heptane:ethyl acetate=3:1 to yield 0.426 g R-(2-{2-[dimethyl-(1,1,2-trimethyl-propyl)-silanyoxymethyl]-5-fluoro-pyrrolo [2,3-b]pyridin-1-yl}-propyl)-carbamic acid tert-butyl ester (91%) as colorless gum.

ISP-MS: m/e=466.5 ([M+H$^+$])

f) R-[2-(5-Fluoro-2-hydroxymethyl-pyrrolo [2,3-b] pyridin-1-yl)-propyl]-carbamic acid tert-butyl ester A mixture of 0.42 g R-(2-{2-[dimethyl-(1,1,2-trimethyl-propyl)-silanyloxymethyl]-5-fluoro-pyrrolo[2,3-b]pyridin-1-yl}-propyl)-carbamic acid tert-butyl ester and 0.42 g ammonium fluoride in 10 mL methanol was heated to reflux for 18 h. The reaction mixture was partitioned between water and ethyl acetate. The organic phase was washed with brine and dried over magnesium sulfate, evaporated to dryness and purified by chromatography on silica gel with heptane:ethyl acetate=1:1 as eluent to yield 0.280 g R-[2-(5-fluoro-2-hydroxymethyl-pyrrolo[2,3-b]pyridin-1-yl)-propyl]-carbamic acid tert-butyl ester as colorless gum (96%).

ISP-MS: m/e=324.5 ([M+H$^+$])

g) (R)-7-Fluoro-4-methyl-3,4-dihydro-1H-2,4a,5-triaza-fluorene-2-carboxylic acid tert-butyl ester To a solution of 5.4 g (R)-[2-(5-fluoro-2-hydroxymethyl-pyrrolo[2,3-b]pyridin-1-yl)-propyl]-carbamic acid tert-butyl ester in 55 mL dichloromethane was added 7.40 g manganese dioxide and the mixture was stirred at room temperature for 1 h. Another 7.40 g manganese dioxide was added and the mixture was stirred at room temperature for 4 h. The solids were removed by filtration over dicalite. The mother liquor was evaporated and the residue was taken up in 50 mL dichloromethane and 3.0 mL acetic acid and 10.62 g sodium triacetoxyborohydride was added. An instantaneous gas evolution took place and the mixture warmed up to ca 35° C. The mixture was stirred at ambient temperature for 18 h. To the reaction mixture was added 50 mL water. A marked gas evolution took place. The mixture was stirred at room temperature for 15 min. The phases were separated and the organic phase was evaporated to dryness and purified by chromatography on silica gel with heptane:ethyl acetate=1:1 as eluent to yield a slightly yellow oil which crystallized on standing to yield 3.80 g (R)-7-fluoro-4-methyl-3,4-dihydro-1H-2,4a,5-triaza-fluorene-2-carboxylic acid tert-butyl ester as slightly yellow crystals; m.p.: 85–87° C.

h) (4R,9aR)-7-Fluoro-4-methyl-3,4,9,9a-tetrahydro-1H-2,4a,5-triaza-fluorene-2-carboxylic acid tert-butyl ester T a solution of 0.907 g (R)-7-fluoro-4-methyl-3,4-dihydro-1H-2,4a,5-triaza-fluorene-2-carboxylic acid tert-butyl ester (0.0030 mol) in 12 mL of glacial acetic acid was added in 2 portions 0.936 g sodium cyanoborohydride (0.015 mol) with cooling. The mixture was then stirred at ambient temperature for 2 h. The solvent was evaporated and the residue was partitioned between water (adjusted to pH 10–11 by addition of aqueous sodium hydroxide solution) and dichloromethane. The organic phase was evaporated to dryness then purified by chromatography on silica gel with heptane:ethyl acetate (2:1) to yield a slightly yellow oil which solidified on standing to yield 0.852g [4R,9aR]-7-fluoro-4-methyl-3,4,9,9a-tetrahydro-1H-2,4a,5-triaza-fluorene-2-carboxylic acid tert-butyl ester (94% th) slightly yellow crystals; m.p.: 56.6–58.4° C.

i) (4R,9aR)-7-Fluoro-6-formyl-4-methyl-3,4,9,9a-tetrahydro-1H-2,4a,5-triaza-fluorene-2-carboxylic acid tert-butyl ester and (4R,9aR)-7-fluoro-8-formyl-4-methyl-3,4,9,9a-tetrahydro-1H-2,4a,5-triaza-fluorene-2-carboxylic acid tert-butyl ester To a solution of 2.885 g (4R,9aR)-7-fluoro-4-methyl-3,4,9,9a-tetrahydro-1H-2,4a,5-triaza-fluorene-2-carboxylic acid tert-butyl ester in 60 mL toluene at −78° C. was added 8.72 mL of a ca. 1.3 M solution of sec. butyl lithium in cyclohexane over 10 min. The orange mixture was stirred at −78° C. for 30 min. To the resulting viscous solution was added 1.00 mL dimethylformamide and the mixture was stirred at −78° C. for 1.5 h. To the reaction mixture was added 100 mL of a 10% citric acid solution in water. The phases were separated and the organic phase was evaporated to dryness and purified by chromatography on silica gel with heptane:ethyl acetate=2:1 to yield 0.585 g (4R,9aR)7-fluoro-6-formyl-4-methyl-3,4,9,9a-tetrahydro-1H-2,4a,5-triaza-fluorene-2-carboxylic acid tert-butyl ester as yellow-orange crystals; m.p.: 139–140° C. and 0.800 g (4R,9aR)-7-Fluoro-8-formyl-4-methyl-3,4,9,9a-tetrahydro-1H-2,4a,5-triaza-fluorene-2-carboxylic acid tert-butyl ester.

ISP-MS: m/e=336.3 ([M+H$^+$]).

j) [4R,9aR]-6-Acetyl-7-fluoro -4-methyl-3,4,9,9a-tetrahydro-1H-2,4a,5-triaza-fluorene-2-carboxylic acid tert-butyl ester In the same manner as above was prepared (4R,9aR)-6-acetyl-7-fluoro-4-methyl-3,4,9,9a-tetrahydro-1H-2,4a,5-triaza-fluorene-2-carboxylic acid tert-butyl ester by substituting dimethylformamide with dimethylacetamide. The product was obtained as yellow crystals; m.p. 178–180° C.

k) (4R,9aR)-7-Fluoro-6-hydroxymethyl-4-methyl-3,4,9,9a-tetrahydro-1H-2,4a,5-triaza-fluorene-2-carboxylic acid tert-butyl ester To a solution of 0.58 g (4R,9aR)-7-fluoro-6-formyl-4-methyl-3,4,9,9a-tetrahydro-1H-2,4a,5-triaza-fluorene-2-carboxylic acid tert-butyl ester in 10 mL tetrahydrofuran was added 0.038 g lithium borohydride and the mixture was stirred at room temperature for 30 min. The reaction mixture was partitioned between water and ethyl acetate. The phases were separated and the organic phase was evaporated to dryness and purified by chromatography on silica gel with heptane:ethyl acetate=1:1 to yield 0.468 g (4R,9aR)-7-fluoro-6-hydroxymethyl-4-methyl-3,4,9,9a-tetrahydro-1H-2,4a,5-triaza-fluorene-2-carboxylic acid tert-butyl ester as yellowish crystals; m.p.: 91–93° C.

Example 62

(4R,9aR)-7-Bromo-6-fluoromethyl-4-methyl-1,2,3,4,9,9a-hexahydro-2,4a,5-triaza-fluorene di-trifluoroacetate

(4R,9aR)-7-Bromo-6-fluoromethyl-4-methyl-1,2,3,4,9,9a-hexahydro-1H-2,4a,5-triaza-fluorene-2-carboxylic acid tert-butyl ester To a stirred solution of (4R,9aR)-6-fluoromethyl-4-methyl-1,2,3,4,9,9a-hexahydro-1H-2,4a,5-triaza-fluorene-2-carboxylic acid tert-butyl ester (1.0 g) in tetrahydrofuran (25 mL) was added N-bromosuccinimide (0.61 g). The mixture was stirred for 2 h then concentrated in vacuo. The residue was purified by flash column chromatography [$SiO_2$; isohexane-ethyl acetate (4:1)] to give (4R,9aR)-7-bromo-6-fluoromethyl-4-methyl-1,2,3,4,9,9a-hexahydro-1H-2,4a,5-triaza-fluorene-2-carboxylic acid tert-butyl ester as a yellow oil (0.84 g); NMR $\delta_H$(400 MHz, $CDCl_3$) 7.29 (1H, s), 5.45 (1H, t, J 11 Hz), 5.33 (1H, t, J 11 Hz), 4.35 (1H, m), 4.22 (1H, m), 4.00 (2H, m), 3.85 (1H, m), 3.04 (2H, m), 2.60 (2H, m), 1.48 (9H, s) and 1.23 (3H, d, J 7 Hz); m/z $M^+$ 400, 402, 403 (M+1).

(4R,9aR)-7-Bromo-6-fluoromethyl-4-methyl-1,2,3,4,9,9a-hexahydro-2,4a,5-triaza-fluorene di-trifluoroacetate A mixture of (4R,9aR)-7-bromo-6-fluoromethyl-4-methyl-1,2,3,4,9,9a-hexahydro-1H-2,4a,5-triaza-fluorene-2-carboxylic acid tert-butyl ester (0.050 g), trifluoroacetic acid (1 mL) and dichloromethane (1 mL) was left to stand for 1 h then concentrated in vacuo to give (4R,9aR)-7-bromo-6-fluoromethyl-4-methyl-1,2,3,4,9,9a-hexahydro-2,4a,5-triaza-fluorene di-trifluoroacetate as an orange oil (0.073 g); NMR $\delta_H$ (400 MHz, $CDCl_3$) 9.21 (1H, m), 8.76 (1H, m), 7.60 (1H, d, J 1 Hz), 5.39 (1H, dd, J 12, 10.5 Hz), 5.27 (1H, dd, J 12, 10.5 Hz), 4.43 (1H, dt, J 12.5, 7 Hz), 4.16 (1H, tdd, J 12, 5.5, 3.5 Hz), 3.30 (1H, dd, J 12, 2 Hz), 3.21 (1H, d, J 12 Hz), 3.17 (1H, m), 3.08 (1H, dt, J 12,4 Hz), 2.89 (1H, q, J 12 Hz), 2.74 (1H, ddt, J 17, 5, 1.5 Hz) and 1.30 (3H, d, J 7 Hz).

Example 63

(4R,9aR)-6-Chloro-7-fluoro-4-methyl-1,2,3,4,9,9a-hexahydro-2,4a,5-triaza-fluorene To a solution of 0.23 g (4R,9aR)-7-fluoro-4-methyl-3,4,9,9a-tetrahydro-1H-2,4a,5-triaza-fluorene-2-carboxylic acid tert-butyl ester (intermediate h of examples 54–61) in 5 mL toluene was added dropwise at −78° C. 1.4 mL of a ca 1.3 M solution of t-butyllithium in pentane. The mixture was stirred at −78° C. for 30 min. To the resulting mixture was added 0.3 g hexachloroethane and the mixture was stirred at −78° C. for 30 min and then allowed to thaw to 0° C. over ca 30 min. The reaction was quenched with 10% citric acid and the organic phase was separated and evaporated and the residue purified by chromatography on silica gel with heptane:ethyl acetate (4:1). The product fractions containing the two isomers and some starting material were evaporated and the residue was taken up in 1 mL trifluoroacetic acid and kept at room temperature for 30 min. The solvent was evaporated and the residue was purified by chromatography on silica gel with dichloromethane:methanol:ammonia (9:1:0.1). The product fractions containing the more polar isomer were collected evaporated and dried under high vacuum to yield 0.016 g (4R,9aR)-6-chloro-7-fluoro-4-methyl-1,2,3,4,9,9a-hexahydro-2,4a,5-triaza-fluorene as light brown gum.

ISP-MS: m/e=242.3 ([$M+H^+$])

Example 64

(4R,9aR)-6-Fluoromethyl-7-iodo-4-methyl-1,2,3,4,9,9a-hexahydro-2,4a,5-triaza-fluorene di-trifluoroacetate To a solution of (4R,9aR)-6-fluoromethyl-4-methyl-1,2,3,4,9,9a-hexahydro-1H-2,4a,5-triaza-fluorene-2-carboxylic acid tert-butyl ester (56 mg) in tetrahydrofuran (2 mL) was added N-iodosuccinimide (44 mg). The mixture was shaken for 24 h then a further portion of N-iodosuccinimide (22 mg) was added. The mixture was shaken for 24 h then concentrated in vacuo. The residue was dissolved in ethyl acetate (5 mL). The resulting solution was filtered through a pad of silica (1 g), washing with more ethyl acetate (5 mL). The filtrate was concentrated in vacuo. The residue was dissolved in dichloromethane (2 mL) and trifluoroacetic acid (1 mL), left to stand for 1 h then concentrated in vacuo. The residue was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50% methanol to 100%, 0 to 10 min then 100% methanol to 13 min, 20 mL/min) to give (4R,9aR)-6-fluoromethyl-7-iodo-4-methyl-1,2,3,4,9,9a-hexahydro-2,4a,5-triaza-fluorene di-trifluoroacetate as a yellow oil (13 mg); NMR $\delta_H$ (400 MHz, DMSO-$d_6$) 9.34 (1H, m), 8.92 (1H, m), 7.73 (1H, d, J 1 Hz), 5.39 (1H, app s), 5.27 (1H, app s), 4.41 (1H, m), 4.16 (1H, m), 3.29 (1H, m), 3.19 (1H, d, J 12 Hz), 3.14 (1H, m), 3.05 (1H, m), 2.86 (1H, qd, J 12, 1.5 Hz), 2.71 (1H, dt, J 17, 5 Hz) and 1.31 (3H, d, J 7 Hz); m/z $M^+$ 348 (M+1).

Example 65

(4R,9aR)-6-fluoromethyl-7-ethoxymethyl-4-methyl-1,2,3,4,9,9a-hexahydro-2,4a,5-triaza-fluorene di-trifluoroacetate

(4R,9aR)-6-fluoromethyl-7-formyl-4-methyl-1,2,3,4,9,9a-hexahydro-1H-2,4a,5-triaza-fluorene-2-carboxylic acid tert-butyl ester To a stirred solution of n-butyl lithium/hexanes (2.5M, 0.44 mL) in dry tetrahydrofuran (15 mL) at −78° C. under inert atmosphere was added dropwise a solution of (4R,9aR)-7-bromo-6-fluoromethyl-4-methyl-1,2,3,4,9,9a-hexahydro-1H-2,4a,5-triaza-fluorene-2-carboxylic acid tert-butyl ester (0.40 g) in dry tetrahydrofuran (5 mL). The mixture was stirred for 45 minutes then dimethyl formamide (0.78 mL) was added. The mixture was stirred for 2 hours then warmed to room temperature and stirred for a further 2 hours. The mixture was partitioned between aqueous ammonium chloride solution (30 mL) and ethyl acetate (50 mL). The organic phase was washed (water, brine), dried (magnesium sulfate), filtered and concentrated in vacuo. The residue was purified by flash column chromatography [$SiO_2$; isohexane-ethyl acetate (4:1)→(3:1)] to give (4R,9aR)-6-fluoromethyl-7-formyl-4-methyl-1,2,3,4,9,9a-hexahydro-1H-2,4a,5-triaza-fluorene-2-carboxylic acid tert-butyl ester (0.080 g); NMR $\delta_H$ (400 MHz, $CDCl_3$) 10.07 (1H, d, J 1.5 Hz), 7.67 (1H, s), 5.68 (1H, dd, J 17.5, 11.5 Hz), 5.56 (1H, dd, J 17.5, 11.5 Hz), 4.53 (1H, m), 4.32 (1H, m), 4.12 (2H, m), 3.95 (1H, m), 3.13 (1H, dd, J 16.5, 9 Hz), 3.03 (1H, m), 2.65 (2H, m), 1.49 (9H, s) and 1.27 (3H, d, J 7 Hz).

(4R,9aR)-6-fluoromethyl-7-hydroxymethyl-4-methyl-1,2,3,4,9,9a-hexahydro-1H-2,4a,5-triaza-fluorene-2-carboxylic acid tert-butyl ester To a stirred solution of (4R,9aR)-6-fluoromethyl-7-formyl-4-methyl-1,2,3,4,9,9a-hexahydro-1H-2,4a,5-triaza-fluorene-2-carboxylic acid tert-butyl ester (0.080 g) in ethanol (2 mL) was added sodium borohydride (9 mg). The mixture was stirred for 90 minutes then partitioned between water (10 mL) and dichloromethane (10 mL). The organic layer was washed with brine, dried over magnesium sulfate, filtered and concentrated in vacuo. The residue was purified by column chromatography [SiO$_2$; isohexane-ethyl acetate (1:1)] to give (4R,9aR)-6-fluoromethyl-7-hydroxymethyl-4-methyl-1,2,3,4,9,9a-hexahydro-1H-2,4a,5-triaza-fluorene-2-carboxylic acid tert-butyl ester as a white solid (0.054 g); NMR $\delta_H$ (400 MHz, CDCl$_3$) 7.26 (1H, s), 5.48 (1H, dd, J 12, 10.5 Hz), 5.36 (1H, dd, J 12, 10.5 Hz), 4.60 (2H, d, J2 Hz), 4.37 (1H, m), 4.19 (1H, m), 3.99 (1H, tdd, J 11.5, 6, 4 Hz), 3.87 (1H, m), 3.04 (1H, ddd, J 16, 8.5, 4 Hz), 2.98 (1H, m), 2.62 (1H, m), 2.54 (1H, dt, J 16.5, 4.5 Hz), 1.48 (9H, s) and 1.23 (3H, d, J 6.5 Hz).

(4R,9aR)-6-Fluoromethyl-7-ethoxymethyl-4-methyl-1,2,3,4,9,9a-hexahydro-2,4a,5-triaza-fluorene di-trifluoroacetate To a solution of (4R,9aR)-6-fluoromethyl-7-hydroxymethyl-4-methyl-1,2,3,4,9,9a-hexahydro-1H-2,4a,5-triaza-fluorene-2-carboxylic acid tert-butyl ester (0.027 g) in N,N-dimethylformamide (1 mL) was added sodium hydride (60%, 0.0035 g). The mixture was shaken for 25 minutes then iodoethane (0.012 mL) was added. The mixture was shaken for 24 hours then partitioned between aqueous sodium hydrogen carbonate solution (10 mL) and dichloromethane (10 mL). The organic phase was concentrated in vacuo; the residue was purified by reverse phase preparative HPLC (Prep Nova-Pak HR C18 6 mm 60 Å 30 mm×300 mm column, UV detection at 254 nm, mobile phase 95:5 methanol:water and 10 mmol ammonium acetate, gradient 50% methanol to 100%, 0 to 10 min then 100% methanol to 13 min, 20 mL/min) to give a pale yellow oil (0.013 g). The oil was dissolved in dichloromethane (1 mL) and trifluoroacetic acid (1 mL) and left to stand for 1 h. The mixture was concentrated in vacuo to give (4R,9aR)-6-fluoromethyl-7-ethoxymethyl-4-methyl-1,2,3,4,9,9a-hexahydro-2,4a,5-triaza-fluorene di-trifluoroacetate as a yellow oil (0.029 g); NMR $\delta_H$ (400 MHz, DMSO-d$_6$) 9.19 (1H, m), 8.76 (1H, m), 7.39 (1H, s), 7.10 (2H, t, J51 Hz), 5.38 (1H, dd, J 12, 10.5 Hz), 5.26 (1H, dd, J 12, 10.5 Hz), 4.46 (1H, dt, J 11.5, 7 Hz), 4.39 (2H, d, J 2 Hz), 4.13 (1H, tdd, J 12, 6, 3.5 Hz), 3.46 (2H, q, J 7 Hz), 3.30 (1H, d, J 11.5 Hz), 3.21 (1H, d, J 12.5 Hz), 3.14 (1H, m), 3.07 (1H, m), 2.85 (1H, q, J 11 Hz), 2.71 (1H, dt, J 16.5, 4.5 Hz), 1.31 (3H, d, J 7 Hz) and 1.12 (3H, t, J 7 Hz).

Example 66

(4R,9aR)-6-Fluoromethyl-7-4-methoxyphenyl-4-methyl-1,2,3,4,9,9a-hexahydro-2,4a,5-triaza-fluorene di-hydrochloride To a solution of (4R,9aR)-7-bromo-6-fluoromethyl-4-methyl-1,2,3,4,9,9a-hexahydro-1H-2,4a,5-triaza-fluorene-2-carboxylic acid tert-butyl ester (0.050 g) in dimethoxyethane (2 mL) was added tetrakis(triphenylphosphine)palladium(0) (14 mg). The mixture was left to stand for 5 minutes then aqueous sodium carbonate solution (0.4 M, 1 mL) and 4-methoxyphenylboronic acid (0.038 g) were added. The mixture was heated to 160° C. for 4 minutes under microwave irradiation then cooled to room temperature. The mixture was partitioned between dichloromethane (10 mL) and saturated aqueous sodium hydrogen carbonate solution (10 mL). The organic layer was concentrated in vacuo. The residue was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50% methanol to 100%, 0 to 10 min then 100% methanol to 13 min, 20 mL/min) to give a yellow solid (0.023 g). The solid was dissolved in dichloromethane (1 mL) and trifluoroacetic acid (1 mL). The mixture was left to stand for 1 hour then concentrated in vacuo. The residue was dissolved in dichloromethane (2 mL); the resultant solution was washed with aqueous ammonia solution, concentrated in vacuo and purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50% methanol to 100%, 0 to 10 min then 100% methanol to 13 min, 20 mL/min). The residue was dissolved in HCl-dioxane (4M, 0.1 mL), then concentrated in vacuo to give (4R,9aR)-6-fluoromethyl-7-4-methoxyphenyl-4-methyl-1,2,3,4,9,9a-hexahydro-2,4a,5-triaza-fluorene di-hydrochloride as a yellow solid (0.022 g); NMR $\delta_H$ (400 MHz, DMSO-d$_6$) 9.57 (1H, m), 9.17 (1H, m), 7.39 (1H, s), 7.25 (2H, dt, J 8.5, 2.5 Hz), 7.01 (2H, dt, J 8.5, 2.5 Hz), 5.21 (1H, dd, J 13, 10 Hz), 5.09 (1H, dd, J 13, 10 Hz), 4.57 (1H, m), 4.24 (1H, m), 3.80 (3H, s), 3.33 (1H, m), 3.21 (2H, m), 3.10 (1H, m), 2.88 (1H, q, J 11 Hz), 2.77 (1H, dt, J 17, 4.5 Hz) and 1.37 (3H, d, J 7 Hz).

Example 67

(4R,9aR)-7-Bromo-6-ethanesulfanyl-4-methyl-1,2,3,4,9,9a-hexahydro-1H-2,4a,5-triaza-fluorene

(4R,9aR)-6-Ethylsulfanyl-4-methyl-3,4,9,9a-tetrahydro-1H-2,4a,5-triaza-fluorene-2-carboxylic acid tert-butyl ester A solution of n-butyl lithium (1.6 M in hexanes, 0.5 mL, 0.8 mmol) in tetrahydrofuran (5 mL) was stirred at −78° C. for 5 min. under an argon atmosphere. A mixture of (4R,9aR)-6-bromo-4-methyl-3,4,9,9a-tetrahydro-1H-2,4a,5-triaza-fluorene-2-carboxylic acid tert-butyl ester (0.2 g, 0.54 mmol) in tetrahydrofuran (5 mL) was added dropwise, maintaining the temperature below −70° C. The resultant dark red solution was left to stir at −78° C. for 30 min then ethyl disulfide (0.13 mL, 1.08 mmol) was added. The mixture was left to stir at −78° C. for 2 h, then left to warm to room temperature over 2 h. Water (1 mL) was added and the mixture was poured onto an isolute HM-N SPE cartridge and eluted with ethyl acetate (10 mL). The eluent was evaporated under reduced pressure and the crude material was purified by reverse phase preparative HPLC (Prep Nova-Pak HR C18 6 mm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give the title compound (0.071 g, 53% yield) as a pale yellow oil: m/z M$^+$ 350.14 (M+1); HPLC (50% to 80%

(4R,9aR)-7-Bromo-6-ethanesulfanyl-4-methyl-1,2,3,4,9,9a-hexahydro-1H-2,4a,5-triaza-fluorene-2-carboxylic acid tert-butyl ester To a solution of (4R,9aR)-6-ethanesulfanyl-4-methyl-1,2,3,4,9,9a-hexahydro-1H-2,4a,5-triaza-fluorene-2-carboxylic acid tert-butyl ester (10 mg) in tetrahydrofuran (1 mL) was added a solution of N-bromosuccinimide (5.3 mg) in tetrahydrofuran (0.5 mL). The mixture was shaken for 18 h then partitioned between dichloromethane (3 mL) and water (2 mL). The organic layer was filtered through a PTFE frit; the filtrate was concentrated in vacuo. The residue was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give (4R,9aR)-7-bromo-6-ethanesulfanyl-4-methyl-1,2,3,4,9,9a-hexahydro-1H-2,4a,5-triaza-fluorene-2-carboxylic acid tert-butyl ester as a yellow oil (4.2 mg); NMR $\delta_H$ (400 MHz, CDCl$_3$) 7.18 (1H, t, J 1 Hz), 4.29 (1H, tdd, J 8.5, 4.5, 1.5 Hz), 4.16 (1H, m), 3.96 (1H, m), 3.89 (1H, m), 3.11 (2H, qd, J 7.5, 2.5 Hz), 3.04 (1H, m), 2.97 (1H, qd, J 8.5, 1 Hz), 2.67 (1H, m), 2.49 (1H, ddd, J 16, 6, 1 Hz), 1.48 (9H, s), 1.36 (3H, t, J 7.5 Hz) and 1.23 (3H, d, J 7 Hz); m/z M$^+$ 428, 430 (M+1).

(4R,9aR)-7-Bromo-6-ethanesulfanyl-4-methyl-1,2,3,4,9,9a-hexahydro-1 H-2,4a,5-triaza-fluorene A solution of (4R,9aR)-6-ethanesulfanyl-4-methyl-1,2,3,4,9,9a-hexahydro-1H-2,4a,5-triaza-fluorene-2-carboxylic acid tert-butyl ester in dichloromethane (1 mL) and trifluoroacetic acid (1 mL) was shaken for 18 h then concentrated in vacuo. The residue was dissolved in methanol (1 mL) and loaded onto an ion-exchange column (SCX-2, 1 g). The column was washed with methanol (5 mL) then with methanolic ammonia solution (7N, 5 mL). The ammonia washings were concentrated in vacuo to give (4R,9aR)-7-bromo-6-ethanesulfanyl-4-methyl-1,2,3,4,9,9a-hexahydro-1H-2,4a,5-triaza-fluorene as a brown oil (1.8 mg); NMR $\delta_H$ (400 MHz, CDCl$_3$) 7.26 (1H, s), 4.53 (1H, m), 4.24 (1H, m), 3.22 (1H, dd, J 12,3 Hz), 3.13 (2H, m), 3.10 (1H, dd,J7.5, 3 Hz), 3.08 (1H, m), 2.80 (1H, t,J12 Hz), 2.56 (1H, dd, J 16,6 Hz), 1.46 (3H, d, J7 Hz) and 1.37 (3H, t, J7.5 Hz).

Example 68

(4R,9aR)-7-Bromo-6-propanesulfanyl-4-methyl-1,2,3,4,9,9a-hexahydro-1H-2,4a,5-triaza-fluorene

(4R,9aR)-4-Methyl-6-propylsulfanyl-3,4,9,9a-tetrahydro-1H-2,4a,5-triaza-fluorene-2-carboxylic acid tert-butyl ester This was prepared according to the method described for Example 67 using (4R,9aR)-6-bromo-4-methyl-3,4,9,9a-tetrahydro-1H-2,4a,5-triaza-fluorene-2-carboxylic acid tert-butyl ester and propyl disulfide to produce 0.053 g (27% yield) of the product as a pale yellow oil: m/z M$^+$ 364.21 (M+1); HPLC (50% to 80% gradient [95:5 MeOH:water, 10 mmol ammonium acetate] 220 nm XTERRA 2.0 mL/min) 6.94 min.

(4R,9aR)-7-Bromo-6-propanesulfanyl-4-methyl-1,2,3,4,9,9a-hexahydro-1H-2,4a,5-triaza-fluorene-2-carboxylic acid tert-butyl ester (4R,9aR)-7-Bromo-6-propanesulfanyl-4-methyl-1,2,3,4,9,9a-hexahydro-1H-2,4a,5-triaza-fluorene-2-carboxylic acid tert-butyl ester was prepared from (4R,9aR)-6-propanesulfanyl-4-methyl-1,2,3,4,9,9a-hexahydro-1H-2,4a,5-triaza-fluorene (10 mg) and N-bromosuccinimide (5.3 mg) according to the method described above for Example 67 to give the product as a brown oil (4.8 mg); NMR $\delta_H$ (400 MHz, CDCl$_3$) 7.18 (1H, t, J 1.5 Hz), 4.27 (1H, m), 4.18 (1H, m), 3.96 (1H, m), 3.90 (1H, m), 3.08 (2H, q, J 7 Hz), 3.04 (1H, m), 2.97 (1H, dd, J 16.5, 8.5 Hz), 2.65 (1H, m), 2.48 (1H, ddd, J 16, 6, 1 Hz), 1.73 (2H, hex, J 7 Hz), 1.48 (9H, s), 1.23 (3H, d, J 7 Hz) and 1.03 (3H, t, J 7 Hz); m/z M$^+$ 442.18 and 444.16 (M+1).

(4R,9aR)-7-Bromo-6-propanesulfanyl-4-methyl-1,2,3,4,9,9a-hexahydro-1H-2,4a,5-triaza-fluorene (4R,9aR)-7-Bromo-6-propanesulfanyl-4-methyl-1,2,3,4,9,9a-hexahydro-1H-2,4a,5-triaza-fluorene was prepared from (4R,9aR)-7-bromo-6-propanesulfanyl-4-methyl-1,2,3,4,9,9a-hexahydro-1H-2,4a,5-triaza-fluorene-2-carboxylic acid tert-butyl ester (4.2 mg) and trifluoroacetic acid (1 mL) according to the method described above for Example 67 to give the product as a brown oil (2.4 mg); NMR $\delta_H$ (400 MHz, CDCl$_3$) 7.25 (1H, s), 4.50 (1H, m), 4.22 (1H, tdd, J 11.5, 6, 3.5 Hz), 3.32 (1H, dd, J 12, 3.5 Hz), 3.13 (2H, m), 3.09 (2H, m, J 7, 2.5 Hz), 2.79 (1H, t, J 12 Hz), 2.55 (1H, ddd, J 16, 6, 1 Hz), 1.73 (2H, q, J 7 Hz), 1.45 (3H, d, J 7.5 Hz) and 1.04 (3H, t, J 7 Hz).

Example 69

(4R,9aR)-6-(1 (RS)-Ethanol)-7-iodo-4-methyl-1,2,3,4,9,9a-hexahydro-2,4a,5-triaza-fluorene

(4R,9aR)-6-(1(RS)-Ethanol)-iodo-4-methyl-1,2,3,4,9,9a-hexahydro-1H-2,4a,5-triaza-fluorene-2-carboxylic acid tert-butyl ester To a stirred solution of (4R,9aR)-6-bromo-4-methyl-1,2,3,4,9,9a-hexahydro-1H-2,4a,5-triaza-fluorene-2-carboxylic acid tert-butyl ester (1.0 g) in dry tetrahydrofuran (30 mL) at −78° C. under argon was added dropwise a solution of butyl lithium in hexanes (2.5M, 1.2 mL). The mixture was stirred for 1 h then acetaldehyde (0.31 mL) was added dropwise. The mixture was warmed to room temperature, stirred for 30 minutes then partitioned between ethyl acetate (50 mL) and aqueous ammonium chloride solution (50 mL). The organic layer was washed (water), treated with di-tert-butyl dicarbonate (0.5 g), left to stand for 30 minutes then concentrated in vacuo. The residue was purified by flash column chromatography [SiO$_2$; isohexane-ethyl acetate (9:1)→>(1:1)] to give (4R,9aR)-6-(1(RS)-ethanol)-iodo-4-methyl-1,2,3,4,9,9a-hexahydro-1H-2,4a,5-triaza-fluorene-2-carboxylic acid tert-butyl ester as a clear oil (0.43 g), NMR $\delta_H$ (400 MHz, CDCl$_3$) 7.13 (1H, dd, J 7.5, 1 Hz), 6.33 (1H, d, J 7.5 Hz), 4.69 (1H, q, J 6.5 Hz), 4.36 (1H, m), 4.29–3.81 (4H, m), 3.06 (1H, m), 3.01 (1H, dd, J8.5, 8.0 Hz), 2.66 (1H, m ), 2.51 (1H, dd, J 16, 6 Hz), 1.48 (9H, s), 1.44 (3H, d, J 6.5 Hz) and 1.24 (3H, dt, J 6.5, 4 Hz); m/z M$^+$ 334 (M+1).

(4R,9aR)-6-(1(RS)-Ethanol)-7-iodo-4-methyl-1,2,3,4,9,9a-hexahydro-1H-2,4a,5-triaza-fluorene-2-carboxylic acid tert-butyl ester To a stirred solution of (4R,9aR)-6-(1(RS)-ethanol)-4-methyl-1,2,3,4,9,9a-hexahydro-1H-2,4a,5-triaza-fluorene-2-carboxylic acid tert-butyl ester (0.40 g) in dry tetrahydrofuran (10 mL) at 0° C. was added N-iodosuccinimide (0.54 g). The mixture was stirred for 4 hours then partitioned between ethyl acetate (30 mL) and aqueous sodium metabisulfite solution (1M, 30 mL). The organic layer was washed (water, brine) and concentrated in vacuo. The residue was purified by flash column chromatography [SiO$_2$; isohexane-ethyl acetate (9:1) (1:1)] to give (4R,9aR)-6-(1(RS)-ethanol)-7-iodo-4-methyl-1,2,3,4,9,9a-hexahydro-1H-2,4a,5-triaza-fluorene-2-carboxylic acid tert-butyl ester (0.10 g); NMR δ$_H$ (400 MHz, CDCl$_3$) 7.44 (1H, d J 1 Hz), 4.85 (1H, quintet, J 6.5 Hz), 4.36-4.15 (3H, m), 4.00 (2H, m), 3.90 (1H, m), 3.02 (2H, q, J 8.5 Hz), 2.66 (1H, m), 2.53 (1H, dd, J 16.5, 6 Hz), 1.38 (3H, d, J 6.5 Hz) and 1.22 (3H, t, J 7 Hz); m/z M$^+$ 460 (M+1).

(4R,9aR)-6-(1 (RS)-Ethanol)-7-iodo-4-methyl-1,2,3,4,9,9a-hexahydro-2,4a,5-triaza-fluorene A mixture of (4R,9aR)-6-(1(RS)-ethanol)-7-iodo-4-methyl-1,2,3,4,9,9a-hexahydro-1H-2,4a,5-triaza-fluorene-2-carboxylic acid tert-butyl ester (0.012 g), dichloromethane (0.5 mL) and trifluoroacetic acid (0.5 mL) was stirred for 2 hours then partitioned between dichloromethane (5 mL) and aqueous sodium hydroxide solution (2M, 10 mL). The organic layer was filtered through a PTFE membrane and concentrated in vacuo to give (4R,9aR)-6-(1(RS)-ethanol)-7-iodo-4-methyl-1,2,3,4,9,9a-hexahydro-2,4a,5-triaza-fluorene as a clear oil (0.011 g); NMR δ$_H$ (400 MHz, CDCl$_3$) 7.41 (1H, t, J 1 Hz), 4.84 (1H, q, J6 Hz), 4.29 (1H, m), 4.00 (1H, m), 3.08 (1H, tt, J 12, 3.5 Hz), 3.00 (1H, dq, J 9, 1 Hz), 2.94 (1H, dt, J 12, 4 Hz), 2.83 (1H, dd, J 12, 5.5 Hz), 2.62 (1H, q, J 12 Hz), 2.50 (1H, dd, J 16, 7 Hz), 1.38 (3H, d, J 6.5 Hz), and (3H, dd, J8.5, 7.5 Hz); m/z M$^+$ 360 (M+1).

Example 70

(4R,9aR)-7-Ethoxy-4-methyl-1,2,3,4,9,9a-hexahydro-2,4a,5-triaza-fluorene

This compound was prepared in analogy to Example 1 from (4R,9aR)-7-ethoxy-4-methyl-3,4,9,9a-tetrahydro-1H-2,4a,5-triaza-fluorene-2-carboxylic acid tert-butyl ester.

Light yellow oil (84.4%). ISP-MS: m/e=268.4 ([M+H$^+$])

Intermediates a) 5-Ethoxy-pyrrolo[2,3-b]pyridine-1,2-dicarboxylic acid 1-tert-butyl ester 2-ethyl ester This compound was prepared in analogy to example 1, intermediate d) from 5-hydroxy-pyrrolo[2,3-b]pyridine-1,2-dicarboxylic acid 1-tert-butyl ester 2-ethyl ester (Example 3, intermediate d), sodium hydride and ethyl bromide.

Light yellow solid (68.7%). ISP-MS: m/e=335.3 ([M+H$^+$])

b) 5-Ethoxy-1H-pyrrolo[2,3-b]pyridine-2-carboxylic acid ethyl ester

This compound was prepared in analogy to Example 3, intermediate e) from 5-ethoxy-pyrrolo[2,3-b]pyridine-1,2-dicarboxylic acid 1-tert-butyl ester 2-ethyl ester and trifluoroacetic acid.

Light yellow solid (44.1%). ISP-MS: m/e=235.3 ([M+H$^+$])

c) ®-1-(2-tert-Butoxycarbonylamino-1-methylethyl)-5-ethoxy-1H-pyrrolo [2,3-b]pyridine-2-carboxylic acid ethyl ester This compound was prepared in analogy to Example 3, intermediate j) from 5-ethoxy-1H-pyrrolo[2,3-b]pyridine-2-carboxylic acid ethyl ester, potassium tert-butoxide and (S)-5-methyl-2,2-dioxo-[1,2,3]oxathiazolidine-3-carboxylic acid tert-butyl ester.

Colourless oil (59.7%). ISP-MS: m/e=392.3 ([M+H$^+$])

d) 7-Ethoxy-4-methyl-3,4-dihydro-2H-2,4a,5-triaza-fluoren-1-one

This compound was prepared in analogy to Example 3, intermediate k) from (R)-1-(2-tert-butoxycarbonylamino-1-methyl-ethyl)-5-ethoxy-1H-pyrrolo [2,3-b]pyridine-2-carboxylic acid ethyl ester.

Light yellow solid (73.0%). ISP-MS: m/e=246.3 ([M+H$^+$])

e) (R)-7-Ethoxy-4-methyl-3,4-dihydro-1H-2,4a,5-triaza-fluorene-2-carboxylic acid tert-butyl ester This compound was prepared in analogy to Example 1, intermediate h) from 7-ethoxy-4-methyl-3,4-dihydro-2H-2,4a,5-triaza-fluoren-1-one and lithium aluminium hydride and protection of the free amine with di-tert-butyl-dicarbonate and 4-(dimethylamino)pyridine.

Colourless oil (65.1%). ISP-MS: m/e=332.3 ([M+H$^+$])

f) (4R,9aR)-7-Ethoxy-4-methyl-3,4,9,9a-tetrahydro-1H-2,4a,5-triaza-fluorene-2-carboxylic acid tert-butyl ester This compound was prepared in analogy to Example 3, intermediate i) from (R)-7-ethoxy-4-methyl-3,4-dihydro-1H-2,4a,5-triaza-fluorene-2-carboxylic acid tert-butyl ester and sodium cyanoborohydride.

Colourless solid (70.3%). ISP-MS: m/e=334.3 ([M+H$^+$])

Example 71

(4R,9aR)-4,7-Dimethyl-1,2,3,4,9,9a-hexahydro-2,4a,5-triaza-fluorene

This compound was prepared in analogy to example 1 from (4R,9aR)-4,7-dimethyl-3,4,9,9a-tetrahydro-1H-2,4a,5-triaza-fluorene-2-carboxylic acid tert-butyl ester.

Light brown oil (86.4%). ISP-MS: m/e=204.0 ([M+H$^+$])

Intermediates a) 1-(2-tert-Butoxycarbonylamino-1-methyl-ethyl)-5-methyl-1H-pyrrolo [2,3-b]pyridine-2-carboxylic acid ethyl ester This compound was prepared in analogy to Example 3, intermediate j) from 5-methyl-1H-pyrrolo[2,3-b]pyridine-2-carboxylic acid ethyl ester (Example 3, intermediate e), potassium tert-butoxide and (S)-5-methyl-2,2-dioxo-[1,2,3]oxathiazolidine-3-carboxylic acid tert-butyl ester.

Colourless solid (75.1%). ISP-MS: m/e=362.3 ([M+H$^+$])

b) (R)-4,7-Dimethyl-3,4-dihydro-2H-2,4a,5-triaza-fluoren-1-one

This compound was prepared in analogy to Example 3, intermediate k) from 1-(2-tert-butoxycarbonylamino-1-methyl-ethyl)-5-methyl-1H-pyrrolo[2,3-b]pyridine-2-carboxylic acid ethyl ester.

Colourless solid (55.5%). ISP-MS: m/e=216.2 ([M+H$^+$])

c) (R)-4,7-Dimethyl-1,2,3,4-tetrahydro-2,4a,5-triaza-fluorene

This compound was prepared in analogy to Example 3, intermediate l) from (R)-4,7-dimethyl-3,4-dihydro-2H-2,4a,5-triaza-fluoren-1-one and lithium aluminium hydride. The product was purified by column chromatography over silica gel (0.030–0.063 mm) with ethyl acetate:methanol (9:1, then 3:1) as eluant.

Pale yellow solid (51.2%). ISP-MS: m/e=202.0 ([M+H$^+$])

d) (R)-4,7-Dimethyl-3,4-dihydro-1H-2,4a,5-triaza-fluorene-2-carboxylic acid tert-butyl ester This compound was prepared in analogy to Example 3, intermediate m) from (R)-4,7-dimethyl-1,2,3,4-tetrahydro-2,4a,5-triaza-fluorene, di-tert-butyl-dicarbonate and 4-(dimethylamino)pyridine.

Yellow oil (71.6%). ISP-MS: m/e=302.2 ([M+H$^+$])

e) (4R,9aR)-4,7-Dimethyl-3,4,9,9a-tetrahydro-1H-2,4a,5-triaza-fluorene-2-carboxylic acid tert-butyl ester This compound was prepared in analogy to Example 3, intermediate n) from (R)-4,7-dimethyl-3,4-dihydro-1H-2,4a,5-triaza-fluorene-2-carboxylic acid tert-butyl ester and sodium cyanoborohydride.

Colourless oil (78.7%). ISP-MS: m/e=304.2 ([M+H$^+$])

Example 72

(4R,9aR)-7-Ethyl-4-methyl-1,2,3,4,9,9a-hexahydro-1H-2,4a,5-triaza-fluorene di-trifluoroacetate To a solution of (4R,9aR)-7-iodo-4-methyl-1,2,3,4,9,9a-hexahydro-1H-2,4a,5-triaza-fluorene-2-carboxylic acid tert-butyl ester (95 mg) in tetrahydrofuran (1 mL) was added dropwise a solution of isopropylmagnesium chloride in tetrahydrofuran (2M, 0.23 mL). The mixture was shaken for 30 minutes then copper(I) iodide (4 mg) was added. The mixture was shaken for 1 hour. Iodoethane (0.05 mL) was added and the mixture was shaken for 18 h. The mixture was partitioned between aqueous ammonium chloride solution (10 mL) and dichloromethane (10 mL). The organic phase was concentrated in vacuo and purified by reverse phase preparative HPLC (Prep Nova-Pak HR C18 6 Å 60 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give a pale yellow oil (15 mg). The oil was dissolved in DCM (1 mL) and TFA (1 mL). The mixture was left to stand for 1 hour then concentrated in vacuo to give (4R,9aR)-7-ethyl-4-methyl-1,2,3,4,9,9a-hexahydro-1H-2,4a,5-triaza-fluorene di-trifluoroacetate as a yellow gum (21 mg); NMR $\delta_H$ (400 MHz, DMSO-d$_6$) 9.50 (1H, m), 9.01 (1H, m), 7.62 (1H, s), 7.58 (1H, s), 4.49 (1H, quint, J 6.5 Hz), 4.36 (1H, m), 3.44 (1H, dd, J 12, 3 Hz), 3.32–3.19 (3H, m), 3.00 (1H, t, J 11 Hz), 2.84 (1H, dd, J 17.5, 6 Hz), 2.49 (2H, q, J 7.5 Hz), 1.36 (3H, d, J 7 Hz) and 1.13 (3H, t, J 7.5 Hz); HPLC (20% to 50% gradient [95:5 MeOH:water, 10 mmol ammonium acetate] 250 nm XTERRA 2.0 mL/min) 3.80 min.

Example 73

(4R,9aR)-7-Bromo-4-methyl-1,2,3,4,9,9a-hexahydro-1H-2,4a,5-triaza-fluorene (4R,9aR)-7-Bromo-4-methyl-1,2,3,4,9,9a-hexahydro-1H-2,4a,5-triaza-fluorene-2-carboxylic acid tert-butyl ester To a solution of (4R,9aR)-4-methyl-1,2,3,4,9,9a-hexahydro-1H-2,4a,5-triaza-fluorene-2-carboxylic acid tert-butyl ester (10 mg) in tetrahydrofuran (1 mL) was added a solution of N-bromosuccinimide (5.3 mg) in tetrahydrofuran (0.5 mL). The mixture was shaken for 18 h then partitioned between dichloromethane (3 mL) and water (2 mL). The organic layer was filtered through a PTFE frit; the filtrate was concentrated in vacuo. The residue was purified by reverse phase preparative HPLC (Prep Nova-Pak HR C18 6 µm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give (4R,9aR)-7-bromo-4-methyl-1,2,3,4,9,9a-hexahydro-1H-2,4a,5-triaza-fluorene-2-carboxylic acid tert-butyl ester as a yellow oil (4.7 mg); NMR $\delta^H$ (400 MHz, CDCl$_3$) 7.88 (1H, t, J 1 Hz), 7.24 (1H, q, J 1.5 Hz), 4.23 (2H, m), 3.97 (1H, m), 3.89 (1H, m), 3.02 (2H, dd, J 16, 8.5 Hz), 2.65 (1H, m), 2.53 (1H, 16.5, 6.5 Hz), 1.48 (9H, s) and 1.22 (3H, d, J 6.5 Hz).

(4R,9aR)-7-Bromo-4-methyl-1,2,3,4,9,9a-hexahydro-1H-2,4a,5-triaza-fluorene

A solution of (4R,9aR)-7-bromo-4-methyl-1,2,3,4,9,9a-hexahydro-1H-2,4a,5-triaza-fluorene-2-carboxylic acid tert-butyl ester in dichloromethane (1 mL) and trifluoroacetic acid (1 mL) was shaken for 18 h then concentrated in vacuo. The residue was dissolved in methanol (1 mL) and loaded onto an ion-exchange column (SCX-2, 1 g). The column was washed with methanol (5 mL) then with methanolic ammonia solution (7N, 5 mL). The ammonia washings were concentrated in vacuo to give (4R,9aR)-7-bromo-4-methyl-1,2,3,4,9,9a-hexahydro-1H-2,4a,5-triaza-fluorene as a brown oil (2.5 mg); NMR $\delta_H$ (400 MHz, CDCl$_3$) 7.92 (1H, t, J 1 Hz), 7.30 (1H, m), 4.45 (1H, m), 4.18 (1H, tdd, J 9, 6.5, 3.5 Hz), 3.26 (1H, dd, J 12, 3.5 Hz), 3.11 (1H, t, J 8.5 Hz), 3.06 (1H, d, 7 Hz), 3.04 (1H, dd, J 14, 1.5 Hz), 2.74 (1H, t, J 11.5 Hz), 2.57 (1H, dd, J 16, 6 Hz) and 1.42 (3H, d, J 7 Hz); HPLC (50% to 80% gradient [95:5 MeOH:water, 10 mmol ammonium acetate] 235 nm XTERRA 2.0 mL/min) 1.14 min.

Example 74

(4R,9aR)-7-Chloro-4-methyl-1,2,3,4,9,9a-hexahydro-1H-2,4a,5-triaza-fluorene

(4R,9aR)-7-Chloro-4-methyl-1,2,3,4,9,9a-hexahydro-1H-2,4a,5-triaza-fluorene-2-carboxylic acid tert-butyl ester (4R,9aR)-7-chloro-4-methyl-1,2,3,4,9,9a-hexahydro-1H-2,4a,5-triaza-fluorene-2-carboxylic acid tert-butyl ester was prepared from (4R,9aR)-4-methyl-1,2,3,4,9,9a-hexahydro-1H-2,4a,5-triaza-fluorene-2-carboxylic acid tert-butyl ester (10 mg) and N-chlorosuccinimide according to the method described above for Example 73 to give the product as a yellow oil (2.1 mg); NMR $\delta_H$ (400 MHz, CDCl$_3$) 7.79 (1H, t, J 1 Hz), 7.13 (1H, q J 1.5 Hz), 4.28 (2H, m), 3.98 (1H, m), 3.90 (1H, m), 3.02 (1H, dd, J 16.5, 9 Hz), 2.66 (1H, m), 2.53 (1H, dd, J 16, 6 Hz), 1.48 (9H, s) and 1.22 (3H, d, J 7 Hz).

(4R,9aR)-7-Chloro-4-methyl-1,2,3,4,9,9a-hexahydro-1H-2,4a,5-triaza-fluorene (4R,9aR)-7-Chloro-4-methyl-1,2,3,4,9,9a-hexahydro-1H-2,4a,5-triaza-fluorene was prepared from (4R,9aR)-7-chloro-4-methyl-1,2,3,4,9,9a-hexahydro-1H-2,4a,5-triaza-fluorene-2-carboxylic acid tert-butyl ester according to the method described above for Example 73 to give the product as a brown oil (0.9 mg); NMR $\delta_H$ (400 MHz, CDCl$_3$) 7.87 (1H, m), 7.25 (1H, m), 4.59 (1H, m), 4.32 (1H, m), 3.39 (1H, dd, J 12, 3.5 Hz), 3.22–3.13 (2H, m), 2.83 (1H, t, J 12 Hz), 2.62 (1H, dd, J 16.5, 6.5 Hz) and 1.47 (3H, d, J 7.5 Hz); HPLC (50% to 80% gradient [95:5 MeOH:water, 10 mmol ammonium acetate] 235 nm XTERRA 2.0 mL/min) 1.03 min.

Example 75

(4R,9aR)-7-Iodo-4-methyl-1,2,3,4,9,9a-hexahydro-1H-2,4a,5-triaza-fluorene

(4R,9aR)-7-Iodo-4-methyl-1,2,3,4,9,9a-hexahydro-1H-2,4a,5-triaza-fluorene-2-carboxylic acid tert-butyl ester (4R,9aR)-7-Iodo-4-methyl-1,2,3,4,9,9a-hexahydro-1H-2,4a,5-triaza-fluorene-2-carboxylic acid tert-butyl ester was prepared from (4R,9aR)-4-methyl-1,2,3,4,9,9a-hexahydro-1H-2,4a,5-triaza-fluorene-2-carboxylic acid tert-butyl ester (10 mg) and N-iodosuccinimide according to the method described above for Example 73 to give the product as a yellow oil (2.3 mg); NMR $\delta_H$ (400 MHz, CDCl$_3$) 8.01 (1H, t, J 1 Hz), 7.38 (1H, q, J 1.5 Hz), 4.25 (2H, m), 3.97 (1H, m), 3.88 (1H, m), 3.01 (1H, dd, J 16.5, 9 Hz), 2.62 (1H, m), 2.53 (1H, dd, J 16.5, 6.5 Hz), 1.48 (9H, s) and 1.21 (3H, d, J 7 Hz); MS, Found: e/z$^+$ 416, 360 (M+1, M–$^t$Bu).

(4R,9aR)-7-Iodo-4-methyl-1,2,3,4,9,9a-hexahydro-1H-2,4a,5-triaza-fluorene (4R,9aR)-7-Iodo-4-methyl-1,2,3,4,9,9a-hexahydro-1H-2,4a,5-triaza-fluorene was prepared from (4R,9aR)-7-iodo-4-methyl-1,2,3,4,9,9a-hexahydro-1H-2,4a,5-triaza-fluorene-2-carboxylic acid tert-butyl ester according to the method described above for Example 73 to give the product as a brown oil (1.0 mg); NMR $\delta_H$ (400 MHz, CDCl$_3$) 8.09 (1H, t, J 1 Hz), 7.50 (1H, q, J 1.5 Hz), 4.59 (1H, m), 4.32 (1H, tdd, J 12, 6, 3.5 Hz), 3.22–3.12 (3H, m), 2.83 (1H, t, J 12 Hz), 2.62 (1H, dd, J 16.5, 6 Hz) and 1.47 (3H, d, J 7.5 Hz); HPLC (50% to 80% gradient [95:5 MeOH:water, 10 mmol ammonium acetate] 235 nm XTERRA 2.0 mL/min) 1.34 min.

Example 76

(4R,9aR)-7-Ethoxymethyl-4-methyl-1,2,3,4,9,9a-hexahydro-1H-2,4a,5-triaza-fluorene di-trifluoroacetate

(4R,9aR)-7-Formyl-4-methyl-1,2,3,4,9,9a-hexahydro-1H-2,4a,5-triaza-fluorene-2-carboxylic acid tert-butyl ester To a stirred solution of (4R,9aR)-7-iodo-4-methyl-1,2,3,4,9,9a-hexahydro-1H-2,4a,5-triaza-fluorene-2-carboxylic acid tert-butyl ester (575 mg) in tetrahydrofuran (6 mL) under argon was added dropwise a solution of isopropylmagnesium chloride in tetrahydrofuran (2M, 1.39 mL). The mixture was stirred 1 hour then dimethylformamide (0.30 mL) was added dropwise. The mixture was stirred for 2 hours then partitioned between aqueous ammonium chloride solution (20 mL) and ethyl acetate (2×20 mL). The combined organic extracts were washed with brine, dried over magnesium sulfate and concentrated in vacuo. The residue was purified by flash column chromatography [SiO$_2$; isohexane-ethyl acetate (3:1)] to give (4R,9aR)-7-formyl-4-methyl-1,2,3,4,9,9a-hexahydro-1H-2,4a,5-triaza-fluorene-2-carboxylic acid tert-butyl ester as a yellow foam (347 mg).

(4R,9aR)-7-Hydroxymethyl-4-methyl-1,2,3,4,9,9a-hexahydro-1H-2,4a,5-triaza-fluorene-2-carboxylic acid tert-butyl ester To a stirred solution of (4R,9aR)-7-formyl-4-methyl-1,2,3,4,9,9a-hexahydro-1H-2,4a,5-triaza-fluorene-2-carboxylic acid tert-butyl ester (347 mg) in ethanol (10 mL) was added sodium borohydride (43 mg). The mixture was stirred for 3 hours then partitioned between water (20 mL) and dichloromethane (2×20 mL). The combined organic layers were washed with brine, dried over magnesium sulfate and concentrated in vacuo. The residue was purified by flash column chromatography (SiO$_2$; ethyl acetate) to give (4R,9aR)-7-hydroxymethyl-4-methyl-1,2,3,4,9,9a-hexahydro-1H-2,4a,5-triaza-fluorene-2-carboxylic acid tert-butyl ester as a pale yellow foam (221 mg); NMR $\delta_H$ (400 MHz, CDCl$_3$) 7.77 (1H, m), 7.25 (1H, q, J 1.5 Hz), 4.48 (2H, s), 4.32 (1H, m), 4.20 (1H, m), 3.97 (1H, m), 3.90 (1H, m), 3.02 (2H, dd, J 16, 9 Hz), 2.65 (1H, m), 2.53 (1H, dd, J 16, 6.5 Hz), 1.98 (1H, m), 1.48 (9H, s) and 1.23 (3H, d, J 6.5 Hz); MS, Found: (e/z)$^+$ 320, 264 (M+1, M–$^t$Bu).

(4R,9aR)-7-Ethoxymethyl-4-methyl-1,2,3,4,9,9a-hexahydro-1H-2,4a,5-triaza-fluorene di-trifluoroacetate To a solution of (4R,9aR)-7-hydroxymethyl-4-methyl-1,2,3,4,9,9a-hexahydro-1H-2,4a,5-triaza-fluorene-2-carboxylic acid tert-butyl ester (30 mg) in N,N-dimethylformamide (1 mL) was added sodium hydride (60%, 6 mg). The mixture was shaken for 25 minutes then ethyl iodide (0.015 mL) was added. The mixture was shaken for 18 h, then a further portion of sodium hydride was added (6 mg). The mixture was heated to 60° C. and shaken for 18 h. The mixture was cooled to room temperature then partitioned between brine (10 mL) and dichloromethane (10 mL). The organic layer was washed with aqueous magnesium sulfate solution and concentrated in vacuo. The residue was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give a yellow oil (13 mg). The oil was dissolved in DCM (1 mL) and TFA (1 mL). The mixture was left to stand for 2 hours then concentrated in vacuo to give (4R,9aR)-7-ethoxymethyl-4-methyl-1,2,3,4,9,9a-hexahydro-1H-2,4a,5-triaza-fluorene di-trifluoroacetate as a yellow gum (35 mg); NMR $\delta_H$ (400 MHz, DMSO-$d_6$) 9.36 (1H, m), 8.90 (1H, m), 7.76 (1H, s), 7.48 (1H, s), 4.48 (1H, dt, J 11, 6.5 Hz), 4.29 (2H, s), 4.25 (1H, m), 3.45 (2H, q, J 6.5 Hz), 3.39 (1H, dd, J 12.5, 3.5 Hz), 3.27 (1H, d, J 13 Hz), 3.21 (1H, t, J 8.5 Hz), 3.17 (1H, m), 2.94 (1H, m), 2.78 (1H, dd, J 16.5, 6 Hz), 1.34 (3H, d, J 7 Hz) and 1.12 (3H, t, J 7 Hz); HPLC (20% to 50% gradient [95:5 MeOH:water, 10 mmol ammonium acetate] 260 nm XTERRA 2.0 mL/min) 1.52 min.

Example 77

(4R,9aR)-7-Benzyloxymethyl-4-methyl-1,2,3,4,9,9a-hexahydro-1H-2,4a,5-triaza-fluorene di-trifluoroacetate (4R,9aR)-7-Benzyloxymethyl-4-methyl-1,2,3,4,9,9a-hexahydro-1H-2,4a,5-triaza-fluorene di-trifluoroacetate was prepared from (4R,9aR)-7-hydroxymethyl-4-methyl-1,2,3,4,9,9a-hexahydro-1H-2,4a,5-triaza-fluorene-2-carboxylic acid tert-butyl ester (30 mg) and benzyl bromide (0.022 mL) according to the procedures described above for Example 76 to give the product as a yellow gum (36 mg); NMR $\delta_H$ (400 MHz, DMSO-$d_6$) 9.35 (1H, m), 8.90 (1H, m), 7.79 (1H, d, J 1.5 Hz), 7.50 (1H, d, J 1.5 Hz), 7.38–7.26 (5H, m), 4.51 (2H, s), 4.48 (1H, m), 4.38 (2H, s), 4.26 (1H, tdd, J 12, 6, 3.5 Hz), 3.39 (1H, dd, J 12.5, 3.5 Hz), 3.27 (1H, d, J 113 Hz), 3.21 (1H, t, J 8 Hz), 3.17 (1H, m), 2.94 (1H, m), 2.77 (1H, dd, J 17, 6 Hz) and 1.34 (3H, d, J 7 Hz); HPLC (50% to 80% gradient [95:5 MeOH:water, 10 mmol ammonium acetate] 265 nm XTERRA 2.0 mL/min) 1.53 min.

Example 78

(4R,9aR)-7-Methoxymethyl-4-methyl-1,2,3,4,9,9a-hexahydro-1H-2,4a,5-triaza-fluorene di-trifluoroacetate To a stirred solution of (4R,9aR)-7-hydroxymethyl-4-methyl-1,2,3,4,9,9a-hexahydro-1H-2,4a,5-triaza-fluorene-2-carboxylic acid tert-butyl ester (80 mg) in DCM (3 mL) at 0° C. was added dropwise diethylaminosulfur trifluoride (0.066 mL). The mixture was stirred for 3 hours then a further portion of diethylaminosulfur trifluoride was added (0.033 mL). The mixture was stirred for 30 minutes then partitioned between aqueous sodium hydrogencarbonate solution (10 mL) and dichloromethane (10 mL). The organic layer was washed with brine, dried over magnesium sulfate and concentrated in vacuo. The residue was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give a pale yellow oil (15 mg). The oil was dissolved in DCM (1 mL) and TFA (1 mL), left to stand for 1 hour then concentrated in vacuo to give (4R,9aR)-7-methoxymethyl-4-methyl-1,2,3,4,9,9a-hexahydro-1H-2,4a,5-triaza-fluorene di-trifluoroacetate as a yellow oil (25 mg); NMR $\delta_H$ (400 MHz, DMSO-$d_6$) 9.33 (1H, m), 8.88 (1H, m), 7.76 (1H, d, J 1 Hz), 7.45 (1H, d, J 1 Hz), 4.47 (1H, dt, J 12.5, 7 Hz), 4.25 (2H, s), 4.23 (1H, m), 3.38 (1H, dd, J 12, 3.5 Hz), 3.26 (1H, d, J 13 Hz), 3.24 (3H, s), 3.19 (1H, t, J 8 Hz), 3.16 (1H, m), 2.93 (1H, m), 2.76 (1H, dd, J 17, 6 Hz) and 1.33 (3H, d, J 7 Hz). MS, Found: e/z$^+$ 234 (M+1).

Example 79

(4R,9aR)-7-Cyclopropylmethoxy-4-methyl-1,2,3,4,9,9a-hexahydro-1H-2,4a,5-triaza-fluorene di-trifluoroacetate (4R,9aR)-7-Hydroxy-4-methyl-1,2,3,4,9,9a-hexahydro-1H-2,4a,5-triaza-fluorene-2-carboxylic acid tert-butyl ester To a stirred solution of (4R,9aR)-7-bromo-4-methyl-1,2,3,4,9,9a-hexahydro-1H-2,4a,5-triaza-fluorene-2-carboxylic acid tert-butyl ester (0.50 g) in ether (35 mL) at −100° C. under nitrogen were added dropwise sequentially triisopropylborate (0.607 mL) then a solution of tert-butyllithium (1.5 M, 1.04 mL). The mixture was stirred for 10 minutes, warmed to −78° C. and stirred for 10 minutes then warmed to -20° C. A mixture of acetic acid (0.33 mL) and water (0.33 mL) was added dropwise followed by aqueous hydrogen peroxide (27%, 0.25 mL). The mixture was warmed to room temperature, stirred for 2 hours then partitioned between aqueous sodium metabisulfite solution (30 mL) and ethyl acetate (30 mL). The organic phase was washed with brine, dried over magnesium sulfate and concentrated in vacuo to give a yellow oil. The oil was purified by flash column chromatography [SiO$_2$; ethyl acetate-isohexane (1:1) (3:2)] to give (4R,9aR)-7-hydroxy-4-methyl-1,2,3,4,9,9a-hexahydro-1H-2,4a,5-triaza-fluorene-2-carboxylic acid tert-butyl ester as a yellow foam (0.21 g); NMR $\delta_H$ (400 MHz, CDCl$_3$) 7.51 (1H, d, J 2.5 Hz), 6.96 (1H, d, J 2.5 Hz), 4.20 (2H, m), 3.88 (1H, tdd, J 8, 7, 3.5 Hz), 3.04 (1H, m), 2.96 (1H, dd, J 16, 8.5 Hz), 2.66 (1H, m), 2.49 (1H, dd, J 16, 7 Hz), 1.47 (9H, s) and 1.18 (3H, d, J 6.5 Hz); HPLC (20% to 50% gradient [95:5 MeOH:water, 10 mmol ammonium acetate] 250 nm XTERRA 2.0 mL/min) 7.16 min.

(4R,9aR)-7-Cyclopropylmethoxy-4-methyl-1,2,3,4,9,9a-hexahydro-1H-2,4a,5-triaza-fluorene di-trifluoroacetate To a solution of (4R,9aR)-7-hydroxy-4-methyl-1,2,3,4,9,9a-hexahydro-1H-2,4a,5-triaza-fluorene-2-carboxylic acid tert-butyl ester (51 mg) in N,N-dimethylformamide (1 mL) was added sodium hydride (60%, 14 mg). The mixture was shaken for 2 minutes then cyclopropylmethyl bromide (0.033 mL) was added. The mixture was shaken for 18 hours then partitioned between dichloromethane (5 mL) and aqueous ammonium chloride solution (5 mL). The organic layer was concentrated in vacuo. The residue was purified by reverse phase preparative HPLC (Prep Nova-Pak HR C18 6 μm 60 Å 30 mm×300 mm column, UV detection at 254 nm, mobile phase 95:5 methanol:water and 10 mmol ammonium acetate, gradient 50 methanol to 100% 0 to 10 min then 100% methanol to 13 min, 20 mL/min) to give a yellow oil (13 mg). The oil was dissolved in DCM (1 mL) and TFA (1 mL). The mixture was left to stand for 1 hour then concentrated in vacuo to give (4R,9aR)-7-cyclopropylmethoxy-4-methyl-1,2,3,4,9,9a-hexahydro-1H-2,4a,5-triaza-fluorene di-trifluoroacetate as a brown oil (30 mg); NMR $\delta_H$ (400 MHz, DMSO-d$_6$) 9.31 (1H, m), 8.85 (1H, m), 7.46 (1H, d, J 2.5 Hz), 7.36 (1H, m), 4.40 (1H, dt, J 12, 7 Hz), 4.19 (1H, tdd, J 11.5, 6, 3.5 Hz), 3.76 (2H, d, J 6.5 Hz), 3.36 (1H, dd, J 11.5,2.5 Hz), 3.25 (1H, d, J 13 Hz), 3.17 (1H, dd, J 17, 9 Hz), 3.13 (1H, m), 2.91 (1H, q, J 11 Hz), 2.74 (1H, dd, J 17, 6 Hz), 1.31 (3H, d, J 7 Hz) and 1.18 (1H, m); HPLC (20% to 50% gradient [95:5 MeOH:water, 10 mmol ammonium acetate] 250 nm XTERRA 2.0 mL/min) 2.76 min.

Example 80

(4R,9aR)-7-Fluoro-4,8-dimethyl-1,2,3,4,9,9a-hexahydro-2,4a,5-triaza-fluorene

To a solution of 0.068 g (4R,9aR)-7-fluoro-8-hydroxymethyl-4-methyl-3,4,9,9a-tetrahydro-1H-2,4a,5-triaza-fluorene-2-carboxylic acid tert-butyl ester in 3 mL of dichloromethane was added 0.0995 g tetrabromomethane and 0.0786 g triphenylphosphine and the mixture was stirred at ambient temperature for 2.5 h The reaction mixture was concentrated and the residue was purified by chromatography on silica gel with a mixture of heptane:ethyl acetate (1:1) to yield 0.0695 g of a slightly yellow oil. This oil was dissolved in 1 mL tetrahydrofuran and 3.0 mg palladium acetate was added. To the resulting mixture was added 0.05 mL polymethylhydrosiloxane and the mixture was stirred at room temperature for 0.5 h. The reaction mixture was partitioned between water and ethyl acetate. The organic phase was washed with water and dried over sodium sulfate and evaporated. The residue was dissolved in 0.60 mL trifluoroacetic acid and stirred at room temperature for 0.5 h. The solvent was evaporated and the residue was purified by chromatography on silica gel with dichloromethane:methanol:ammonia (25% in water) (9:1:0.1) to yield 0.032 g (4R,9aR)-7-fluoro-4,8-dimethyl-1,2,3,4,9,9a-hexahydro-2,4a,5-triaza-fluorene as a slightly yellow oil.

ISP-MS: m/e=222.3 ([M+H$^+$]).

Intermediate (4R,9aR)-7-Fluoro-8-hydroxymethyl-4-methyl-3,4,9,9a-tetrahydro-1H-2,4a,5-triaza-fluorene-2-carboxylic acid tert-butyl ester To a solution of 0.800 g (4R,9aR)-7-fluoro-8-formyl-4-methyl-3,4,9,9a-tetrahydro-1H-2,4a,5-triaza-fluorene-2-carboxylic acid tert-butyl ester (intermediate i, examples 54–61) in 15 mL tetrahydrofurane was added 0.052 g lithium borohydride and the mixture was stirred at room temperature for 0.5 h. The reaction mixture was partitioned between water and ethyl acetate. The organic phase was washed twice with water dried over sodium sulfate and evaporated. The residue was purified by chromatography on silica gel with methylenechloride:ethyl acetate (3:2) to yield 0.56 g (4R,9aR)-7-fluoro-8-hydroxymethyl-4-methyl-3,4,9,9a-tetrahydro-1H-2,4a,5-triaza-fluorene-2-carboxylic acid tert-butyl ester as colorless foam.

ISP-MS: m/e=338.2 ([M+H$^+$]).

Example 81

(4R,9aR)-(7-Fluoro-4-methyl-1,2,3,4,9,9a-hexahydro-2,4a,5-triaza-fluoren-8-yl)-methanol A mixture of 0.040 g (4R,9aR)-7-fluoro-8-hydroxymethyl-4-methyl-3,4,9,9a-tetrahydro-1H-2,4a,5-triaza-fluorene-2-carboxylic acid tert-butyl ester in 1 mL of a 2M solution of hydrochloric acid in dioxane was kept at room temperature for 18 h. The solvents were evaporated and the residue was purified by chromatography on silica gel with dichloromethane:methanol:ammonia (25% in water ) (9:1: 0.1). The product fractions were collected and evaporated to yield 0.0215 g of yellowish foam.

ISP-MS: m/e=238.4 ([M+H$^+$]).

Example 82

(4R,9aR)-7-Fluoro-8-methoxymethyl-4-methyl-1,2,3,4,9,9a-hexahydro-2,4a,5-triaza-fluorene To a solution of 0.116 g (4R,9aR)-7-fluoro-8-hydroxymethyl-4-methyl-3,4,9,9a-tetrahydro-1H-2,4a,5-triaza-fluorene-2-carboxylic acid tert-butyl ester in 2 mL dimethylformamide was added 0.050 g sodium hydride (55% suspension in oil) and 0.146 g methyl iodide. The mixture was stirred at room temperature for 20 h. The reaction mixture was partitioned between water and ethyl acetate. The organic phase was evaporated and the residue was purified by chromatography on silica gel with heptane:ethyl acetate to yield 0.113 g of yellowish oil. The oil was dissolved in 1 mL trifluoroacetic acid and kept at room temperature for 1 h. The solvent was evaporated and the residue was purified by chromatography on silica gel with dichloromethane:methanol:ammonia (25% in water) (9:1: 0.1) to yield 0.074 g (4R,9aR)-7-fluoro-8-methoxymethyl-4-methyl-1,2,3,4,9,9a-hexahydro-2,4a,5-triaza-fluorene as a yellow oil.

ISP-MS: m/e=252.3 ([M+H$^+$]).

Example 83

(4R,9aR)-7-Fluoro-4-methyl-1,2,3,4,9,9a-hexahydro-2,4a,5-triaza-fluorene-8-carbaldehyde oxime In analogy to example 58 starting from (4R,9aR)-7-fluoro-8-formyl-4-methyl-3,4,9,9a-tetrahydro-1H-2,4a,5-triaza-fluorene-2-carboxylic acid tert-butyl ester and hydroxylamine hydrochloride was prepared (4R,9aR)-7-fluoro-4-methyl-1,2,3,4,9,9a-hexahydro-2,4a,5-triaza-fluorene-8-carbaldehyde oxime. m.p.: 194.6–196.7° C.

Example 84

(4R,9aR)-7-Fluoro-4-methyl-1,2,3,4,9,9a-hexahydro-2,4a,5-triaza-fluorene-8-carbaldehyde O-methyl-oxime In analogy to example 58 starting from (4R,9aR)-7-fluoro-8-formyl-4-methyl-3,4,9,9a-tetrahydro-1H-2,4a,5-triaza-fluorene-2-carboxylic acid tert-butyl ester and O-methyl hydroxylamine hydrochloride was prepared (4R,9aR)-7-fluoro-4-methyl-1,2,3,4,9,9a-hexahydro-2,4a,5-triaza-fluorene-8-carbaldehyde O-methyl-oxime.

ISP-MS: m/e=265.3 ([M+H$^+$]).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| | |
| --- | --- |
| Compound of formula I | 3.0 mg |
| Gelatine | 150.0 mg |
| Phenol | 4.7 mg |
| Water for injection solutions | ad 1.0 mL |

What is claimed is:

1. A compound of formula (I):

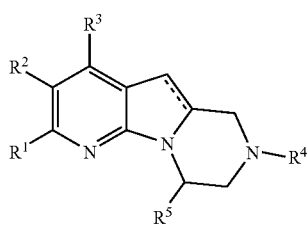

(I)

wherein
R$^1$ is hydrogen, alkyl, cycloalkyl, halogen, alkoxy, cycloalkoxy, alkoxyalkyl, cycloalkoxyalkyl, cycloalkylalkoxyalkyl, cycloalkylalkoxy, hydroxyalkyl, R$^8$—O—N═(R$^6$)C—, alkylsulfanyl or alkyl substituted with halogen;
R$^2$ is alkyl, cycloalkyl, alkoxy, cycloalkoxy, cycloalkylalkoxy, halogen, hydroxy, hydroxyalkyl, alkoxyalkyl, cycloalkylalkoxy, cycloalkoxyalkyl, cycloalkylalkoxy, alkoxyalkoxy, cycloalkylalkoxyalkyl, hydroxyalkoxy, alkyl-SO$_2$— or aralkoxyalkyl;
R$^3$ is hydrogen, alkyl, cycloalkyl, hydroxyalkyl, alkoxyalkyl, cycloalkoxyalkyl or R$^7$—O—N═CH—;
R$^4$ is hydrogen or alkyl;
R$^5$ is alkyl;
R$^6$ is hydrogen or alkyl;
R$^7$ is hydrogen, alkyl or cycloalkyl;
R$^8$ is hydrogen, alkyl or cycloalkyl;
or a pharmaceutically acceptable salt or ester thereof.

2. The compound according to claim 1, wherein R$^1$ is hydrogen, alkyl, cycloalkylalkoxyalkyl or hydroxyalkyl.

3. The compound according to claim 1, wherein R$^2$ is alkyl, alkoxy, halogen or alkoxyalkoxy.

4. The compound according to claim 1, wherein R$^3$ is hydrogen.

5. The compound according to claim 1, wherein the compound is of formula Ia:

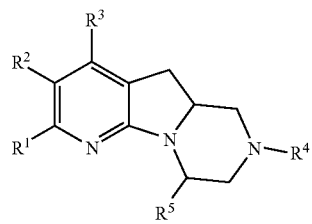

(Ia)

6. The compound according to claim 1, wherein R$^4$ is hydrogen.

7. The compound according to claim 1, wherein the compound is of formula Ic:

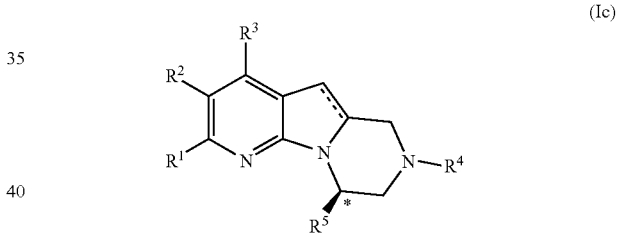

(Ic)

wherein the carbon atom C* to which R$^5$ is attached is of the R configuration.

8. The compound according to claim 1, wherein R$^5$ is methyl.

9. The compound according to claim 1, wherein R$^6$ is hydrogen or methyl.

10. The compound according to claim 1, wherein R$^7$ is hydrogen or methyl.

11. The compound according to claim 1, wherein R$^8$ is methyl.

12. The compound according to claim 1 selected from the group consisting of:
   (4R,9aR)-7-ethoxy-4,6-dimethyl-1,2,3,4,9,9a-hexahydro-2,4a,5-triaza-fluorene;
   (4R,9aR)-7-(2-methoxy-ethoxy)-4,6-dimethyl-1,2,3,4,9,9a-hexahydro-2,4a,5-triaza-fluorene;
   (4R,9aR)-4,6,7-trimethyl-1,2,3,4,9,9a-hexahydro-2,4a,5-triaza-fluorene;
   (4R,9aR)-7-fluoro-4-methyl-1,2,3,4,9,9a-hexahydro-2,4a,5-triaza-fluorene;
   (4R,9aR)-6-cyclopropylmethoxymethyl-7-fluoro-4-methyl-1,2,3,4,9,9a-hexahydro-2,4a,5-triaza-fluorene;
   1-(S)-[(4R,9aR)-7-fluoro-4-methyl-1,2,3,4,9,9a-hexahydro-2,4a,5-triaza-fluoren-6-yl]-ethanol; and (4R,9aR)-6-(1-(S)-cyclopropylmethoxy-ethyl)-7-fluoro-4-methyl-1,2,3,4,9,9a-hexahydro-2,4a,5-triaza-fluorene.

13. The compound according to claim 5 wherein:
$R^1$ is hydrogen, alkyl, cycloalkyl-alkoxyalkyl or hydroxyalkyl;
$R^2$ is alkyl, alkoxy, halogen or alkoxyalkoxy; and
$R^3$ is hydrogen.

14. The compound according to claim 13, wherein $R^4$ is hydrogen.

15. The compound according to claim 13, wherein $R^5$ is methyl.

16. The compound according to claim 7, wherein:
$R^1$ is hydrogen, alkyl, cycloalkyl-alkoxyalkyl or hydroxyalkyl;
$R^2$ is alkyl, alkoxy, halogen or alkoxyalkoxy; and
$R^3$ is hydrogen.

17. The compound according to claim 16, wherein $R^4$ is hydrogen.

18. The compound according to claim 16, wherein $R^5$ is methyl.

19. A pharmaceutical composition comprising a compound in accordance with claim 1 and a therapeutically inert carrier.

20. A method for the treatment of obesity in a patient in need of such treatment, comprising administering to said patient an effective amount of a compound according to claim 1.

21. A pharmaceutical composition comprising a compound according to claim 1 and orlistat, and a therapeutically inert carrier.

* * * * *